United States Patent
McAteer et al.

(10) Patent No.: US 12,357,531 B2
(45) Date of Patent: Jul. 15, 2025

(54) HANDHELD FOCUSED EXTRACORPOREAL SHOCK WAVE THERAPY DEVICE, KIT, AND METHOD

(71) Applicant: Curative Sound, LLC, Carmel, IN (US)

(72) Inventors: Jeffrey Phillip McAteer, Carmel, IN (US); Geoffry N. Barber, New Castle, IN (US); James V. Olson, Jr., Indianapolis, IN (US); Randal Douglas Wood, New Palestine, IN (US)

(73) Assignee: Curative Sound, LLC, Carmel, IN (US)

( * ) Notice: Subject to any disclaimer, the term of this patent is extended or adjusted under 35 U.S.C. 154(b) by 491 days.

(21) Appl. No.: 17/658,581

(22) Filed: Apr. 8, 2022

(65) Prior Publication Data

US 2023/0125586 A1 Apr. 27, 2023

Related U.S. Application Data

(60) Provisional application No. 63/267,048, filed on Jan. 22, 2022, provisional application No. 63/263,102, filed on Oct. 27, 2021.

(51) Int. Cl.
*A61H 23/00* (2006.01)
*A61B 17/00* (2006.01)
(Continued)

(52) U.S. Cl.
CPC ......... *A61H 23/008* (2013.01); *A61B 17/225* (2013.01); *B06B 1/0215* (2013.01);
(Continued)

(58) Field of Classification Search
CPC .......... A61H 23/008; A61H 2201/0153; A61H 2201/1207; A61H 2201/5005;
(Continued)

(56) References Cited

U.S. PATENT DOCUMENTS

| 4,526,168 A | 7/1985 | Dassler et al. |
| 4,658,155 A | 4/1987 | Ohba et al. |

(Continued)

FOREIGN PATENT DOCUMENTS

| CN | 102871830 A † | 1/2013 |
| CN | 210078264 | 2/2020 |

(Continued)

OTHER PUBLICATIONS

International Search Report corresponding to PCT Application No. PCT/US2022/078676, mailed May 11, 2023 (13 pages).

(Continued)

*Primary Examiner* — Joel Lamprecht
*Assistant Examiner* — Amy Shafqat
(74) *Attorney, Agent, or Firm* — Maginot, Moore & Beck

(57) ABSTRACT

A focused extracorporeal shock wave therapy (f-ESWT) device includes a handheld housing, a battery, and a transducer assembly. The battery is located in the handheld housing. The transducer assembly is located in the handheld housing and is operably connected to the battery. The transducer assembly is configured to generate a focused shock wave using electrical energy from the battery.

20 Claims, 25 Drawing Sheets

(51) Int. Cl.
| | |
|---|---|
| *A61B 17/225* | (2006.01) |
| *B06B 1/02* | (2006.01) |
| *B06B 1/06* | (2006.01) |
| *H03K 19/177* | (2020.01) |

(52) U.S. Cl.
CPC .......... *B06B 1/0607* (2013.01); *B06B 1/0622* (2013.01); *A61B 2017/0003* (2013.01); *A61B 2017/00464* (2013.01); *A61B 2017/00734* (2013.01); *A61H 2201/0153* (2013.01); *A61H 2201/1207* (2013.01); *A61H 2201/5005* (2013.01); *A61H 2201/5046* (2013.01); *B06B 2201/76* (2013.01); *H03K 19/177* (2013.01)

(58) Field of Classification Search
CPC .... A61H 2201/5046; A61H 2201/0157; A61H 2201/1685; A61H 2201/5007; A61H 2201/503; A61H 23/0245; A61H 23/00; A61B 17/225; A61B 2017/0003; A61B 2017/00464; A61B 2017/00734; A61B 17/2251; A61B 2017/00761; A61B 17/22004; A61B 5/025; B06B 1/0215; B06B 1/0607; B06B 1/0622; B06B 2201/76; B06B 2201/55; H03K 19/177; A61N 2007/0065; A61N 2007/0078; A61N 7/00

See application file for complete search history.

(56) References Cited

U.S. PATENT DOCUMENTS

| | | | |
|---|---|---|---|
| 4,796,632 A | 1/1989 | Boyd et al. | |
| 5,009,232 A | 4/1991 | Hassler et al. | |
| 5,050,588 A | 9/1991 | Grey et al. | |
| 5,111,805 A | 5/1992 | Jaggy et al. | |
| 5,119,801 A | 6/1992 | Eizenhoefer et al. | |
| 5,174,294 A | 12/1992 | Saito et al. | |
| 5,193,527 A | 3/1993 | Schaefer | |
| 5,247,924 A | 9/1993 | Suzuki et al. | |
| 5,409,446 A | 4/1995 | Rattner | |
| 5,524,625 A | 6/1996 | Okazaki et al. | |
| 5,549,110 A | 8/1996 | Krauss et al. | |
| 6,203,498 B1* | 3/2001 | Bunce ................ | G01S 7/52028 |
| | | | 600/440 |
| 6,312,434 B1 | 11/2001 | Sutrina et al. | |
| 6,985,869 B1 | 1/2006 | Stoll et al. | |
| 7,029,446 B2 | 4/2006 | Wendelken et al. | |
| 7,189,209 B1 | 3/2007 | Ogden et al. | |
| 7,867,178 B2 | 1/2011 | Simnacher | |
| 8,088,073 B2 | 1/2012 | Simnacher et al. | |
| 9,522,011 B2 | 12/2016 | Cioanta et al. | |
| 10,058,340 B2 † | 8/2018 | Cioanta | |
| 10,089,443 B2 | 10/2018 | Miller et al. | |
| 10,194,930 B2 | 2/2019 | Du | |
| 10,441,499 B1 | 10/2019 | Zhu et al. | |
| 10,465,507 B2 | 11/2019 | McRory | |
| 10,561,862 B2 | 2/2020 | Slayton | |
| 10,653,581 B2 | 5/2020 | Hoffman | |
| 10,661,007 B2 | 5/2020 | Estes | |
| 2002/0045849 A1 | 4/2002 | Krauss et al. | |
| 2003/0233045 A1 | 12/2003 | Vaezy et al. | |
| 2004/0234453 A1 | 11/2004 | Smith | |
| 2006/0036194 A1 | 2/2006 | Schultheiss et al. | |
| 2009/0204433 A1 | 8/2009 | Darian et al. | |
| 2010/0113984 A1 | 5/2010 | Leonetti et al. | |
| 2013/0289593 A1* | 10/2013 | Hall ........................ | A61N 7/02 |
| | | | 264/109 |
| 2017/0028225 A1* | 2/2017 | Atsuchi ..................... | A61N 7/00 |
| 2018/0140278 A1* | 5/2018 | Bromberg ............ | A61B 8/4494 |
| 2018/0221688 A1* | 8/2018 | Cioanta ................ | G05B 13/026 |
| 2018/0296432 A1* | 10/2018 | Warlick ................ | A61H 23/008 |
| 2020/0245971 A1 | 8/2020 | Lindekugel et al. | |
| 2020/0269073 A1 | 8/2020 | Warbington et al. | |
| 2022/0117784 A1* | 4/2022 | Potter, Jr. ............ | A61F 9/00781 |
| 2022/0287878 A1* | 9/2022 | Herekar ................ | A61F 9/0017 |

FOREIGN PATENT DOCUMENTS

| | | |
|---|---|---|
| DE | 2202989 | 7/1973 |
| DE | 19509004 | 10/1996 |
| EP | 0527651 | 2/1993 |
| EP | 0444680 B1 | 6/1998 |
| EP | 1479412 | 10/2008 |
| EP | 3689418 | 8/2020 |
| WO | 2019216509 | 11/2019 |

OTHER PUBLICATIONS

Oceanus, OCE-ESWT-003 Type II, Oceanus Shock Wave Therapy Device (EDX), available at: http://oceanuswave.com/product_more?product_id=111, available on or before Oct. 27, 2021 (2 pages).

Oceanus, OCE-ESWT-003, available at: http://oceanuswave.com/product_more?product_id=68, available on or before Oct. 27, 2021 (3 pages).

Launch Medical, The Phoenix, available at: https://www.getmyphoenix.com/how-it-works/, available on or before Oct. 27, 2021 (5 pages).

Wifiultras, Color WiFi Wireless Ultrasound Scanner with Changeable Probe Heads, available at: https://wifiultras.com/products/color-wifi-wireless-ultrasound-scanner-with-changeable-probe-heads-linear-convex, available on or pefore Oct. 27, 2021 (6 pages).

Pickelmann et al., HILTI AG, High Power Piezoelectric Axial Shockwave Generation, 2008 (23 pages).

Storz Medical, CuraMedix, The Art of the Shock Wave, Physics and Technology, available on or before Oct. 27, 2021 (20 pages).

Kamel, T.M., Poling of Hard Ferroelectric PZT Ceramics, Journal of the European Ceramic Society, 2008 (12 pages).

Pettit-Dowd, Sandra, Indications and Beneficial Effects in Veterinary Medicine, Veterinary Nursing in Action, pp. 42-48, Feb./Mar. 2017, The Navta Journal, Bridgewater, NJ.†

\* cited by examiner
† cited by third party

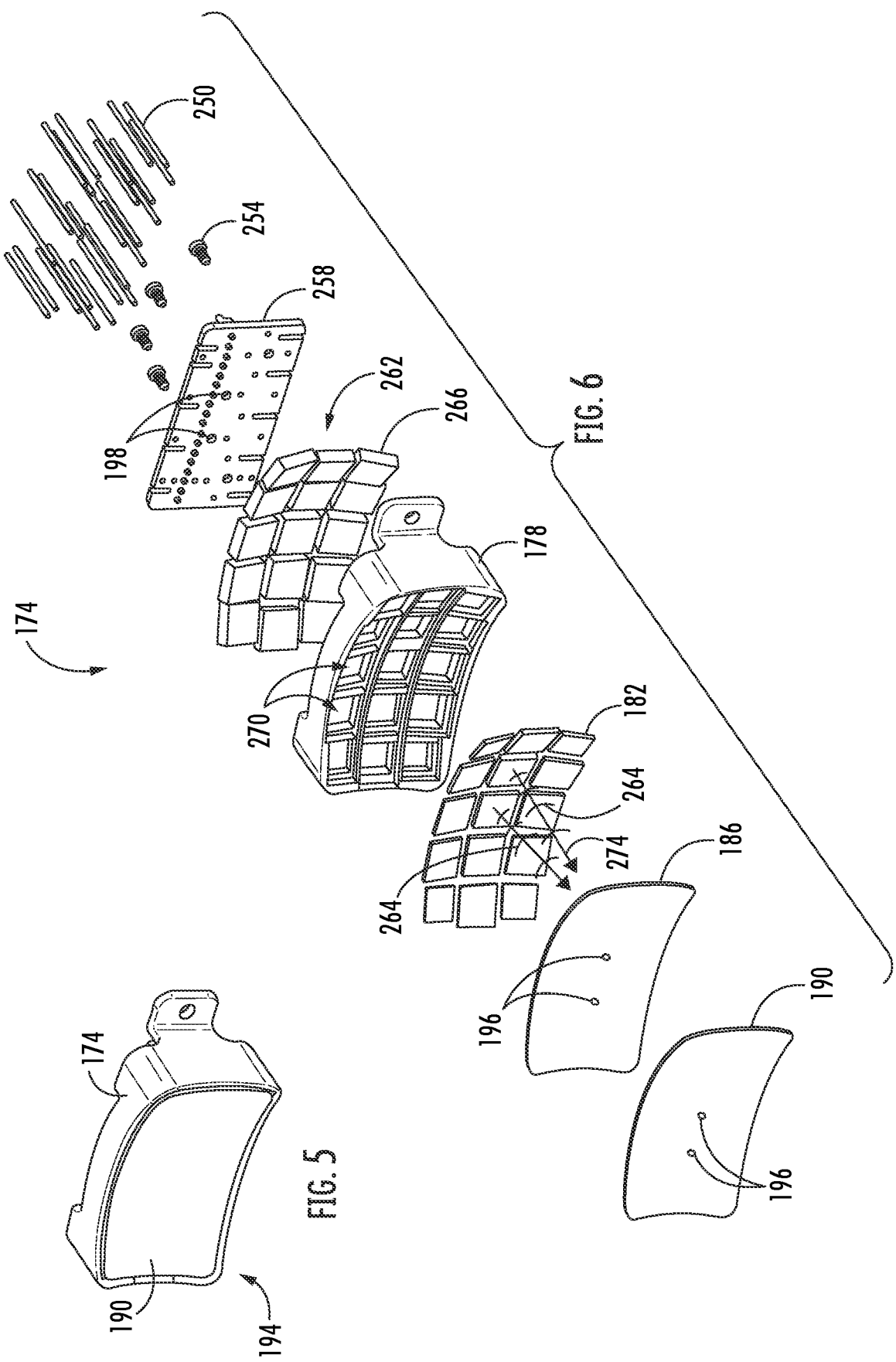

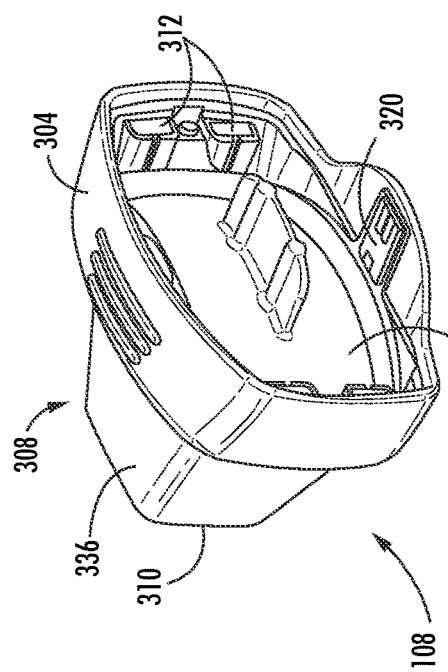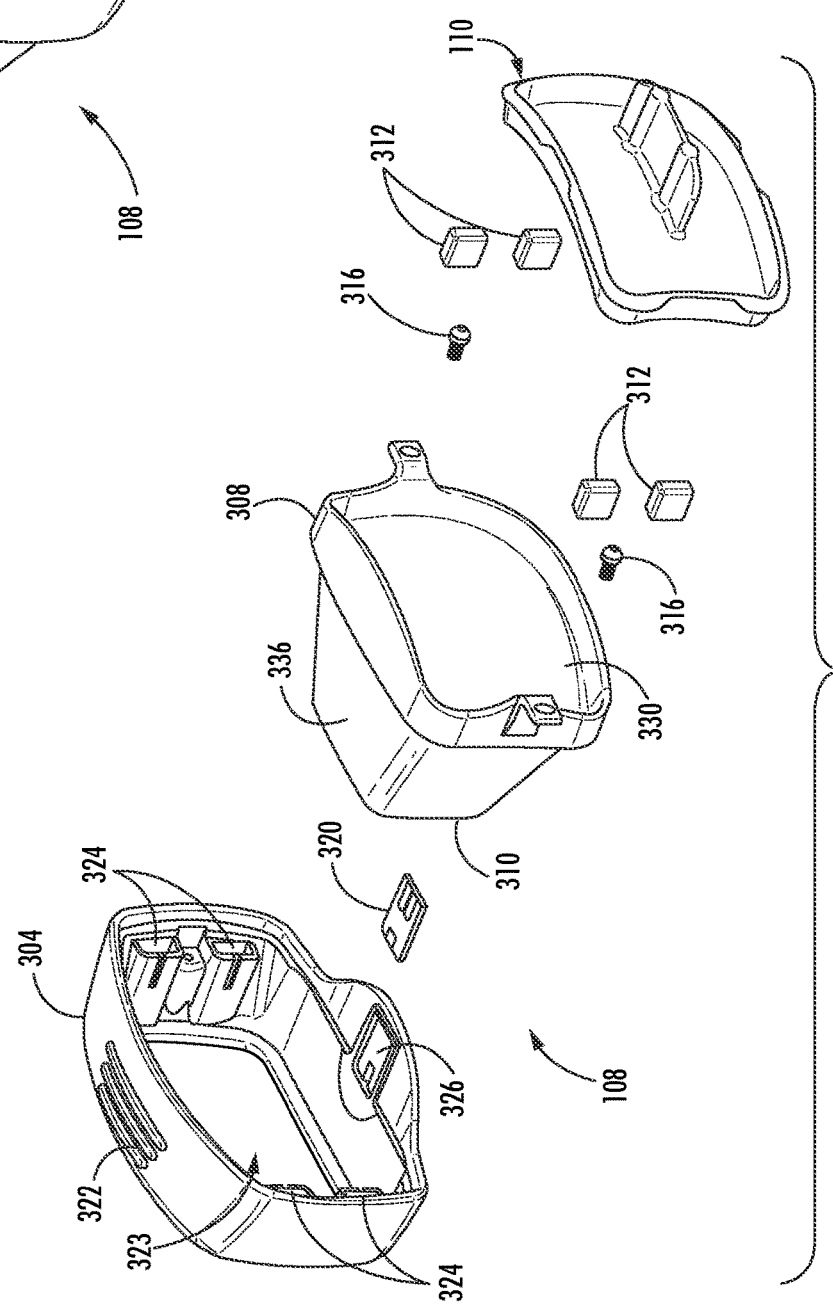

HANDHELD FOCUSED EXTRACORPOREAL SHOCK WAVE THERAPY DEVICE, KIT, AND METHOD

This application claims the benefit of priority of (i) U.S. provisional application Ser. No. 63/263,102, filed on Oct. 27, 2021, and (ii) U.S. provisional application Ser. No. 63/267,048, filed on Jan. 22, 2022, the disclosures of which are herein incorporated by reference in their entirety.

FIELD

This disclosure relates to the field of extracorporeal shock wave therapy (ESWT) and, in particular, to a handheld focused ESWT device (an f-ESWT device) that produces a high energy shock wave and is battery-powered.

BACKGROUND

Extracorporeal shock wave therapy uses shock waves as a non-invasive approach for treating certain medical conditions, such as wounds (e.g., diabetic foot ulcers), orthopedic injuries (e.g., plantar fasciitis), skin aesthetics (e.g., facial wrinkles), and men's urological disorders (e.g., erectile dysfunction). F-ESWT is also used to treat wounds and orthopedic conditions in veterinary applications for equine and smaller animals including companion animals. The shock waves used in f-ESWT are sound waves. In particular, the shock waves are short duration, acoustic pulses having a very high positive pressure amplitude and a steep pressure increase compared to the ambient pressure. Shock waves are similar to ultrasound but have a different wave profile. Typically, ultrasound waves have a periodic oscillation between positive and negative pressure along with a narrow bandwidth. Whereas, shock waves typically exhibit a single positive pressure pulse containing a broad bandwidth. Moreover, "focused" shock waves can place therapeutic energy at specified depths in the tissue (i.e., below the skin) depending on the medical protocol requirements. Focused ESWT is sometimes designated as f-ESWT, where the "f" stands for focused. Lastly, shock waves are different than radial pressure pulses due to their higher pressure, faster rise time, shorter duration, and ability to be focused. Radial pressure waves are not shock waves and cannot be focused. Instead, radial pressure waves have a maximum pressure at the skin surface and are dispersed in the tissue away from the applicator tip of the corresponding device.

When a shock wave is applied to the patient during f-ESWT, it induces a biological healing reaction in the body tissue that is useful in treating the above-mentioned medical conditions. Shock wave therapy is painless and has a very low incidence of side effects.

Known f-ESWT devices generate shock waves using electrohydraulic, piezoelectric, or electromagnetic shock wave generators. Each type of known f-ESWT device is expensive, large, unwieldy, and difficult to operate. For example, known f-ESWT devices typically include a trolley-mounted base unit operatively connected to a transducer handpiece by a robust electrical cable. The base unit houses control electronics and power electronics for generating the shock waves. These types of f-ESWT devices operate at very high voltage levels in the multi-kilovolt range. The base unit requires a connection to an AC wall outlet for a supply of electricity in order to generate the shock waves. The transducer handpiece is applied to the patient and receives signals from the base unit for generating the shock waves. The transducer handpiece does not include any electronics for generating the high voltage pulse used to generate the shock waves. Instead, the high voltage pulse is generated by the base unit using electrical power from the AC wall outlet, transmitted along the connecting electrical cable, and then received by the handpiece.

Based on the above, known f-ESWT devices are unsuitable for battery-powered operation because a connection to an AC wall outlet is required to generate the high voltage pulse required for activating the transducers of the transducer handpiece. Accordingly, improvements are desired to known f-ESWT devices by increasing the portability of f-ESWT devices, reducing the cost of f-ESWT devices, and simplifying the operation of f-ESWT devices.

SUMMARY

According to an exemplary embodiment of the disclosure, a focused extracorporeal shock wave therapy (f-ESWT) device includes a handheld housing, a battery, and a transducer assembly. The battery is located in the handheld housing. The transducer assembly is located in the handheld housing and is operably connected to the battery. The transducer assembly is configured to generate a focused shock wave using electrical energy from the battery.

According to another exemplary embodiment of the disclosure, a focused extracorporeal shock wave therapy (f-ESWT) kit includes a handheld f-ESWT device and a plurality of standoff structures. The handheld f-ESWT device includes (i) a handheld housing, (ii) a rechargeable battery located in the handheld housing, and (iii) a transducer assembly located in the handheld housing and operably connected to the rechargeable battery. The transducer assembly is configured to generate, using electrical energy from the rechargeable battery, a plurality of individual shock waves that combine to form a focused shock wave. Each standoff structure is configured for removable connection to the handheld housing of the f-ESWT device, and each standoff structure is configured to transmit the plurality of individual shock waves when removably connected to the handheld housing of the f-ESWT device. Moreover, in one embodiment, each standoff structure is configured to transmit the focused shock wave at a predetermined focal depth when connected to the handheld housing. The predetermined focal depth may be different for each standoff structure of the plurality of standoff structures.

According to yet another exemplary embodiment of the disclosure, a method of generating a focused shock wave using a handheld extracorporeal shock wave therapy device includes supplying a transducer assembly with electrical energy from a battery operably connected to the transducer assembly. The transducer assembly and the battery are located in a handheld housing. The method further includes generating a plurality of individual shock waves with a plurality of piezoelectric elements of the transducer assembly using the electrical energy from the battery. The individual shock waves of the plurality of individual shock waves combine to form the focused shock wave.

BRIEF DESCRIPTION OF THE FIGURES

The above-described features and advantages, as well as others, should become more readily apparent to those of ordinary skill in the art by reference to the following detailed description and the accompanying figures in which:

FIG. 5 illustrates a piezoelectric transducer assembly of the f-ESWT device;

FIG. 6 illustrates an exploded view of the piezoelectric transducer assembly;

FIG. 9 illustrates one of the standoff structures;

FIG. 10 illustrates an exploded view of one of the standoff structures;

DETAILED DESCRIPTION

Figure 1:
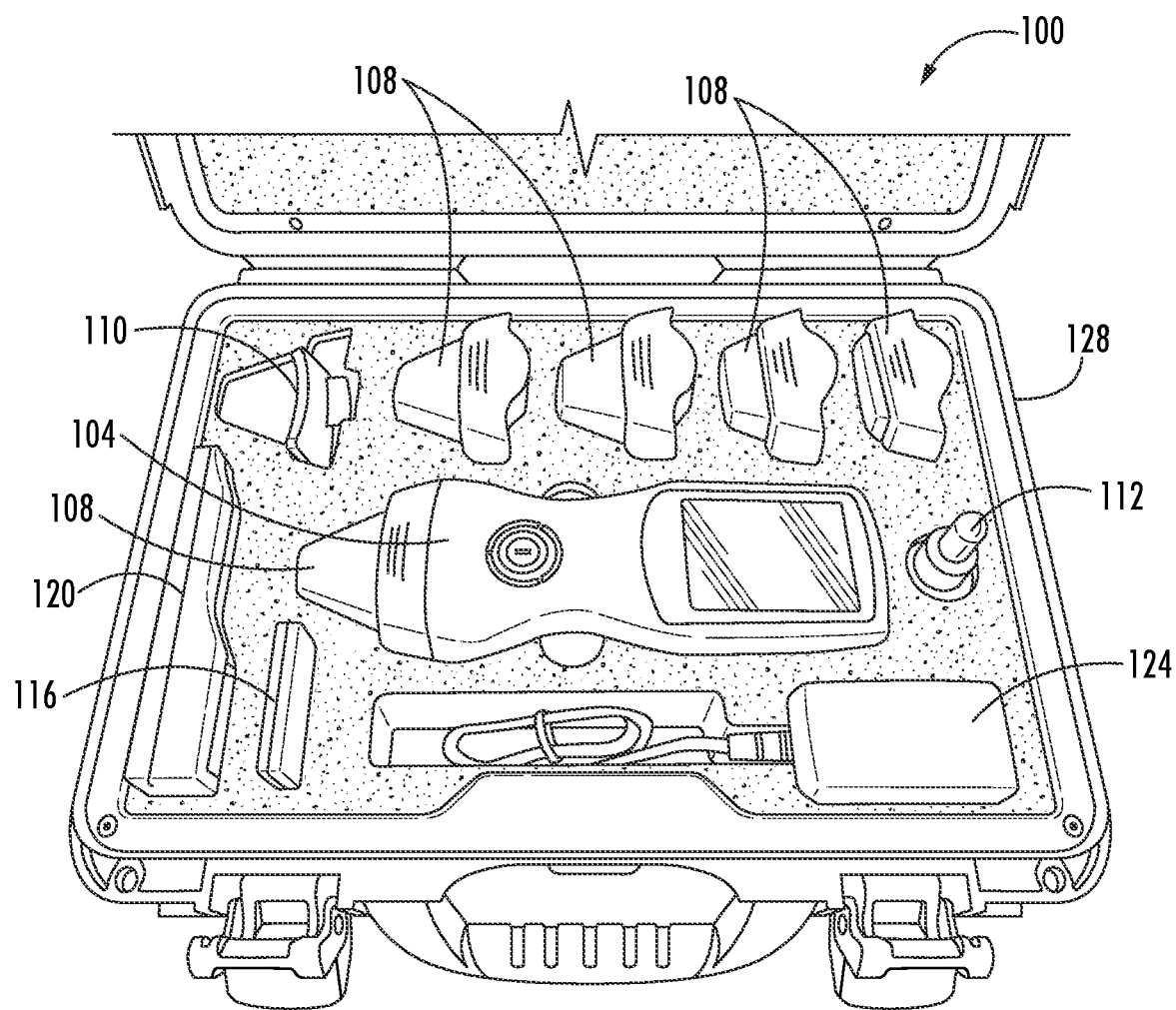
FIG. 1 illustrates an f-ESWT kit, as disclosed herein.

For the purpose of promoting an understanding of the principles of the disclosure, reference will now be made to the embodiments illustrated in the drawings and described in the following written specification. It is understood that no limitation to the scope of the disclosure is thereby intended. It is further understood that this disclosure includes any alterations and modifications to the illustrated embodiments and includes further applications of the principles of the disclosure as would normally occur to one skilled in the art to which this disclosure pertains.

Aspects of the disclosure are disclosed in the accompanying description. Alternate embodiments of the disclosure and their equivalents may be devised without parting from the spirit or scope of the disclosure. It should be noted that any discussion herein regarding "one embodiment," "an embodiment," "an exemplary embodiment," and the like indicate that the embodiment described may include a particular feature, structure, or characteristic, and that such particular feature, structure, or characteristic may not necessarily be included in every embodiment. In addition, references to the foregoing do not necessarily comprise a reference to the same embodiment. Finally, irrespective of whether it is explicitly described, one of ordinary skill in the art would readily appreciate that each of the particular features, structures, or characteristics of the given embodiments may be utilized in connection or combination with those of any other embodiment discussed herein.

For the purposes of the disclosure, the phrase "A and/or B" means (A), (B), or (A and B). For the purposes of the disclosure, the phrase "A, B, and/or C" means (A), (B), (C), (A and B), (A and C), (B and C), or (A, B and C).

The terms "comprising," "including," "having," and the like, as used with respect to embodiments of the disclosure, are synonymous.

As shown in FIG. 1, an f-ESWT kit 100 includes a handheld focused high-energy battery-powered f-ESWT device 104, a plurality of standoff structures 108, a protective cover 110, a container of coupling fluid 112, a battery 116, a battery charger 120, and a power adapter 124 for the battery charger 120, each of which is housed in a corresponding case 128. The f-ESWT kit 100 is a self-contained portable f-ESWT solution that generates high-energy focused shock waves 354 (FIG. 11) at a desired focal depth 356 (FIG. 11) based on the selected standoff structure 108. The f-ESWT device 104 is whisper-quiet, battery-powered, and includes no separate base unit or wired connection to any other device or power source. Each element of the f-ESWT kit 100 is described followed by a description of the electrical operation of the f-ESWT device 104.

The f-ESWT Device

Figure 2A:
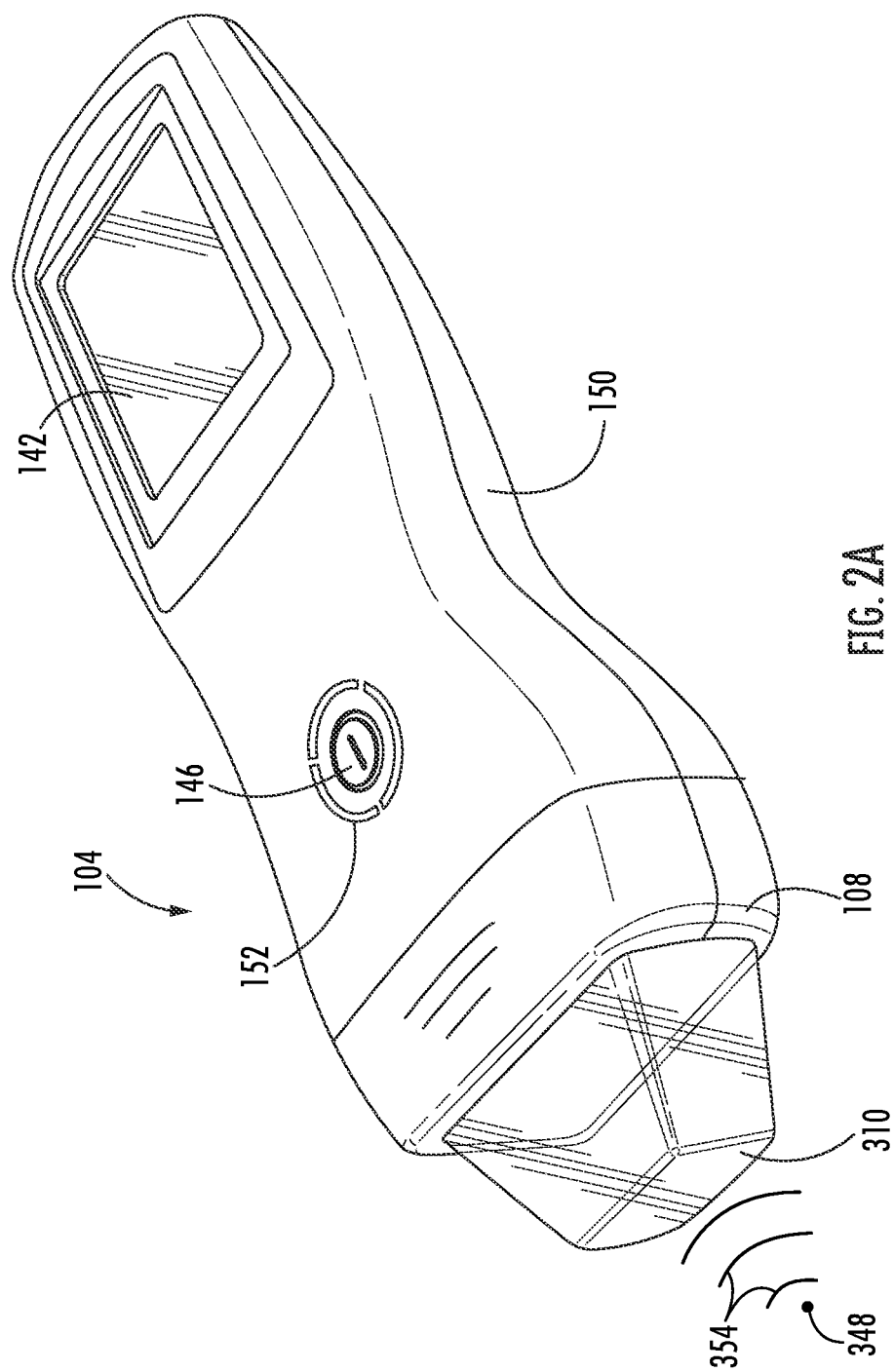
FIG. 2A illustrates an f-ESWT device of the f-ESWT kit of FIG. 1.

The f-ESWT device 104 is shown in FIG. 2A with a selected standoff 108 structure connected thereto. The f-ESWT device 104 includes a handheld housing 150 that supports a touch screen 142 and an operating button 146. The housing 150 is contoured for easy grasping by a clinician with one hand. The f-ESWT device 104 is completely portable, configured for one-hand operation, and is light enough for any person to operate. In one embodiment, the f-ESWT device 104 weighs less than thirteen ounces. The handheld housing 150 is disconnected from electrical energy sources external to the handheld housing 150 when the f-ESWT device 104 generates the focused shock wave 354. External energy sources include wall outlets having a supply of mains power and/or AC power, for example. External energy sources also include electrical energy sources that are connected to the f-ESWT device 104 with a cord, such as a base unit, a transformer, a switching power supply, and/or a remote battery. The f-ESWT device 104 is a compact, hand-held, battery-powered f-ESWT product.

Figure 3:
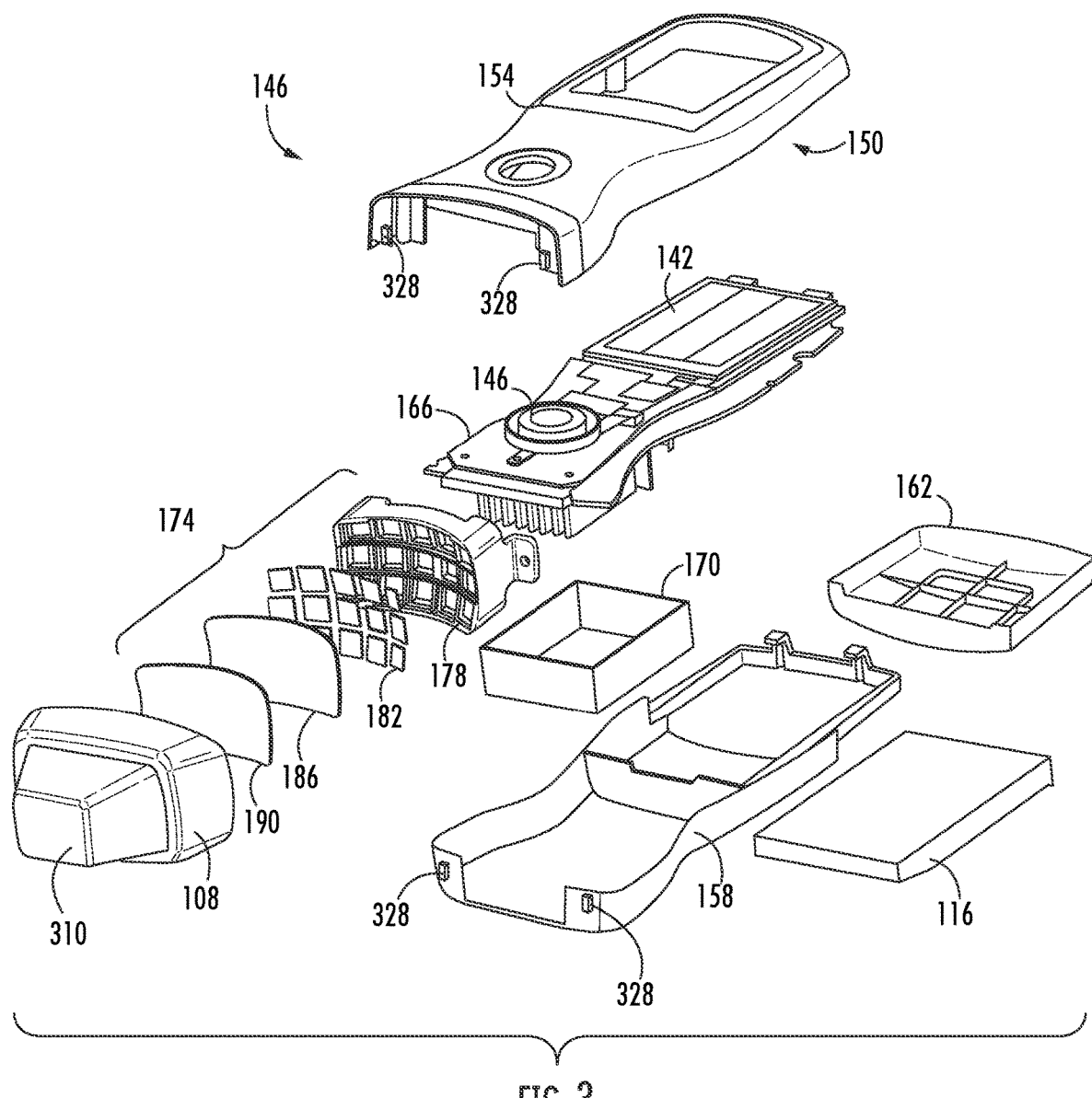
FIG. 3 illustrates an exploded view of the f-ESWT device.

With reference to FIG. 3, f-ESWT device 104 further includes an upper housing part 154, a lower housing part 158, the battery 116, and a battery cover 162. Moreover, the f-ESWT device 104 includes a main control board 166 having a corresponding electromagnetic interference (EMI) can 170, and a piezoelectric transducer assembly 174 including a plurality of shock wave generating elements shown as the piezoelectric elements 182.

The battery 116 is received by the f-ESWT device 104 and is the power source for generating the focused shock waves 354 with the transducer assembly 174. Specifically, the battery 116 is located in the handheld housing 150 of the f-ESWT device behind the battery cover 162. The battery 116 is configured to generate electrical energy that is used to generate the focused shock waves 354. That is, the battery 116 converts chemical energy into electrical energy for generating the focused shock waves 354 with the transducer assembly 174. In one embodiment, the battery 116 is a rechargeable lithium-ion battery. In other embodiments, any other rechargeable or non-rechargeable battery having a high power density may be provided.

The battery charger 120 (FIG. 1) is configured to recharge the battery 116. The battery charger 120 receives power from the power adapter 124 (FIG. 1), which is configured for connection to a wall outlet supply of electricity (not shown) to receive a supply of AC power. In one embodiment, the battery 116 is removed from the housing 150 and is electrically connected to the battery charger 120 during charging of the battery 116. Neither the battery charger 120 nor the power adapter 124 is connected to the housing 150 during the generation of the focused shock waves 354.

Figure 4:
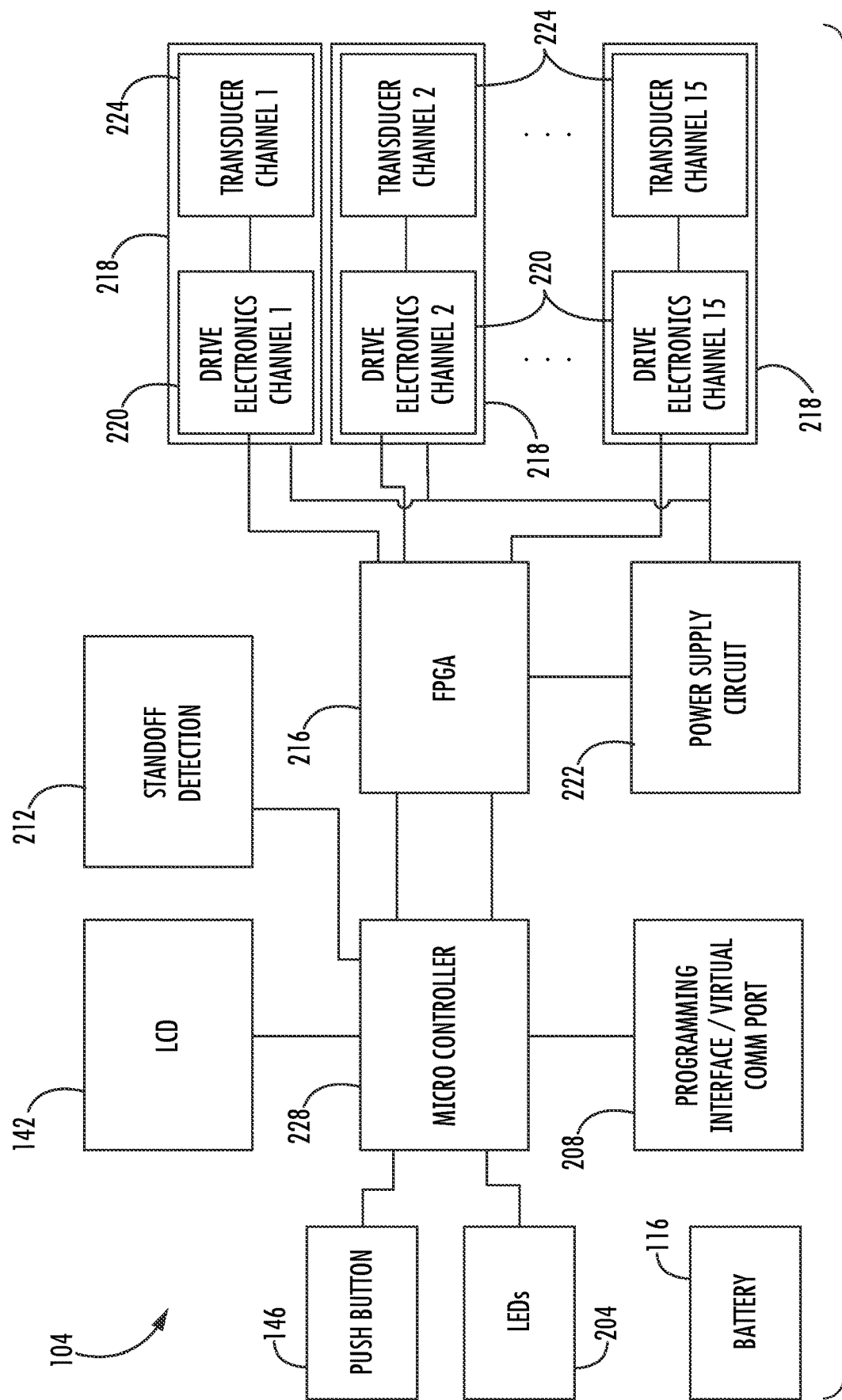
FIG. 4 is a block diagram of the f-ESWT device.

With reference to the block diagram of FIG. 4, the f-ESWT device 104 includes a touchscreen 142, the operating button 146, light-emitting diodes (LEDs) 204, a programming interface 208, a standoff detection module 212, a field programmable gate array (FPGA) 216, a plurality of driver circuits 218, and a power supply circuit 222 each operatively connected to a microcontroller 228 and the battery 116.

Figure 2B:
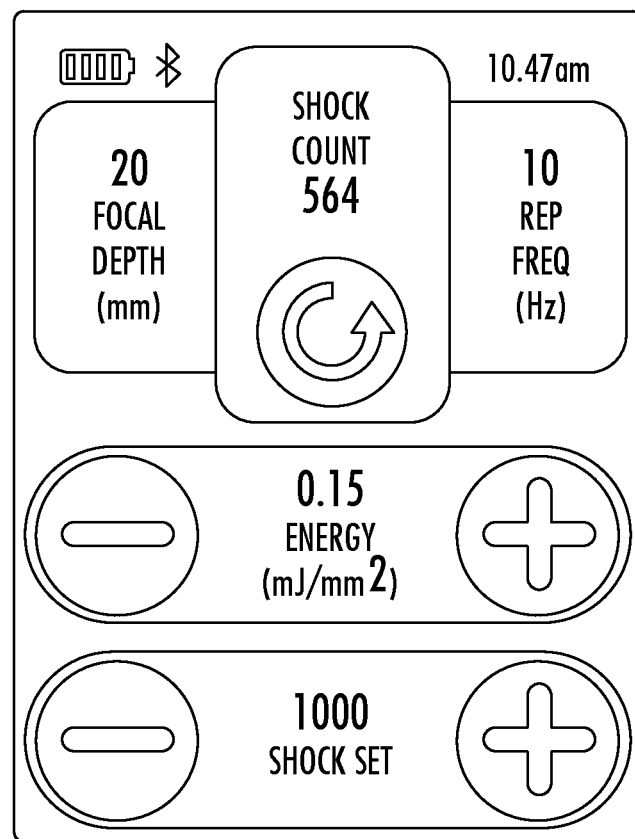
FIG. 2B illustrates a graphical user interface of the f-ESWT device.

The touchscreen 142 is configured to receive user inputs and to display a graphical user interface (GUI) (shown in FIG. 2B). The touchscreen 142 includes a touch-sensitive input device overlaid upon a display screen, such as a liquid crystal display (LCD) screen. The touchscreen 142 receives user inputs and generates corresponding input data. The touchscreen 142 is connected to the microcontroller 228 via a parallel interface and is mounted on the housing 150. The GUI is configurable to show a plurality of soft buttons for controlling and configuring the f-ESWT device 104.

With reference to FIG. 2B, in one embodiment, the touchscreen 142 enables the clinician and/or operator of the f-ESWT device 104 to select an energy flux density of the generated focused shock waves 354 and to select a predetermined number of focused shock waves 354 to be included in a shock set for a particular treatment area based on user inputs received by the touchscreen 142. Specifically, the touchscreen 142 receives first user inputs corresponding to the energy flux density and second user inputs corresponding to the predetermined number of focused shock waves 354 to be included/generated. In an exemplary embodiment, the selected energy flux density is 0.15 mJ/mm$^2$ and one thousand focused shock waves 354 are included in the shock set. The predetermined number of the focused shock waves 354 included in the shock set ranges from one to five thousand.

The GUI displayed by the touchscreen 142 is also configured to display data corresponding to a graphical representation of a predetermined repetition frequency, data corresponding to the energy level of the focused shock waves 354 (i.e. the energy flux density), and data corresponding to the number of the focused shock waves 354 generated by the transducer assembly 174. The GUI also displays a graphical representation of the focal depth 356 of the connected standoff structure 108, the predetermined number of the focused shock waves 354 generated in the current shock set (i.e., the "shock count"), and the predetermined repetition frequency at which the focused shock waves 354 are generated during the treatment process in hertz (i.e., the "REP FREQ"). In the illustrated example, the focused shock waves 354 are generated at 10 Hz, in other embodiments, the predetermined repetition frequency ranges from 1 Hz to 100 Hz. The touchscreen 142 may also be configured to display the time of day, the remaining charge of the battery 116, and the wireless connection state to any external devices (not shown), such as a Bluetooth® connection to a personal or tablet computer, for example. In one embodiment, the touchscreen is a 2.8 inch (71 mm) capacitive touch-sensitive TFT display.

As shown in FIG. 2A, the operating button 146 is mounted on the housing 150 and is operably connected to the microcontroller 228. The operating button 146 is surrounded by an illuminated ring 152, in one embodiment. The operating button 146 is configurable in a first state and a second state, and is configured to generate input data when touched by the clinician. An exemplary first state is a first press and release of the operating button 146 by the clinician, and an exemplary second state is a second press and release of the operating button 146 by the clinician. The operating button 146 is configured to be pressed by the clinician to cause the microcontroller 228 to start and stop the generation of the focused shock waves 354. In one embodiment, when the button 146 is pressed once (the first state), the focused shock waves 354 of the current shock set are generated at the drive voltage pulse repetition frequency, and the shock count is incremented, and when the button 146 is pressed a second time (the second state), generation of the focused shock waves 354 is stopped, etc.

As shown in FIG. 4, the programming interface 208 of the f-ESWT device 104 is provided as one or more ports for connecting the f-ESWT device 104 to an external electronic device such as a personal computer (not shown). The programming interface 208, in one embodiment, is a serial interface to the microcontroller 228. The programming interface 208 enables a clinician to configure the f-ESWT device 104 and to configure the FPGA 216. For example, a clinician can connect the f-ESWT device 104 to a personal computer using the programming interface 208 and then program a maximum energy of the focused shock waves 354, a minimum energy of the focused shock waves 354, a maximum focal depth, a minimum focal depth, a maximum number of the focused shock waves 354 in the shock set, a minimum number of the focused shock waves 354 in the shock set, a maximum shock wave repetition frequency at which the focused shock waves 354 are generated, and a minimum shock wave repetition frequency at which the focused shock waves 354 are generated. Moreover, using the programming interface 208, the clinician can program a maximum number of shock sets within a predetermined time period. In one embodiment, for example, the f-ESWT device 104 can be limited to delivering one shock set every twelve hours. Such an approach configures the f-ESWT device 104 for safe usage by a patient that has been instructed how to apply the focused shock waves 354 to themselves or to someone else. The programming interface 208 also enables the FPGA 216 to be configured to adjust time delays 396 (FIG. 17) sent to the piezoelectric elements 182, as described in detail herein.

As shown in FIG. 4, the standoff detection module 212 is configured to detect the specific standoff structure 108 that is connected to the housing 150 of the f-ESWT device 104. In one embodiment, each standoff structure 108 includes an electronic identifier element 320 (FIG. 9), and the standoff detection module 212 detects a value from the electronic identifier element 320 to identify the particular standoff structure 108 connected to the housing 150.

In FIG. 4, the FPGA 216 is operably connected to the microcontroller 228, the driver circuits 218, and the power supply circuit 222. In an exemplary embodiment, the FPGA 216 is serially connected to the microcontroller 228 via a serial interface. In other embodiments, any type of suitable electrical connection protocol is utilized. The FPGA 216 is also referred to herein as a central clocking reference. The FPGA 216 is configured to receive an electronic "fire" signal from the microcontroller 228. The fire signal causes the FPGA 216 to generate a plurality of transducer fire signals that activate the driver circuits 218 for controlling high voltage electrical signals that are supplied to the transducer assembly 174 (FIG. 3) for generating the focused shock waves 354. In one embodiment, the FPGA 216 is configured for a different timing sequence, timing signals, time delays, timing delays, time delay signals, timing delay signals, or timing programs for each of the standoff structures 108 to focus accurately and tightly the focused shock waves 354.

Figure 22:
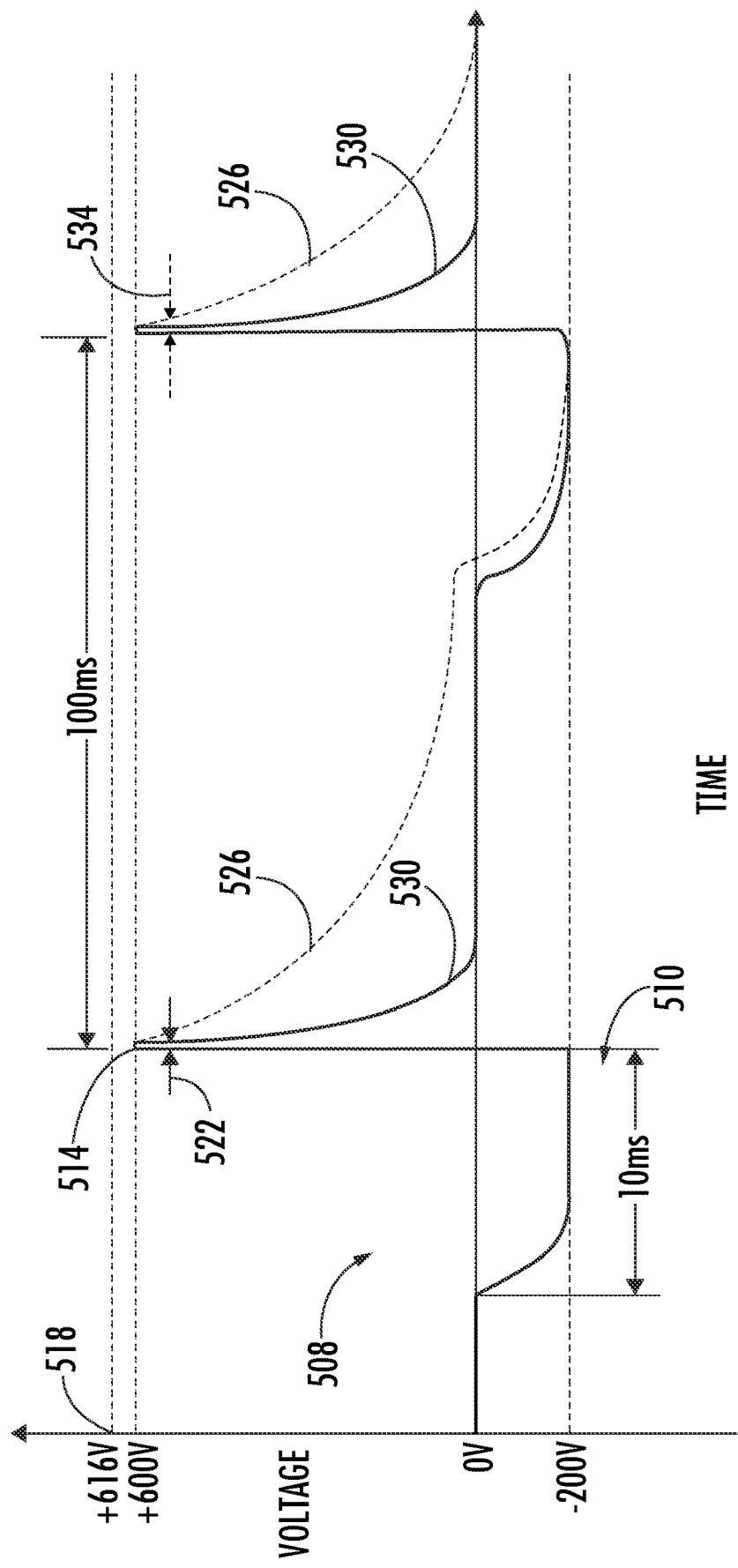
FIG. 22 is a graph illustrating a drive signal applied to the piezoelectric elements of the f-ESWT device to generate a shock wave, two cycles of the drive signal are shown.

As shown in FIG. 4, the driver circuits 218 each include drive channel electronic units 220 and transducer channels 224. The drive channel electronic units 220 control the high voltage and high current signals that are supplied to the transducer assembly 174 for the focused shock waves 354. In one embodiment, the f-ESWT device 104 includes a separate drive channel electronic unit 220 and transducer channel 224 for each piezoelectric element 182 of the transducer assembly 174. In the example illustrated herein, the f-ESWT device 104 includes fifteen driver circuits 218 for the fifteen piezoelectric units 182. In some embodiments, the driver circuits 218 are also referred to as discrete pulse amplifier circuits, high voltage pulse amplifiers, and/or high voltage control units for generating drive voltage pulses 514 (FIG. 22).

The transducer channels 224 operatively connect the drive channel electronic units 220 to the piezoelectric elements 184 of the transducer assembly 174.

In FIG. 4, the power supply circuit 222 is configured to generate (i) the high voltage electrical signals (i.e., the drive voltage pulse 514, FIG. 22) that are supplied to the piezoelectric units 182 for generating the focused shock waves 354, and (ii) high voltage pre-charge electrical signals (i.e., the pre-charge voltage 510, FIG. 22) that are supplied to the piezoelectric units 182 for reducing/managing de-poling of the piezoelectric units 182. The high voltage electrical signals, including the drive voltage pulse 514 and the pre-charge voltage 510, are generated by the power supply circuit 222 with electrical energy from only the battery 116. Accordingly, there is no connection of the f-ESWT device 104 to a source of AC power when generating the pre-charge voltage 510, when generating the focused shock waves 354 with the drive voltage pulses 514, and when treating a patient. In this way, the f-ESWT device 104 is completely portable, wireless, and self-contained. The f-ESWT device 104 is electrically disconnected from any external supply of AC power during the generation of the focused shock waves 354.

As shown in FIG. 4, the microcontroller 228 is provided, in one embodiment, as a 32F413 microprocessor by STMicroelectronics. In other embodiments, the microcontroller 228 is any desired processor, microprocessor, controller, and/or microcontroller. The microcontroller 228 is located in the housing 150 and, as noted, is operably connected to the battery 116 and to the transducer assembly 174 among other components of the f-ESWT device 104.

With reference to FIGS. 5 and 6, the transducer assembly 174, which is located in the handheld housing 150 and is also referred to herein as a piezoelectric shock wave generator assembly, includes a mosaic support frame 178, the plurality of piezoelectric elements 182, a backing layer 262 including backing layer elements 266, first and second acoustical impedance matching layers 186, 190, jumper wires 250, fasteners 254, and an array board 258. The transducer assembly 174 is operably connected to the battery 116 to receive the electrical energy generated by the battery 116. The transducer assembly 174 is modular and detachable from the housing 150 to provide serviceability of the f-ESWT device 104. As described herein, the transducer assembly 174 is configured to generate the focused shock wave 354 using only the electrical energy from the battery 116.

As shown in FIG. 6, the mosaic support frame 178, which is also referred to as an array frame, is located in the housing 150. In one embodiment, the support frame 178 is molded from a thermoplastic material having a high degree of electrical insulating (dielectric) properties. The support frame 178 forms the correct geometry for a desired focal distance 352 (FIG. 11) of the focused shock waves 354. In one embodiment, the support frame 178 defines a corresponding receptacle 270 for each of the piezoelectric elements 182 and the backing layer 262. In the illustrated embodiment, the mosaic support frame 178 includes fifteen of the receptacles 270. The receptacles 270 are oriented in a partially-spherical arrangement. That is, the mosaic support frame 178 supports the piezoelectric elements 182 so that a front surface 176 (FIG. 7) of the piezoelectric elements 182 forms a portion of a sphere. In one embodiment, the receptacles 270 located at the corners of the support frame 178 are smaller than the other receptacles 270. The support frame 178 also contains features to hold the jumper wires 250 and other electrical connections at specified locations on both sides of the piezoelectric elements 182 to aid an assembly process of the transducer assembly 174.

Figure 7:
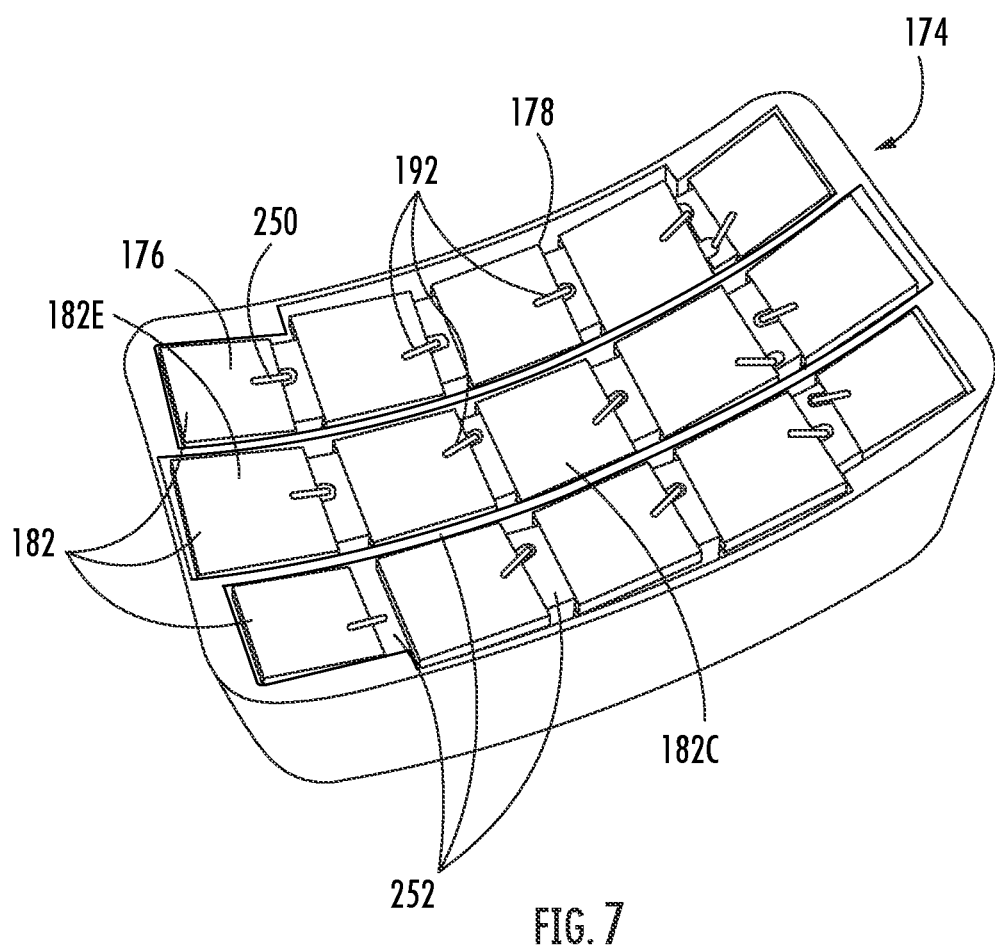
FIG. 7 illustrates a mosaic support frame and piezoelectric elements of the piezoelectric transducer assembly.

With reference to FIGS. 6 and 7, the piezoelectric elements 182 are received by the receptacles 270 and are supported by the mosaic support frame 178. The piezoelectric elements 182 are exemplary transducers included in the f-ESWT device 104 for generating the focused shock waves 354. In an exemplary embodiment, the piezoelectric elements 182 are "recessed" into the receptacles 270, such that a thin wall 252 formed from the material of the support frame 178 surrounds a perimeter of each of the elements 182. The wall 252 provides a high degree of electrical insulation between adjacent piezoelectric elements 182 to avoid voltage breakdown and electrical shorting when operating the transducer assembly 174 to generate the focused shock waves 354. Each piezoelectric element 182 is configured to generate an individual shock wave 264 (FIG. 6) in response to receiving the drive voltage pulse 514 (FIG. 22). In some embodiments, when the piezoelectric elements 182 are mounted in the support frame 178, a complex fluted surface is formed (not shown).

When piezoelectric material, as included in the piezoelectric elements 182, is subject to an applied electric field (such as the drive voltage pulse 514), the piezoelectric material generates a mechanical strain that results in a change in at least one static dimension of the material. This is sometimes referred to as a reverse piezoelectric effect. The change in static dimension exhibited by the piezoelectric elements 182 is very rapid and is used to generate the individual shock waves 264 (FIG. 6).

In one embodiment, the piezoelectric elements 182 are "dice-and-fill" composite piezoelectric material and epoxy having a regular arrangement of vertical columns of piezoceramic material. These elements 182 have higher efficiency (coupling coefficients) and a lower acoustic impedance that is easier to match to water or tissue. Moreover, these elements 182 are distinguished from elements formed from random piezoelectric fibers that do not have an organized arrangement of the piezoelectric material. The vertical columns of piezoelectric material efficiently direct the corresponding shock wave 264 toward the tissue. Additionally, the piezoelectric elements 182, in some embodiments, are constructed using a "soft" piezoceramic material and/or a single crystal piezoelectric material having a high dielectric constant and high coupling coefficients.

As shown in FIG. 7, in one embodiment, the piezoelectric elements 182 located at corners of the support frame 178 are smaller than the other piezoelectric elements 182. For example, the corner piezoelectric elements 182 are 7.6 mm×7.6 mm, and the other piezoelectric elements 182 are 9 mm×9 mm. Different sized piezoelectric elements 182 are used to fit the physical and industrial design of the f-ESWT device 104. That is, the smaller piezoelectric elements 182 at the corners assist in providing the f-ESWT device 104 with a small and portable form factor.

Figure 11:
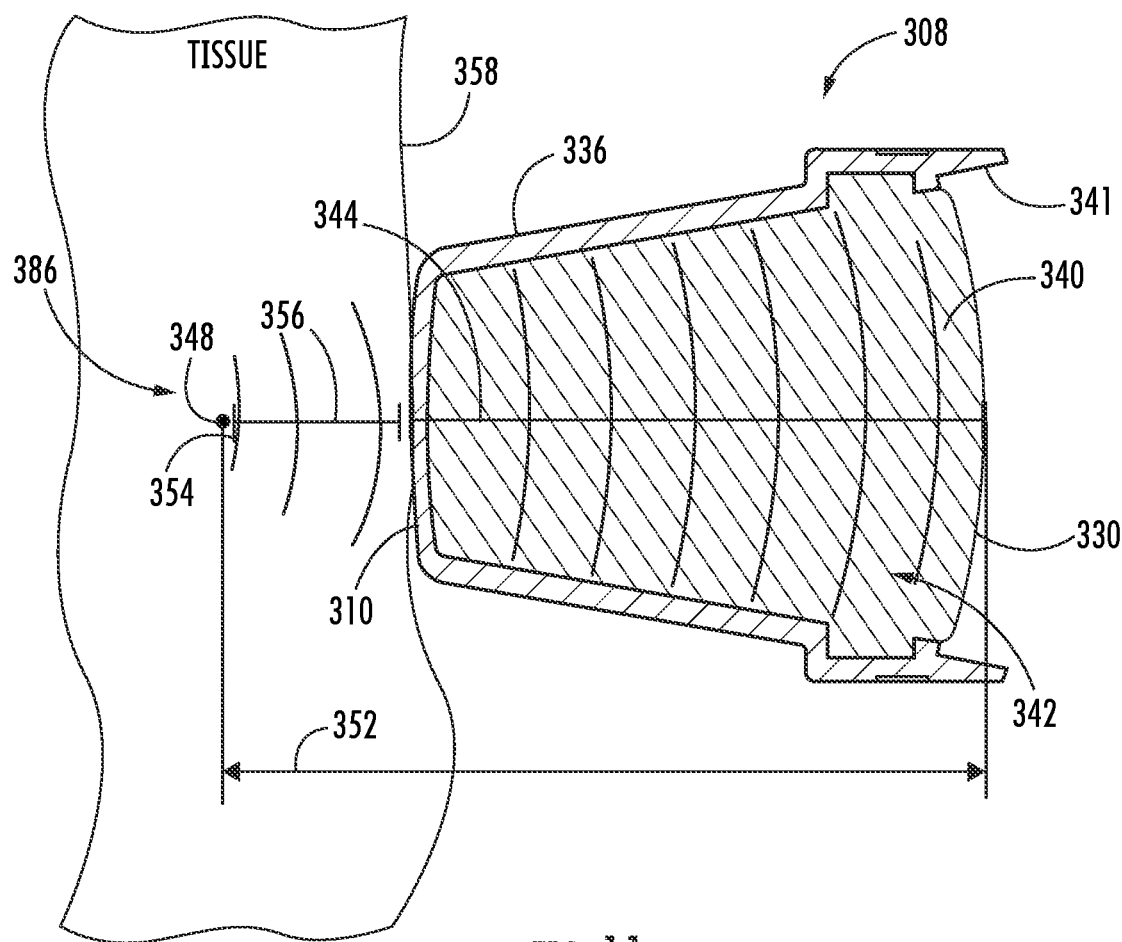
FIG. 11 illustrates a cross-sectional view of a waveguide structure of one of the standoff structures applied to the tissue of a patient at a treatment site.

With reference to FIGS. 6 and 11, since the piezoelectric elements 182 are supported by the support frame 178 in a partially-spherical arrangement and/or orientation, a normal axis (or perpendicular axis) 274 extending from the front surface 176 of the piezoelectric elements 182 meets at a focal point 348 of the focused shock wave 354 that is spaced apart from each of the piezoelectric elements 182 by the focal distance 352. Moreover, the individual shock waves 264 generated from the piezoelectric elements 182, when timed properly, meet at the focal point 348 and constructively combine with each other so that the focused shock wave 354 is generated by the f-ESWT device 104. Accordingly, the mosaic support frame 178 is configured to mechanically focus the individual shock waves 264 from the piezoelectric elements 182 at the focal point 348.

The focal distance 352 (FIG. 11) of the focal point 348 from the piezoelectric elements 182, in one embodiment, is fixed at 50 mm as established by the radius of the partially-spherical arrangement of the piezoelectric elements 182. In the f-ESWT device 104, the focal distance 352 is fixed for each standoff structure 108 and cannot be changed. Moreover, the focal point 348 is fixed at a center axis of the support frame 178. The focal distance 352 is also referred to herein as a "focal length" of the f-ESWT device 104. In other embodiments, the focal distance 352 is from 25 mm to 100 mm, depending on the size and configuration of the mosaic support frame 178.

As shown in FIG. 6, the backing layer 262 is supported by the support frame 178 and includes a plurality of backing layer elements 266. The backing layer elements 266 are each cast into a corresponding receptacle 270 of the mosaic support frame 178, such that the support frame 178 supports the backing layer elements 266. Each backing layer element 266 is located opposite of one of the piezoelectric elements 182. The backing layer 262 is configured to reflect and to direct the individual shock waves 264 generated by the piezoelectric elements 182 towards the matching layers 186, 190 and the connected standoff structure 108. The backing layer elements 266 also provide mechanical damping to the piezoelectric elements 182. In one embodiment, the backing layer elements 266 located at the corners of the backing layer 262 are smaller than the other backing layer elements 266.

An exemplary backing layer 262 is formed from epoxy and/or another suitable material. The backing layer 262 secures the positions of the piezoelectric elements 180 in the support frame 178. For each piezoelectric element 182, the backing layer 262 may extend between the four peripheral edges of the piezoelectric element 182 and the receptacle 170. Depending on the configuration of the support frame 178, the backing layer 262 may be a one-piece structure that includes backing layer element projections instead of the separate backing layer elements 266 shown in FIG. 6. The backing layer 262 is configured to maximize the direct and reflected energy from the piezoelectric elements 182 to the focal point 348, instead of allowing the energy to escape from the rear of the mosaic support frame 178.

In another embodiment, the backing layer 262 is configured to expose a rear surface of at least some of the piezoelectric elements 182 to air, thereby configuring the piezoelectric elements 182 as air-backed transducers. Air provides a huge mismatch in impedance at the back of the piezoelectric elements 182 (even more than epoxy) and tends to send even more of the direct and reflected energy from the piezoelectric elements 182 to the focal point 348.

With reference to FIG. 6, the jumper wires 250 are electrically connected to each of the piezoelectric elements 182 and are configured to supply the piezoelectric elements 182 with electrical signals from the drive channel electronic units 220 via a solder connection. Specifically, a first jumper wire 250 is operably connected to a front side of the piezoelectric element 182, and a second jumper wire 250 is operably connected to a rear side of the piezoelectric element 182. The connection 192 of the jumper wires 250 to the front sides of the piezoelectric elements 182 is shown in FIG. 7. In one embodiment, the jumper wires 250 are soldered to the piezoelectric elements 182 to make the electrical connection thereto. The jumper wires 250 extend through the array board 258 (FIG. 6) and around the backing layer elements 266 to make the electrical connection to the piezoelectric elements 182. The jumper wires 250, in one embodiment, are provided as 30 American Wire Gauge ("awg") wire and are operatively connected to the transducer channels 224 to receive the high power signals from the drive channel electronic units 220.

In one embodiment, the backing layer elements 266 are configured to pot the solder connections between the jumper wires 250 and the piezoelectric elements 182. Accordingly, another benefit of the backing layer 262 is to protect the solder connections between the jumper wires 250 and the piezoelectric elements 182. In one embodiment, the backing layer is formed by pouring liquid epoxy into each of the receptacles 270 from behind the piezoelectric elements 180 after the elements 180 have been soldered to the jumper wires 250. As described above, the receptacles 270 define a partially-spherical surface configuration making adding the backing epoxy 268 manageable, otherwise the liquid uncured backing epoxy 268 would settle to the lowest point.

With reference again to FIG. 6, the first acoustical impedance matching layer 186 is applied to the piezoelectric elements 182, and the second acoustical impedance matching layer 190 is applied to the first acoustical impedance matching layer 186. The transducer assembly 174 is shown in FIG. 7 without the first and second matching layers 186, 190. The matching layer 190 is configured to form a smooth interface 194 for interfacing the transducer assembly 174 with the standoff structure 108 that is connected to the housing 150. Due to the shape of the support frame 178, the interface 194 defines a partially-spherical shape with a specific radius of curvature that is configured to couple easily to the selected standoff structure 108. The interface 194, in one embodiment, is concave. The individual shock waves 264 from the piezoelectric elements 182 are emitted from the partially spherical interface 194.

The materials of the matching layers 186, 190 are selected to transmit the individual shock waves 264 from the piezoelectric elements 182 to the standoff structure 108 with minimal reflection and with minimal attenuation. That is, the matching layers 186, 190 step the acoustical impedance down from the material(s) of the piezoelectric elements 182 to that of water or tissue (which is mostly water) to aid energy transfer of the shock waves 264 and avoid reflections of the shock waves 264. The matching layers 186, 190 consist of composite epoxy and cerium oxide powder having specific mix ratios, in one embodiment. In other embodiments, the matching layers 186, 190 are formed from any other suitable material.

In one embodiment, as shown in FIG. 6, through-holes 196 (also referred to herein as air holes, air openings, and airflow openings) are formed through the matching layers 186, 190 and between the piezoelectric elements 182 to allow air to escape therethrough when the standoff structure 108 is connected to the f-ESWT device 104. The through-holes 196 prevent air bubbles or air pockets from being trapped between the interface 194 and a corresponding interface 330 (FIG. 10) of the selected standoff structure 108. The through-holes are, therefore, configured as an air venting structure. The air passing through the through-holes 196, passes through the support frame 178, through corresponding openings 198 in the array board 258, and into the housing 150. The air is then evacuated from the housing 150 through a corresponding opening (not shown). As shown in FIG. 6, the left through-hole 196 in the matching layer 186 is coaxial with the left through-hole 196 in the matching layer 190, and the right through-hole 196 in the matching layer 186 is coaxial with the right through-hole 196 in the matching layer 190. In another embodiment, the interface 194 is a fluted surface to aid in the evacuation of air from between the interface 194 and the standoff structure 108.

Based on the above, the matching layers 186, 190 are configured to accomplish at least three objectives. First, the matching layers 186, 190 are configured to convert the complex surface defined by the piezoelectric elements 182 and the thin walls 252 of the support frame 178 to a smooth partially-spherical surface that is easily coupled to the standoff structures 108. Second, the matching layers 186, 190 are configured to protect the solder connections between the piezoelectric elements 182 and the jumper wires 250.

Third, the matching layers 186, 190 are configured to step the acoustic impedance down from the high impedance of the piezoelectric material of the piezoelectric elements 182 to the low impedance of tissue or water (i.e., the impedance of the patient), to minimize reflections and increase energy transfer of the shock waves 264. The acoustic impedance of the matching layers 186, 190 is adjusted by adding a specific amount of cerium oxide to the epoxy of the layers 186, 190.

As shown in FIG. 6, the fasteners 254 of the transducer assembly 174 are provided to secure the array board 258 to the support frame 178, thereby fixing the positions of the backing layer elements 266 of the backing layer 262.

The Standoff Structures

Figure 8:
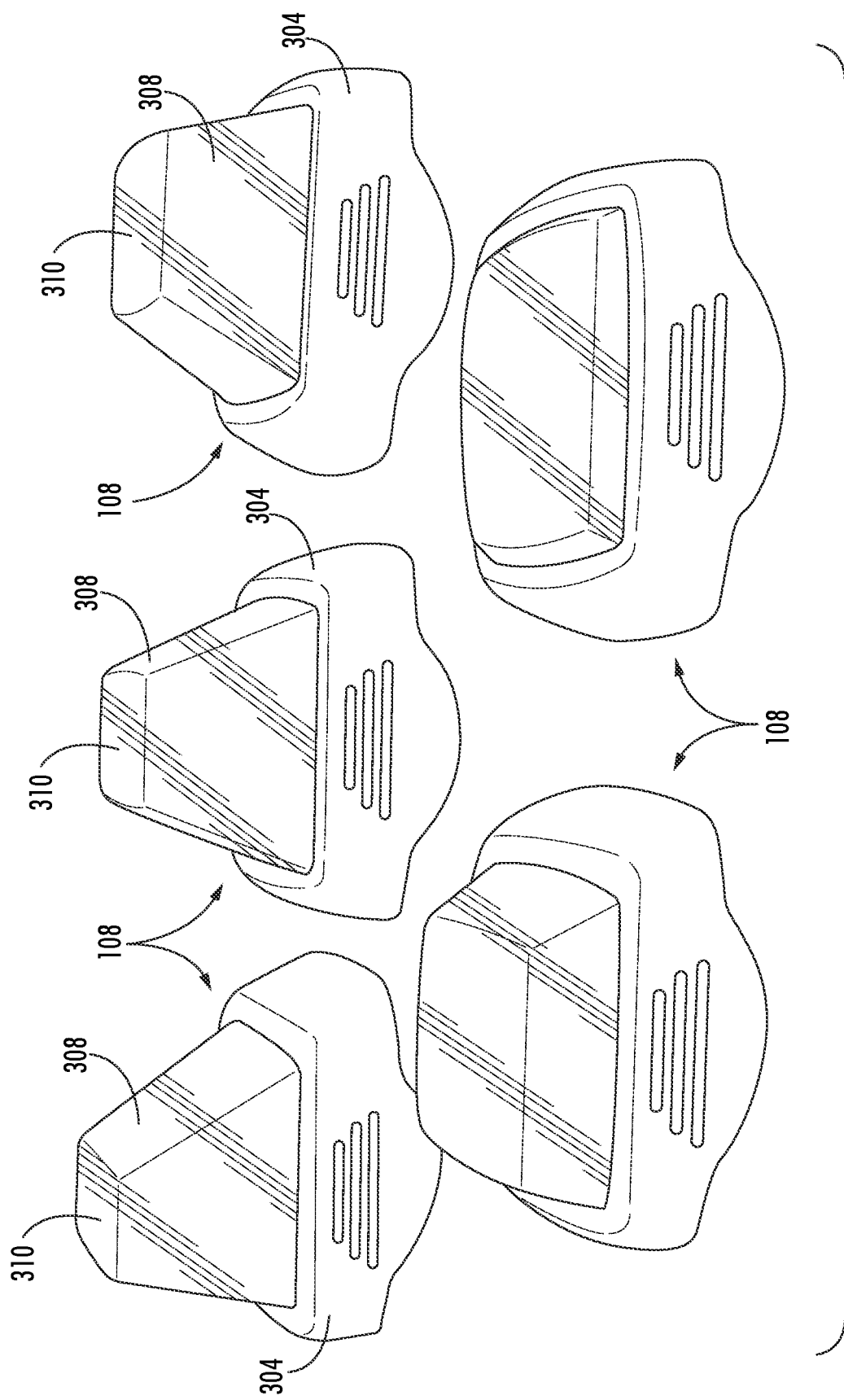
FIG. 8 illustrates a plurality of standoff structures of the f-ESWT kit of FIG. 1.

With reference to FIG. 8, a plurality of the standoff structures 108 are shown. Each standoff structure 108 is removably connectable to the handheld housing 150, and each of the interchangeable standoff structures 108 includes a collar 304 and a waveguide structure 308 defining a treatment surface 310. The treatment surface 310 is applied to the patient during the shock wave therapy session. Each standoff structure 108 has a corresponding focal depth 356 (FIG. 11). In an exemplary embodiment, the f-ESWT kit 100 includes standoff structures 108 having focal depths 356 of 2 mm, 5 mm, 10 mm, 20 mm, and 30 mm. The focal depth 356 is also referred to herein as a treatment depth and/or a tissue penetration distance.

In FIG. 9, the standoff structure 108 is shown with the protective cover 110 applied to the interface surface 330 (FIG. 10) of the standoff structure 108.

As shown in FIG. 10, an exploded view of the standoff structure 108 illustrates the protective cover 110, the collar 304, magnetic elements 312, the waveguide structure 308, fasteners 316, and an electronic identifier element 320.

The collar 304 is configured to removably connect the standoff structure 108 to the housing 150 of the f-ESWT device 104. The collar 304 defines a grip surface 322, a main opening 323, several magnet recesses 324, and an identifier recess 326. The collar 304 is formed from injection molded thermoplastic and/or another suitable material. In one embodiment, the focal depth 356 of the standoff 108 is printed and/or otherwise visually identified on the collar 108, as shown in FIG. 1.

The magnetic elements 312, which are also referred to herein as magnets, are mounted on the collar 304. In particular, the magnetic elements 312 are permanently affixed to the collar 304 and are received in the corresponding magnet recesses 324. The magnetic elements 312 are configured to magnetically couple to corresponding magnetic elements 328 (FIG. 3) mounted on the housing 150 to removably connect the standoff structure 108 to the f-ESWT device 104.

As shown in FIG. 10, the grip surface 322 includes a textured portion of the collar 304 that is convenient for the clinician to grip when separating the standoff structure 108 from the housing 150.

With reference to FIG. 11, the waveguide structure 308 is shown in cross-section and includes a rigid exterior shell 336 surrounding an acoustic gel-based elastomer interior 340. In one embodiment, both the exterior shell 336 and the elastomer interior 340 are transparent and/or clear to allow the clinician to view the skin surface 358 above or at the treatment site 386 therethrough. The treatment site 386 is "internally" located and, therefore, is located below the skin surface 358. The waveguide structure 308 receives the individual shock waves 264 from the transducer assembly 174 and transmits the shock waves 264 therethrough, typically to the patient receiving treatment. The focused shock wave 354 is emitted from the waveguide structure 308, penetrates the skin surface 358, and travels through the tissue to the internally located focal point 348 at the treatment site 386. In other embodiments, the treatment site 386 is topical or nearly topical and the focal depth 356 is adjusted accordingly by selecting an appropriate standoff structure 108. In another embodiment, at least one of the exterior shell 336 and the elastomer interior 340 are translucent or opaque.

The exterior shell 336 defines an opening 341 and a shell space 342 for receiving the elastomer interior 340. The exterior shell 336 is mounted on the collar 304 by the fasteners 316. In one embodiment, the rigid exterior shell 336 is plastic and is formed from TPX (polymethylpentene (PMP)). The TPX treatment surface 310 of the exterior shell 336 is located opposite the opening 341. The treatment surface 310 is rigid and smooth and glides well against the skin especially when a water-based couplant is used. Moreover, the exterior shell 336 formed from TPX is optically transparent and has acoustical properties conducive to transmitting the focused shock wave 354, because the acoustic impedance of TPX is similar to water and the attenuation is very low compared to other polymers. Human and animal tissue is mostly water; accordingly, the acoustic impedance of TPX is well matched to human and animal tissue for transmitting the focused shock wave 354 into the tissue of the patient.

The acoustic gel-based elastomer interior 340 of the waveguide structure 308 is at least partially located in the shell space 342 exterior shell 336 and has a low attenuation to shock wave energy (i.e., acoustical energy). In one embodiment, the elastomer interior 340 is formed from styrene-ethylene-butylene-styrene SEBS gel polymer. The opening 341 of the exterior shell 336 exposes a partially spherical interface surface 330 of the elastomer interior 340.

The interface surface 330 is flexible and elastomeric, and conforms to the shape of the interface 194 of the f-ESWT device 104. The interface surface 330 is convex, in one embodiment. The elastomer interior 340 including the interface surface 300 is squishy and soft. The elastomer interior 340 is resilient and is configured to recoil and/or spring back to its original shape after being contacted. The interface surface 194 is rigid.

The interface surfaces 194, 330 are correspondingly shaped to fit substantially completely against each other for optimal transfer of the individual shock waves 264 through the waveguide structure 308. In one embodiment, as noted, the interface surfaces 194, 330 are formed as a portion of a sphere and correspond in shape to the arrangement of the piezoelectric elements 182. Moreover, in one embodiment, the through-holes 196 enable the evacuation of air so that the interface surface 330 of the elastomeric interior 340 is easily positioned directly against the interface surface 194 of the housing without trapping air therebetween during connection of the standoff structure to the housing.

Both the exterior shell 336 and the elastomer interior 340 of the waveguide structure 308 have a low attenuation to ultrasound and a sound speed and acoustic impedance similar to tissue and/or water, to ensure that the energy produced by the individual shock waves 264 of the piezoelectric elements 182 is transferred to the focal point 348 in the tissue. A large mismatch in the acoustic impedance between the waveguide structure 308 and the tissue would result in a reflection of the focused shock wave 354. High attenuation in the elastomer interior 340 would convert much of the acoustic energy of the focused shock wave 354 into heat energy. Lastly, a large mismatch in sound speed between the waveguide structure 308 and tissue would cause the focused shock wave 354 to refract at the interface between the treatment surface 310 and the patient and cause the shock wave 354 to miss the desired focal point 348. The standoff structure 108 avoids each of these issues.

During construction of the standoff structure 108, the elastomer interior 340 is degassed and compression molded into the shell space 342 defined by the exterior shell 336 to a shape that matches the interface 190. Degassing prevents air bubbles from forming in the elastomer interior 340 and prevents air bubbles between the exterior shell 336 and the elastomer interior 340.

FIG. 11 illustrates a length 344 of the standoff structure 108, the fixed focal distance 352, the location of the focal point 348 of the focused shock wave 354, and the focal depth 356. The focal point 348 is located below a skin surface 358 of the patient. The focal depth 356 is a distance between the treatment surface 310 of the standoff structure 108 and the focal point 348. Accordingly, the 10 mm standoff structure 108 places the focal point 348 of the focused shock wave 354 at 10 mm below the surface 358 of the patient's tissue. The focal depth 356 is inversely related to the length 344 of the standoff structure 108.

Because the exterior shell 336 is rigid, the focal point 348 is located precisely in the tissue in contrast to known flexible and/or compliant standoffs that deform and place the focal point at uncontrolled locations in tissue. Moreover, during treatment sessions in which the treatment surface 310 is positioned against the tissue of the patient, the exterior shell 336 retains its shape and does not bend, flex, or move relative to the housing 150. As such, the rigid exterior shell 336 ensures that the focal point 348 remains at the focal distance 356 from the treatment surface 310, thereby ensuring that the patient receives the focused shock wave 354 at the prescribed treatment depth. Prior art units including a flexible standoff do not provide the same benefits and do not provide the patient with consistent treatment depths.

With reference again to FIG. 10, the electronic identifier element 320 is mounted in the identifier recess 326 of the collar 304. Each standoff structure 108 includes an identifier element 320 with a different electrical value, such as an electrical resistance. The identifier element 320 uniquely identifies the focal depth 356 of the connected standoff structure 108 to the f-ESWT device 104. The electrical value of the identifier element 320 is detected by the standoff detection module 212 when the standoff structure 108 is connected to the housing 150. In one embodiment, the identifier element 320 includes and/or is configured as a surface mount resistor (SMT resistor).

Figure 17:
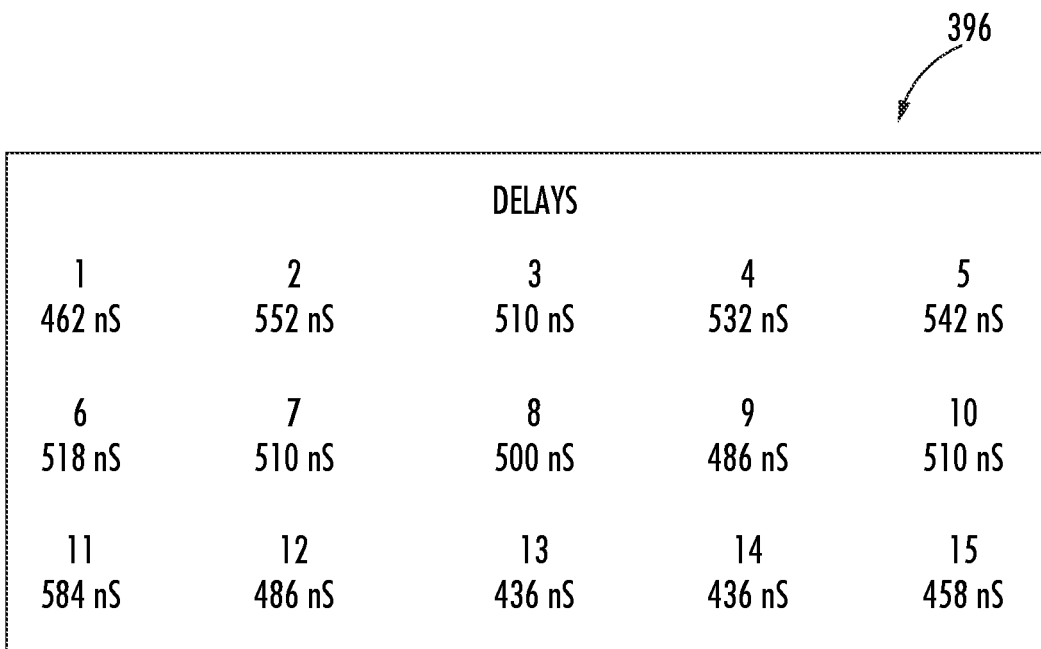
FIG. 17 is an illustration of a display screen of a test device (i.e., a benchtop pulser) showing fifteen time delays applied to the piezoelectric elements of the f-ESWT device.

In another embodiment, the identifier element 320 is provided as a radio frequency identification chip (RFID) or a more advanced integrated circuit (IC) having a memory to store focal depth data and/or timing information corresponding to the time delays 396 (FIG. 17).

Electric Circuits for Generating the Focused Shock Wave

Figure 14:
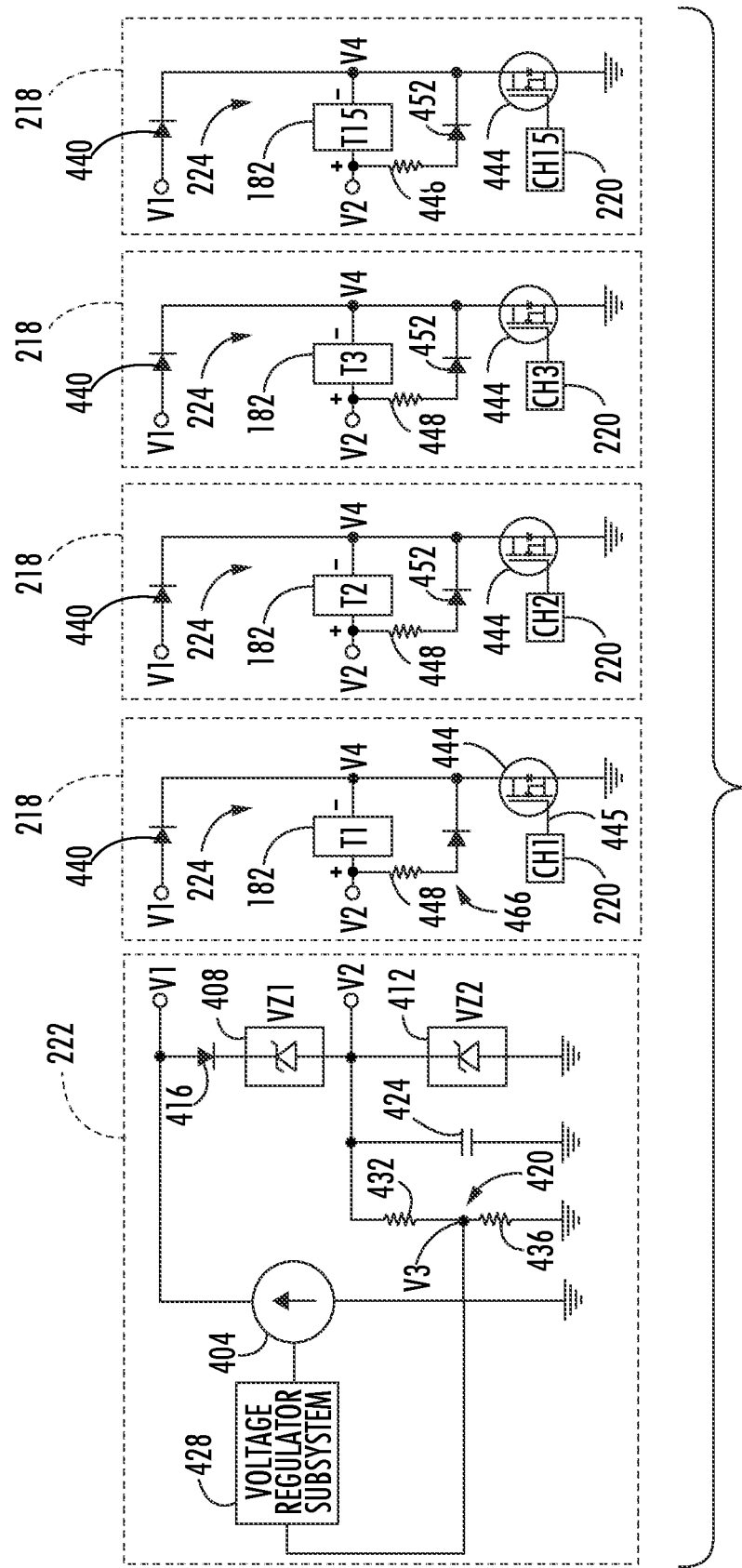
FIG. 14 is a schematic of a power supply circuit and a plurality of driver circuits of the f-ESWT device.

With reference to FIG. 14, an exemplary embodiment of the power supply circuit 222 and the plurality driver circuits 218 are illustrated. The f-ESWT device 104 typically includes one of the driver circuits 218 for each of the piezoelectric elements 182. Only four of the fifteen driver circuits 218 are shown in FIG. 14.

The exemplary embodiment of the power supply circuit 222 includes a current source 404, a first voltage clamp 408, and a second voltage clamp 412. The power supply circuit 222 also includes a diode 416, a voltage divider 420, a capacitor 424, and a voltage regulator subsystem 428. The power supply circuit 222 is a single common high voltage power supply shared by all of the piezoelectric elements 182 and all of the driver circuits 218.

The current source 404, in one embodiment, is a DC current source configured to output a DC current having a maximum output voltage of up to 1000 V (1 kV). A predetermined magnitude of current output from the current source 404 is selectable from zero to five milliamps (0-5 mA). The current source 404, in one embodiment, is formed by an inductive flyback inverter circuit and/or a capacitive voltage multiplier. The current output from the current source 404 is generated using only the electrical energy generated by the battery 116.

The diode 416 is connected to the current source 404 in a forward-biased configuration with respect to the current source 404 so that current flows through the diode 416 from the current source 404. The diode 416 is configured to maintain a knee voltage VZ1 and a knee voltage VZ2 (as established by the voltage clamps 408, 412) when the switching elements 444 have closed and have caused the current source 404 to collapse. The current source 404 "collapses" when the switching elements 444 close, because, with the switching elements 444 closed, the current source 404 is connected to circuit ground through diodes 440 of the driver circuits 218.

As shown in FIG. 14, the first voltage clamp 408 and the second voltage clamp 412 are operably connected to the current source 404. The first voltage clamp 408 and the second voltage clamp 412 are series-connected and are configured to establish two stacked DC voltages identified as the knee voltage VZ1 and the knee voltage VZ2. The knee voltage VZ1 is the voltage established by the voltage clamp 408, and the knee voltage VZ2 is the voltage established by the voltage clamp 412. Stacking the voltage clamps 408, 412 accomplishes a reuse of current provided by the current source 404, thereby efficiently utilizing the charge stored by the battery 116. The voltage clamps 408, 412 in one embodiment are each provided as series strings of Zener diodes. For example, in one embodiment, the voltage clamps 408, 412 are each formed from a plurality of Zener diodes connected in series, such that the voltage clamp 408 is fixed at a predetermined voltage of 246 VDC, and the voltage clamp 412 is fixed at a predetermined voltage of 650 VDC. In another embodiment, different types and/or numbers of Zener diodes are utilized and the voltage clamp 408 is fixed at a predetermined voltage ranging from 150 VDC to 350 VDC, and the voltage clamp 412 is fixed at a predetermined voltage ranging from 450 VDC to 800 VDC. The predetermined voltages at which the voltage clamps 408, 412 are fixed is also referred to herein as the knee voltage of the voltage clamps 408, 412.

The knee voltage of the voltage clamp 412 is selected to be less than a voltage that could damage (i.e., de-pole) the piezoelectric elements 182 and/or other the components of the driver circuits 218, such as the switching elements 444. Specifically, the voltage clamp 412 is a protective circuit element that protects the piezoelectric elements 182 from being driven beyond their coercive field limit 518 (FIG. 22), and protects the switching elements 444 (typically provided as MOSFETs) from exceeding their breakdown voltage.

In another embodiment, the voltage clamps 408, 412 are formed from high voltage MOSFETs as shunting elements instead of the plurality of Zener diodes. In such an embodiment, the predetermined knee voltages of the voltage clamps 408, 412 can be adjusted and selected by an external circuit, such as the microcontroller 228. Using a MOSFET as the shunting element enables the voltage clamps 408, 412 to be tuned to meet the voltage and current requirements of the selected piezoelectric elements 182.

With continued reference to FIG. 14, the voltage divider 420 includes series-connected resistors 432, 436. A voltage V3 is established by the voltage divider 420 and is provided to the voltage regulator subsystem 428. In an exemplary embodiment, the resistors 432, 436 are selected so that a voltage V3 corresponds to a voltage V2 divided by three hundred. The voltage divider 420 is configured to step down the voltage V2 to a level that is suitable for monitoring by the voltage regulator subsystem 428. In other embodiments, the voltage V2 is stepped down by the voltage divider 420 from one hundred to five hundred times for providing a suitable signal to the low-voltage voltage regulator subsystem 428.

The voltage regulator subsystem 428, in one embodiment, is a software-driven voltage regulator configured to regulate the voltage V2 by monitoring the voltage V3. In one embodiment, the voltage regulator subsystem 428 is a software block of the microcontroller 228, and the microcontroller 228 provides an electronic control signal to the voltage regulator subsystem 428 to regulate the voltage V2. The voltage regulator subsystem 428 regulates the voltage V2 by adjusting (i.e., throttling) the magnitude of current output by the current source 404.

The knee voltage of the voltage clamp 412 (i.e., voltage VZ2) establishes an upper bound on the magnitude of the voltage V2. In one embodiment, the voltage regulator subsystem 428 is configured to throttle the output of the current source 404 so that the voltage V2 is lower than the knee voltage of the voltage clamp 412. Accordingly, the voltage clamp 412 is configured as a protective device to prevent damage to the f-ESWT device 104. The voltage V2 is also referred to herein as a lower voltage rail.

The capacitor 424 of the power supply circuit 222 is configured to stabilize the voltage V2 as regulated by the voltage regulator subsystem 428. The capacitor 424 is connected in parallel to the lower power supply rail (i.e., to the voltage V2). The value of the capacitor 424 in microfarads is dictated by the electrical power demands of the piezoelectric elements 182 and the medical protocol undertaken. In an exemplary embodiment, the capacitor 424 is two microfarads (2 µF). In other embodiments, the capacitor 424 is from 0.25 microfarads to 10 microfarads. There is no corresponding capacitor on the upper rail (i.e., the voltage V1, also referred to herein as a main voltage rail).

As shown in FIG. 14, the driver circuits 218 are each operably connected to the voltage V1 (i.e., a first DC voltage output by the power supply circuit 222) and the voltage V2 (i.e., a second DC voltage output by the power supply circuit 222). The voltage V1 is a voltage across both of the voltage clamps 408, 412. An exemplary magnitude of the voltage V1 is 1000 VDC (1 kV). The voltage V2 is a voltage across only the second voltage clamp 412. In an embodiment, the voltage V2 is actively down-regulated by the voltage regulator subsystem 428 by monitoring the voltage V3; accordingly, the voltage V2 is less than or equal to the knee voltage VZ2 of the voltage clamp 412.

Each of the driver circuits 218 includes a diode 440 connected to a switching element 444, a resistor 448, and another diode 452. Each driver circuit 218 is also operably connected to a corresponding one of the piezoelectric elements 182, as shown in FIG. 14.

The diode 440 is connected to receive the voltage V1 and is forward-biased with respect to the current source 404.

In FIG. 14, the switching element 444 is connected to the cathode of the diode 440 and to circuit ground. Accordingly, the power supply circuit 222 and the switching elements 444 are electrically connected to a common circuit ground. The switching element 444 is electronically configurable in an open state and in a closed state. In an exemplary embodiment, the switching element 444 is provided as an n-channel MOSFET having a body diode. The switching element 444 includes (i) a gate terminal 445 connected to the FPGA 216, (ii) a drain terminal connected to the cathode of the diode 440, the cathode of the diode 452, and the piezoelectric element 182, and (iii) a source terminal connected to circuit ground. The gate terminal 445 of the switching element 444 is operably connected to the drive channel electronic units 220 and is configured to receive a corresponding transducer fire signal from the FPGA 216 that causes the switching element 444 to close (i.e., saturates the MOSFET). The gate terminal 445 is also referred to herein as a control terminal of the switching element 444. In one embodiment, the central clocking reference from the FPGA 216 that is operably coupled to the switching element 444 at the gate terminal 445 is 1% of the amplitude of the drive voltage pulse 514.

When the switching element 444 closes current flows through the switching element 444, and the piezoelectric element 182 generates a corresponding one of the individual shock waves 264. When the switching element 444 does not receive the transducer fire signal, the switching element 444 is open (i.e., the MOSFET is cutoff) and substantially no current flows through the switching element 444. In other embodiments, the switching element 444 is provided as any other type of controllable switch or switching element, such as another suitable type of transistor. For example, the switching element 444 is additionally or alternatively provided as an insulated gate bipolar transistor (IGBT), which is another type of high voltage semiconductor switch. The switching element 444 provided as an IGBT operates similarly to the switching element 444 provided as a MOSFET, but IGBTs are typically more costly than MOSFETs.

Based on the connection of the gate terminals 445 of the switching elements 444 to the FPGA 216, the FPGA 216 is configured to control individually when each of the switching elements 444 of the driver circuits 218 changes from the open state to the closed state and from the closed state to the open state. Accordingly, the FPGA 216 can individually control when each of the piezoelectric elements 182 generates a corresponding individual shock wave 264.

The piezoelectric element 182 is operably connected to the switching element 444 and to the power supply circuit 222 between the voltage clamps 408, 412 to selectively receive the voltage V2 and/or the voltage V4. When the switching element 444 is in the open state, the voltage V4 is considered an equivalent of the voltage V1 and differs in magnitude from the voltage V1 by the voltage drop across the diode 440. Thus, for example, when the voltage V1 is 1000 V, the voltage V4 is 999.3 V, and therefore the voltage V4 is effectively equal to the voltage V1. The voltage V2 is a regulated voltage that is less than the knee voltage VZ2 of the voltage clamp 412 by the voltage regulator 428.

With continued reference to FIG. 14, the resistor 448 and the diode 452 form a discharge circuit 466 and are connected in a series configuration to the drain of the switching element 444 to receive the voltage V2 from the power supply circuit 222. The discharge circuit 466 is connected across the piezoelectric element 182. The diode 452 is biased to enable a current flow from the resistor 448 to circuit ground through the closed switching element 444. The diode 452 prevents the resistor 448 from loading the current source 404 during the pre-charge phase in which the pre-charge voltage 510 is applied to the piezoelectric element 182. That is, the diode 452, in effect, takes the resistor 448 out of the circuit during the pre-charge phase. Absent the diode 452, the pre-charge phase would not operate properly because the power supply circuit 222 cannot support the electrical load by provided the fifteen instances of the resistor 448. As explained herein, each discharge circuit 466 quickly drains charge from the corresponding piezoelectric element 182 after the piezoelectric element 182 generates the individual shock wave 264 to prevent de-polarization of the piezoelectric elements 182 according to a transducer unloading approach.

The piezoelectric elements 182 can be modeled as capacitors, in the circuit diagram of FIG. 14, upon which an electrical field is established by the voltages V2, V4. The circuit connection between the voltage V2 and the voltage V4 corresponds to the transducer channel 224. In the exemplary embodiment of FIG. 14, the piezoelectric element 182 is connected to the drain of the switching element 444. Embodiments of the piezoelectric element 182 having a required electrical polarity are connected such that when the voltage V4 is greater than the voltage V2, the transducer 182 is in a pre-charge or pre-pulse conditioning state that contracts the transducer 182, and when the voltage V4 is less than the voltage V2, the transducer 182 is in an active state that expands the transducer 182 and generates the individual shock wave 264. As described below, the power supply circuit 222 and the driver circuits 218 configure the piezoelectric elements 182 for semi-bipolar operation in which a negative DC pre-charge voltage 510 (i.e., the voltage V2 minus the voltage V1) causes the piezoelectric elements 182 to enhance their mechanical output power upon receiving the positive drive voltage pulse 514 (i.e., the voltage V2) that "fires" the piezoelectric elements 182 upon closing of the switching element 444.

Use and Operation of the f-ESWT Device

Figure 15:
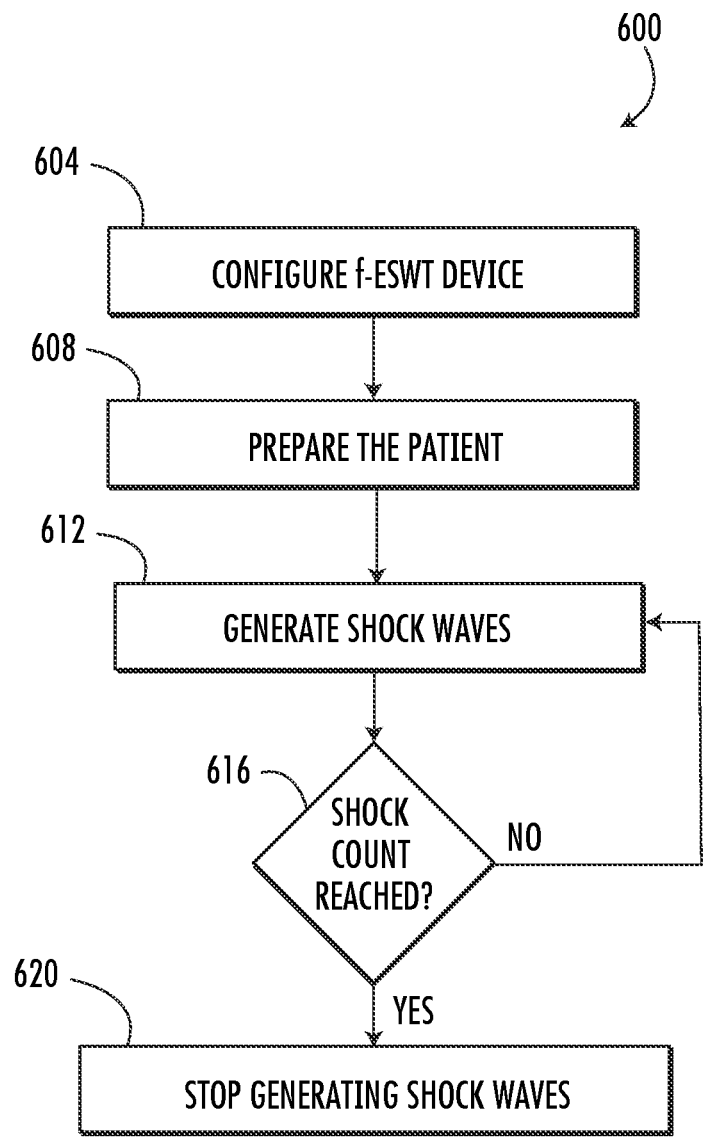
FIG. 15 is a flowchart showing a method of operating the f-ESWT kit of FIG. 1.

In operation and with reference to FIG. 15, a method 600 of operating the handheld f-ESWT device 104 generates the focused shock waves 354 in order to non-invasively repair and regenerate soft tissues such as skin, musculoskeletal, and vascular structures of a patient. The focused shock waves 354 generated by the f-ESWT device 104, when applied to the patient, trigger a biological response in tissue by the shear forces and pressure forces they produce. The focused shock waves 354 have pressures and energy flux densities that meet the requirements of most f-ESWT protocols. The f-ESWT device 104 requires no connection to an AC power outlet or an AC power source during operation and generation of the focused shock waves 354. As such, the handheld housing 150 is disconnected from electrical energy sources external to the handheld housing 150 prior to generating the focused shock waves 354 and during generating of the focused shock waves 354.

The treatments and therapies for which the f-ESWT device 104 is used are highly applicable across several very large markets including wound care (e.g., diabetic foot ulcers), orthopedics (e.g., plantar fasciitis), men's urology (e.g., erectile dysfunction and Peyronie's disease), women's urology (e.g., provoked vestibulodynia (PVD) and dyspareunia), aesthetics (e.g., facial wrinkles and cellulite), and veterinary (e.g., orthopedics and wounds). The focused shock waves 354 generated by the f-ESWT device 104 are useful in providing treatment for each of the above issues.

At block 604 of the method 600 of FIG. 15, the clinician removes the f-ESWT device 104 from the case 128 and installs a charged battery 116. Next, the clinician determines the desired focal depth 356 of the focused shock waves 354 as specified in a corresponding treatment protocol. The clinician removes the protective cover 110 from the desired standoff structure 108 to expose the interface 330 of the elastomer interior 340. A thin film of the coupling fluid 112 (i.e. mineral oil) is applied to the soft and flexible interface 330. Next, the desired standoff structure 108 is magnetically connected to the f-ESWT device 104.

The clinician powers the device "ON" using the operating button 146. When powered on, the f-ESWT device 104 automatically detects the focal depth 356 of the connected standoff structure 108 using the standoff detection module 212 and the identifier element 320. The focal depth 356 of the connected standoff structure 108 is shown on the touchscreen 142 and matches the number printed on the collar 304. Then, the clinician sets the energy flux density and determines the predetermined number of the focused shock waves 354, as typically specified in the treatment protocol, using an "ENERGY" soft button on the GUI of the touchscreen 142, for example At block 608, with the f-ESWT device 104 prepared, the clinician prepares the treatment site 386 of the patient by applying a water-based coupling gel to the skin surface 358.

Next at block 612 of the method 600, with the treatment site 386 prepared, the clinician proceeds with the treatment by pressing the treatment surface 310 of the standoff structure 108 against the skin surface 358 and pressing the operating button 146.

During the treatment, in one embodiment, the f-ESWT device 104 generates the focused shock waves 354 when the operating button 146 is pressed once, and the f-ESWT device 104 stops generating the focused shock waves 354 when the operating button 146 is pressed again. In general terms, to generate the focused shock waves 354, the microcontroller 228 operates to cause the transducer assembly 174 to be supplied with electrical energy generated by the battery 116. That is, the electrical energy to generate the focused shock waves 354 comes from only the battery 116. In response to receiving the electrical energy, each of the piezoelectric elements 182 generates a corresponding one of the individual shock waves 264. The individual shock waves 264 pass through the matching layers 186, 190 and enter the waveguide structure 308. The waveguide structure 308 receives the individual shock waves 264 that are focused into the focused shock wave 354. The focused shock wave 354 exits the waveguide structure 308 and arrives at the focal point 348. Due to accurate timing in generating the individual shock waves 264 and the orientation of the piezoelectric elements 182 as supported by the support frame 178, the individual shock waves 264 constructively converge (i.e., focus) to form the focused shock wave 354.

The f-ESWT device 104, as controlled by the microcontroller 228, generates a predetermined number of the focused shock waves 354 at the predetermined repetition frequency. That is, during the treatment, the f-ESWT device 104 generates a plurality of the focused shock waves 354 one right after another in a periodic manner. As noted above, the number of the focused shock waves 354 generated during a treatment is referred to as the shock set. At the predetermined repetition frequency of 10 Hz, a shock set of one thousand of the focused shock waves 354 could be delivered to the patient in ten seconds. Typically, however, instead of delivering all of the focused shock waves 354 of the shock set without interruption, the clinician delivers the focused shock waves 354 for two to three seconds and then pauses the treatment to monitor the patent and to reposition and/or to move the f-ESWT device 104. The predetermined repetition frequency ranges from 1 Hz to 100 Hz. In some embodiments, the predetermined repetition frequency is fixed, in other embodiments, the predetermined repetition frequency is configurable by the clinician depending at least on the type of treatment being provided.

The clinician moves the f-ESWT device 104 over the skin surface 358 at or near the treatment site 386 while the focused shock waves 354 are generated. Since the f-ESWT device 104 is portable, cordless, lightweight, and quiet, the treatment is easy to administer for the clinician and is comfortable for the patient. The shock count number on the touchscreen 142 is incremented for each focused shock wave 354 generated. The patient may hear only a low-level clicking sound during the treatment. Moreover, in one embodiment, the illuminated ring 152 (FIG. 2A) flashes during the generation of the focused shock waves 354. The focused shock waves 354 are painless to the patient.

At block 616, the f-ESWT device 104 determines if each of the focused shock waves 354 of the shock count have been generated and delivered to the patient. If the shock count has not yet been reached, then the method 600 causes the f-ESWT device 104 to continue to generate the focused shock waves 354 at block 612 as controlled using the operating button 146. When all of the predetermined number of the focused shock waves 354 of the shock set have been generated, then the f-ESWT device 104 stops generating the focused shock waves 354, as identified at block 620 of the method 600.

When the treatment has concluded, the clinician powers "OFF" the f-ESWT device 104 by pressing and holding the operating button 146 for three seconds, for example, and stores the f-ESWT device 104 and the standoff structures 108 in the case 128.

Shock Waves vs. Pressure Waves and Ultrasound

The focused shock wave 354 generated by the transducer assembly 174 is an acoustic shock wave formed from the focused combination of each of the individual acoustic shock waves 264 generated by the plurality of piezoelectric elements 182. The focused shock wave 354 is not a radial pressure wave. The focused shock wave 354 is also distinct from ultrasound and is not ultrasound. The focused shock wave 354 is "focused" because the individual shock waves 264 constructively combine and/or constructively converge at the focal point 348 to result in a region/point at which each of the individual acoustic shock waves 264 arrive at substantially the same time, resulting in a single acoustic event. Accordingly, the focused shock wave 354 is also distinct from an unfocused shock wave, which is sometimes referred to as a planar shock wave.

Figure 16A:
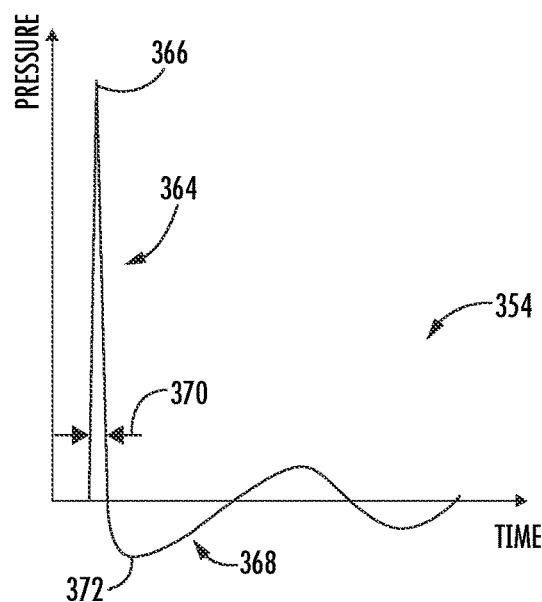
FIG. 16A is a graph illustrating a pressure of a shock wave over time, as generated by the f-ESWT device.
Figure 16B:
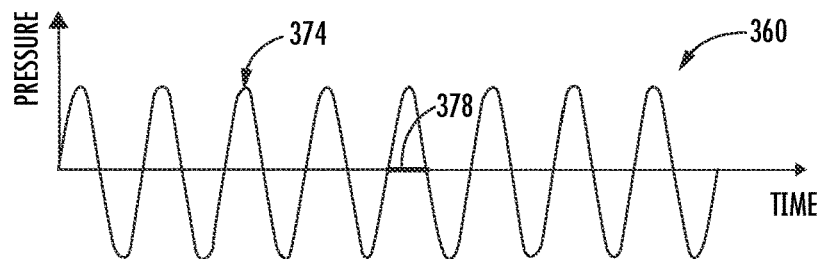
FIG. 16B is a graph illustrating a pressure of an ultrasound wave over time.
Figure 16C:
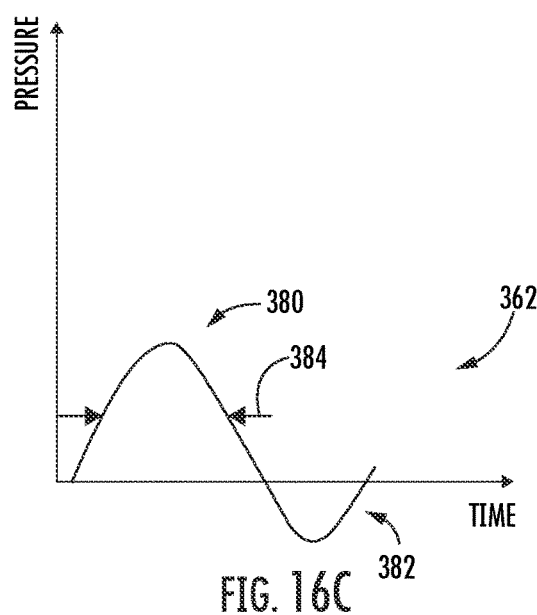
FIG. 16C is a graph illustrating a pressure of a pressure wave signal over time.

As shown in FIG. 16A, the focused shock wave 354 is compared to an exemplary ultrasound signal 360 of FIG. 16B and a pressure wave signal 362 of FIG. 16C. As can be seen in FIGS. 16A, 16B, and 16C, the focused shock wave 354 is very different from the ultrasound signal 360 and the pressure wave signal 362. FIGS. 16A, 16B, and 16C are shown at different scales, so as to make various features of the corresponding waves 354, 360, 362 visible for explanation.

In FIG. 16A, the focused shock wave 354 is a non-periodic signal having an "explosive" positive pulse 364 with a positive pressure peak 366. The positive pulse 364 is followed by a comparatively small negative tensile wave component 368. The positive pulse 364 has an incredibly steep rise and also a very steep decline within a pulse width 370. The positive pressure peak 366 of the focused shock wave 354 has a magnitude of from about 10 megapascals (10 MPa) to 100 megapascals (100 MPa). The pulse width 370 is about 200 nanoseconds. Moreover, a magnitude 372 of the negative tensile wave component 368 is around 10% of the magnitude of the positive pressure peak 366. The healing action of the focused shock wave 354 is a direct result of the positive pulse 364 impacting the body tissue.

In FIG. 16B, the medical ultrasound signal 360 is a periodic signal having positive pulses 374 and negative pulses 376 of equal magnitude. The ultrasound signal 360 defines an ultrasound pulse width 378.

In FIG. 16C, the pressure wave signal 362 includes a positive pulse 380 and a negative pulse 382. The positive pulse 380 is generated during a pressure wave pulse width 384. A magnitude of the negative pulse 382 is about 40% to 55% of a magnitude of the positive pressure pulse 380. The pressure wave signal 362 is produced by a mechanical collision of solid bodies (e.g., a metal slug mechanically propelled between metal plates or a mechanical spring-loaded cam mechanism). Devices producing radial pressure wave signals 362 commonly have a long cylindrical form factor and are cheaper to manufacture than focused shock wave devices.

With this understanding, the three types of signals 354, 360, 362 are compared. The focused shock wave 354 has the pulse width 370 that is very much shorter than the ultrasound pulse width 378 and the pressure wave pulse width 384. For example, the pulse width 370 of the focused shock wave 354 is less than 250 ns (for example, about 200 ns), the time period of the ultrasound signal 360 is about 50 microseconds, and the pulse width 384 of the pressure wave signal is 200 to 5,000 microseconds. Thus, the focused shock wave 354 reaches the positive pressure peak 366 much faster than the ultrasound signal 360 and the pressure wave signal 362.

The maximum pressure of the focused shock wave 354 is very much greater than that of the ultrasound signal 360 and the pressure wave signal 362. For example, the positive pressure peak 366 of the focused shock wave 354 is from about 10-100 MPa. The maximum pressure of the ultrasound signal 360 is negligible. The maximum pressure of the pressure wave signal 362 is only about 1 MPa. Thus, the focused shock wave 354 defines a pressure that is orders of magnitude higher than the ultrasound signal 360 and the pressure wave signal 362.

The rise time of the focused shock wave 354 very much faster than the rise times of the ultrasound signal 360 and the pressure wave signal 362. For example, an exemplary time from zero pressure to the positive pressure peak 366 of the focused shock wave 354 is less than about 30 nanoseconds. The corresponding rise time of the ultrasound signal 360 is about 500-1000 nanoseconds. The corresponding rise time of the radial pressure wave signal 362 is measured in microseconds (such as from 5 to 10 microseconds).

Another difference between the focused shock wave 354 and the pressure wave signal 362 is the ability of the focused shock wave 354 to be focused. The frequency response of the focused shock wave 354 is broadband with a center frequency around 1.5 MHz, whereas the radial pressure wave signal 362 contains low-frequency energy in the kilohertz range. Radial pressure waves, such as those forming the pressure wave signal 362, cannot be focused because the low-frequency energy produced has wavelengths much longer than a length of a corresponding applicator tip of the pressure wave device.

Moreover, a further difference between the focused shock wave 354 and the radial pressure wave signal 362 from a corresponding radial pressure device is that the radial pressure wave device produces maximum pressure at the applicator tip (i.e., at the skin surface 358) and the energy disperses (proportionally with the distance squared) in tissue or water away from the applicator tip. Whereas, the maximum pressure of the focused shock wave 354 is spaced apart from the f-ESWT device 104 at the focal point 348. Thus, the focused shock wave 354 increases in pressure between the treatment surface 310 and the focal point 348. The maximum pressure of the focused shock wave 354 is achieved internally below the skin surface 358. Depending on the shape of the interface 194 (and the corresponding arrangement of the piezoelectric elements 182), the focused shock wave 354 can be focused at any depth in tissue or water (that is less than the radius of the partially spherical arrangement of the piezoelectric elements 182, about 50 mm, for example).

While reputable companies position their products correctly in the marketplace, less reputable sellers do not properly position their products. For example, treatment devices configured for use by medical professionals are typically accurately identified as operating by generating either shock waves, pressure waves, or ultrasound. However, treatment devices configured for home use and sold by fly-by-night manufacturers, very often attempt to capitalize on the hugely beneficial treatment aspects of shock wave therapy; however, these devices simply do not actually generate shock waves. Instead, these low-cost consumer use devices are almost exclusively operated by generating pressure waves, and are incorrectly and misleadingly marketed as shock wave devices. The f-ESWT device 104 is the first completely portable, handheld, battery-powered focused shock wave therapy device.

Piezoelectric Element Time Delays

As described above, the ultrasonic pulse energy (i.e., the energy of the individual shock waves 264) travels through the waveguide structure and then through tissue to the focal point 348. For each standoff structure 108, a ratio of the individual shock wave 264 travel distance in the waveguide structure 308 (a "first medium") and the travel distance in the tissue (a "second medium") is different because the waveguide structures 308 have different lengths 344 resulting in different focal depths 356. To ensure that the pressure contributions from each of the individual shock waves 264 adds constructively at the focal point 348, for each standoff structure 108, a unique set of electronic time delays 396 (FIG. 17) is applied in each drive channel electronic unit 220 to each piezoelectric element 182. The microcontroller 228 is configured to individually control when each of the piezoelectric elements 182 generates the corresponding individual shock wave 264 using the time delays 396. More specifically, the microcontroller 228 sends signals to the FPGA 216 to control the generation of the individual shock waves 264. As explained herein, the time delays 396 make the focus of the focused shock wave 354 tighter and also raise the peak pressure of the focused shock wave 354 at the focal point 348.

The unique set of electronic time delays 396 (fifteen time delays in the illustrated embodiment) compensates for differences in sound speeds between the two mediums so the pressures from the individual shock waves 264 can be maximized at the focal point 348, resulting in an optimal focused shock wave 354 for any given standoff 108 attached to the handheld housing 150. Additionally, since the overall attenuation for each standoff structure 108 is proportional to its length 344, a "gain constant" is applied to ensure that the energy flux density (i.e., the "Energy" shown on the GUI of the touchscreen 142) is delivered at the focal point 348 independent of which standoff structure 108 is installed on the f-ESWT device 104.

The set of time delays 396, as shown graphically in FIG. 17, refers to the particular time relative to a reference time delay when the FPGA 216 activates each of the piezoelectric elements 182 to generate the individual shock waves 264. In particular, the time delays 396 correspond to the times when a transducer fire signal is sent to the drive channel electronics 220 to cause the switching element 444 to close and to fire the piezoelectric elements 182. Each of the piezoelectric elements 182 is individually controllable with a predetermined time delay 396 of the set of time delays 396.

In one embodiment, a table of fifteen time delays 396 (i.e., one time delay for each piezoelectric element 182) and a single gain constant for each standoff structure 108 is stored in nonvolatile memory resident in the microcontroller 228 or another non-transitory memory device of the f-ESWT device 104. The time delays 396 in each of the drive channel electronic units 220 compensate for: 1.) manufacturing tolerances (e.g., the orientation and position of the piezoelectric elements 182 as affixed to the mosaic support frame 178, and any phase differences between the piezoelectric elements 182 themselves, and 2.) timing differences caused by the two mediums having different sound speeds.

FIG. 17 illustrates a display screen of a benchtop pulser set showing an exemplary set of the time delays 396 required to focus the individual shock waves 264 of the transducer assembly 174 without a standoff structure 108 attached to the f-ESWT device 104. Since there is no standoff structure 108, the illustrated time delays 396 compensate for basic manufacturing tolerances from the orientation and position of the piezoelectric elements 182 as affixed to the mosaic support frame 178 and any phase differences between the piezoelectric elements 182 themselves. Channel 8 on the display screen corresponds to the piezoelectric element 182 in the center of the mosaic support frame 178 and is referred to as a reference time delay. The reference time delay is arbitrarily chosen as 500 ns. The other time delays either lead, lag, or are equal to the reference time delay. The piezoelectric elements 182 generating individual shock waves 264 that lead the individual shock wave 264 from the reference time delay, receive time delays 396 less than the 500 ns time delay 396 of the reference time delay, whereas the piezoelectric elements 182 generating individual shock waves 264 that lag the individual shock wave 264 from the reference time delay receive time delays 396 that are greater than the 500 ns time delay 396 of the reference time delay. From the data shown in FIG. 17, it can be seen that about 150 ns is required to compensate for manufacturing tolerances in the transducer assembly 174.

According to the time delays 396 shown in FIG. 17, the piezoelectric elements 182 corresponding to channels 13 and 14 have the shortest time delays 396 and are the first piezoelectric elements 182 to generate an individual shock wave 264. The piezoelectric elements 182 corresponding to channels 13 and 14 are activated at the same time. The piezoelectric element 182 corresponding to channel 11 has the longest time delay 396 and is the last piezoelectric element 182 to generate an individual shock wave 264. The exemplary order of firing the piezoelectric elements 182 in FIG. 17 is channels 13 and 14; channel 15; channel 1; channels 9 and 12; reference channel 8; channels 3, 7, and 10; channel 6, channel 4, channel 5, channel 2, and channel 11.

When the piezoelectric elements 182 are driven (i.e., activated) according to the time delays 396, the individual shock waves 364 arrive at the focal point 348 substantially simultaneously to form the focused shock wave 354. As used herein, substantially simultaneously means that the individual shock waves 364 each arrive at the focal point 348 within plus or minus 20 nanoseconds to form the focused shock wave 354.

When a first standoff structure 108 having a first focal depth 356 is connected to the housing 150, the f-ESWT device 104 is configured to identify the first standoff structure 150 using the standoff detection module 212 and to load the time delays 396 that correspond to the first standoff structure 108. When a second standoff structure 108 having a second focal depth 356 is connected to the housing 150, the f-ESWT device 104 is configured to identify the second standoff structure 150 using the standoff detection module 212 and to load a different set of the time delays 396 that correspond to the second standoff structure 108. The f-ESWT device 104 includes a potentially different set of the time delays 396 for each standoff structure 108 that is connectable to the housing 150.

Figure 18:
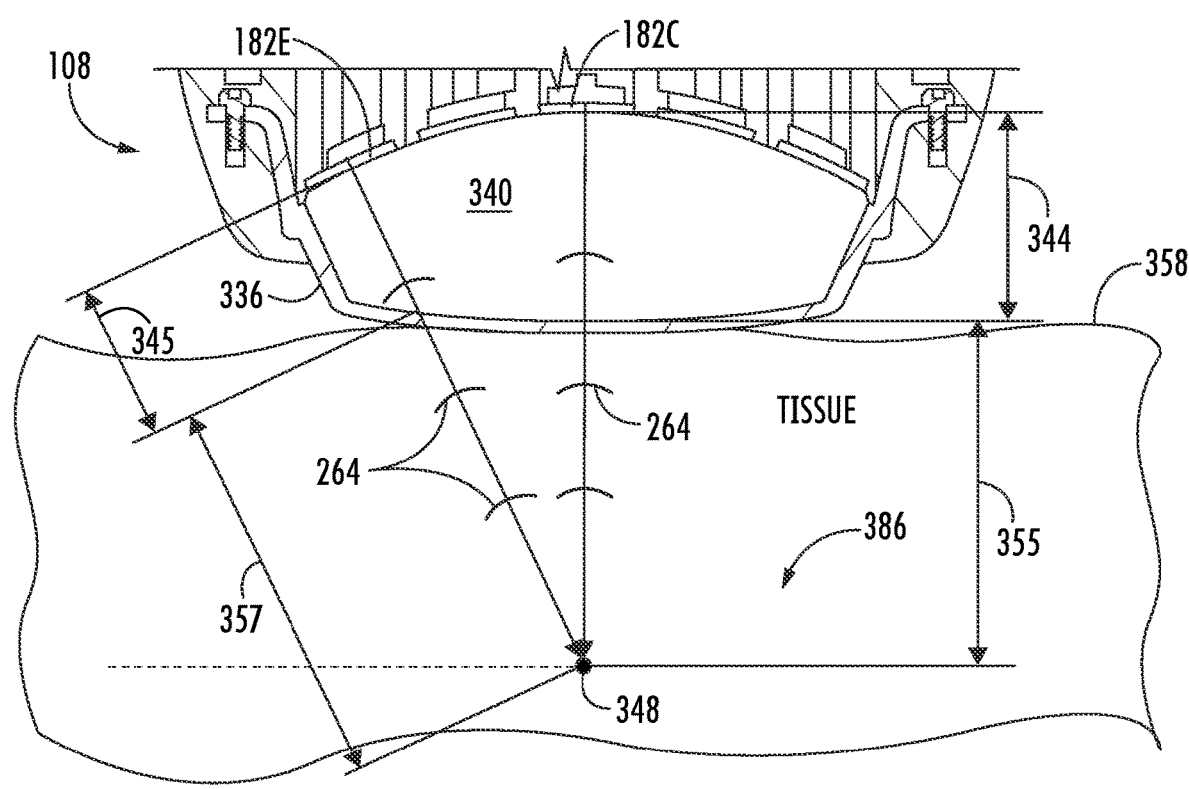
FIG. 18 is a cross-sectional view of a portion of the f-ESWT device and a standoff structure having a 30 mm focal depth.
Figure 19:
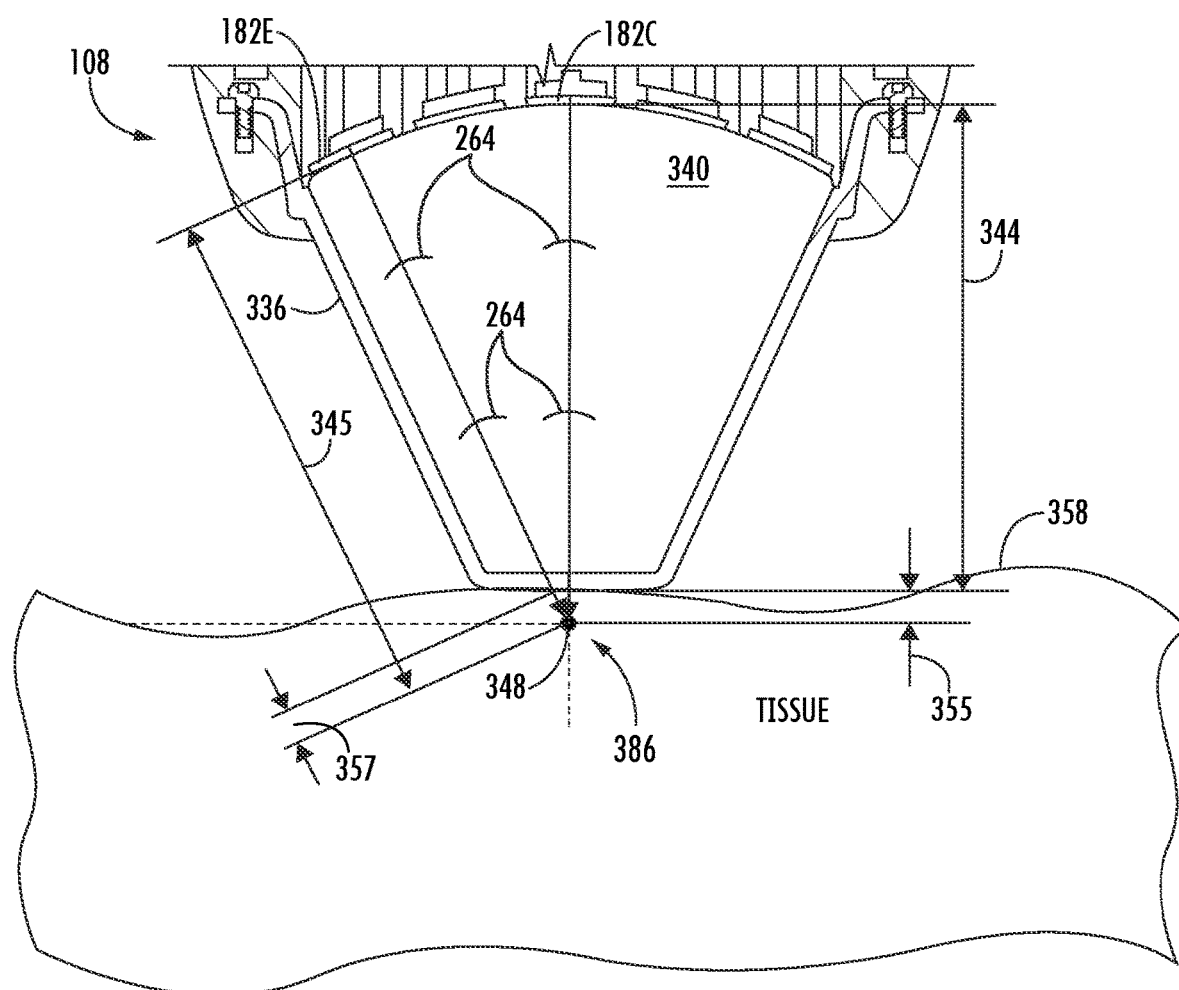
FIG. 19 is a cross-sectional view of a portion of the f-ESWT device and a standoff structure having a 2 mm focal depth.
Figure 20:
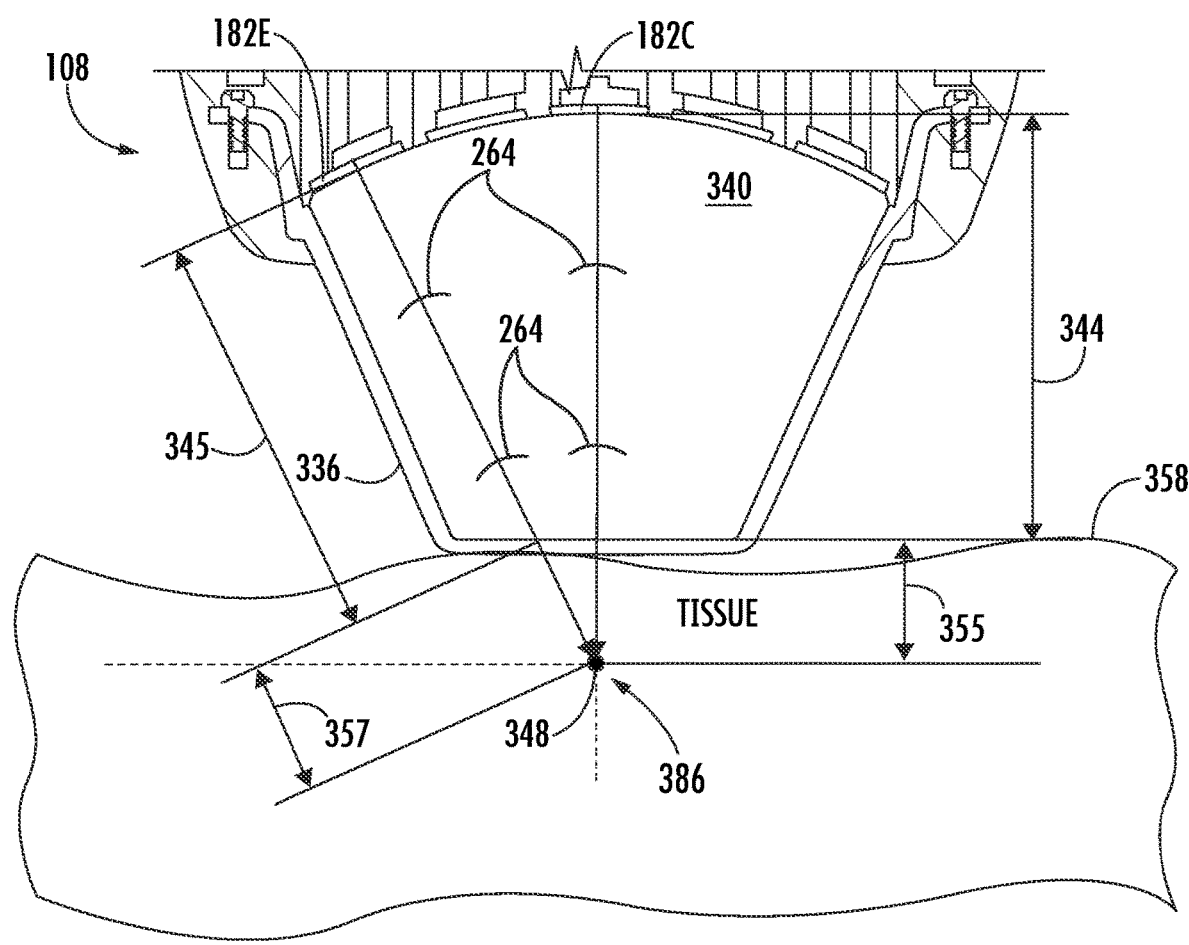
FIG. 20 is a cross-sectional view of a portion of the f-ESWT device and a standoff structure having a 10 mm focal depth.

FIGS. 18-20 show a cross-section through the center of the transducer assembly 174 and three different standoff structures 108 to assist in describing the leading and lagging time delays 396 applied to the piezoelectric elements 182 that are used to focus the shock waves 264. Specifically, FIG. 18 is a cross-section of the standoff structure 108 having a 30 mm focal depth 356, FIG. 19 is a cross-section of the standoff structure 108 having a 2 mm focal depth 356, and FIG. 20 is a cross-section of the standoff structure 108 having a 10 mm focal depth 356. Each standoff structure 108 requires a different set of the time delays 396.

To demonstrate, for each standoff structure 108, two times-of-flight $\tau$ are calculated for the individual shock waves 264 of two different piezoelectric elements 182. The time-of-flight $\tau$ is the time required for the shock wave 264 to travel from the piezoelectric element 182 to the focal point 348. The first time-of-flight $\tau$ is calculated for a center located piezoelectric element 182C (also shown in FIG. 7), and the second time-of-flight $\tau$ is calculated for an edge-located piezoelectric element 182E (also shown in FIG. 7). A time delta $\Delta\tau$ is calculated to show the required time delay 396 that must be accounted for by the FPGA 216 in order to focus the shock waves 264. That is, by delaying the activation of one of the piezoelectric elements 182C, 182E by the time delta $\Delta\tau$ the two individual shock waves arrive at the focal point 348 substantially simultaneously. In the following examples, the elastomer interior 340 is provided as SEBS polymer ($C_s$=1418 m/s)), the shock waves 264 travel through an exemplary tissue provided as water ($C_w$=1500 m/s)) to the focal point 348.

In FIG. 18, the shock wave 264 from the center piezoelectric element 182C travels the distance 344 through the elastomer interior 340 and travels the distance 355 (a first distance) through the tissue. The distance 355 also corresponds to the focal depth 356 of the standoff structure 108. The distance 344 is 0.01916 m and the distance 355 is 0.03120 m. Accordingly, the time-of-flight $\tau$ is calculated as (0.01916/1418)+(0.03120/1500)=34.312 µs. Due to the position of the edge-located piezoelectric element 182E, the corresponding shock wave 264 travels through less of the elastomer material 340 and more of the tissue to reach the focal point 348. The shock wave 264 from the edge-located piezoelectric element 182E travels the distance 345 through the elastomer interior 340 and travels the distance 357 (a second distance) through the tissue to reach the focal point 348. The distance 345 is 0.01487 m and the distance 357 is 0.03550 m. Accordingly, the time-of-flight $\tau$ is calculated as (0.01487/1418)+(0.03550/1500)=35.153 µs. The time delta $\Delta\tau$ is 159 ns (34.312 µs−34.153 µs). When the edge-mounted piezoelectric element 182E is activated 159 ns before the center piezoelectric element 182C, then the two individual shock waves 264 arrive at the focal point 348 substantially simultaneously.

In FIG. 19, the shock wave 264 from the center piezoelectric element 182C travels the distance 344 through the elastomer interior 340 and travels the distance 355 through the tissue. The distance 344 is 0.04716 m and the distance 355 is 0.00320 m. Accordingly, the time-of-flight τ is calculated as (0.04716/1418)+(0.00320/1500)=35.391 μs. The shock wave 264 from the edge-located piezoelectric element 182E travels the distance 345 through the elastomer interior 340 and travels the distance 357 through the tissue. The distance 345 is 0.04682 m and the distance 357 is 0.00355 m. Accordingly, the time-of-flight τ is calculated as (0.04682/1418)+(0.00355/1500)=35.385 μs. The time delta Δτ is 6 ns (35.391 μs−35.385 μs). When the edge-mounted piezoelectric element 182E is activated 6 ns after the center piezoelectric element 182C, then the two individual shock waves 264 arrive at the focal point 348 substantially simultaneously.

In FIG. 20, the shock wave 264 from the center piezoelectric element 182C travels the distance 344 through the elastomer interior 340 and travels the distance 355 through the tissue. The distance 344 is 0.03916 m and the distance 355 is 0.01120 m. Accordingly, the time-of-flight τ is calculated as (0.03916/1418)+(0.01120/1500)=35.083 μs. The shock wave 264 from the edge-located piezoelectric element 182E travels the distance 345 through the elastomer interior 340 and travels the distance 357 through the tissue. The distance 345 is 0.03785 m and the distance 357 is 0.01252 m. Accordingly, the time-of-flight τ is calculated as (0.03785/1418)+(0.01252/1500)=35.039 μs. The time delta Δτ is 44.0 ns (35.083 μs−35.039 μs). When the edge-mounted piezoelectric element 182E is activated 44.0 ns after the center piezoelectric element 182C, then the two individual shock waves 264 arrive at the focal point 348 substantially simultaneously.

The results of FIGS. 18-20 show that a unique time delay correction, using the time delays 396, is used for each standoff structure 108 and for each piezoelectric element 182, because a different time delta Δτ occurs for the same two piezoelectric elements 182 depending on the focal depth 356 of the standoff structure 108. Moreover, the results show that the 30 mm standoff structure 108 requires the largest time delay compensation because the difference in the time-of-flight of the "slowest" shock wave 264 and the "fastest" shock wave 264 is approximately 160 ns.

Generating the individual shock waves 264 at different times based on the time delays 396 in order to focus the individual shock waves 264 is referred to as achieving phase-differentiated transducer drive. The f-ESWT device 104 achieves phase-differentiated transducer drive without using passive delay elements, such as inductors and capacitors. By eliminating the large inductors and capacitors, the f-ESWT device 104 is compact and able to be a hand-held portable unit. The inductors and capacitors are also poorly adapted to waveforms containing a DC offset.

Method of Generating the Focused Shock Wave Based on the Time Delays

Figure 21:
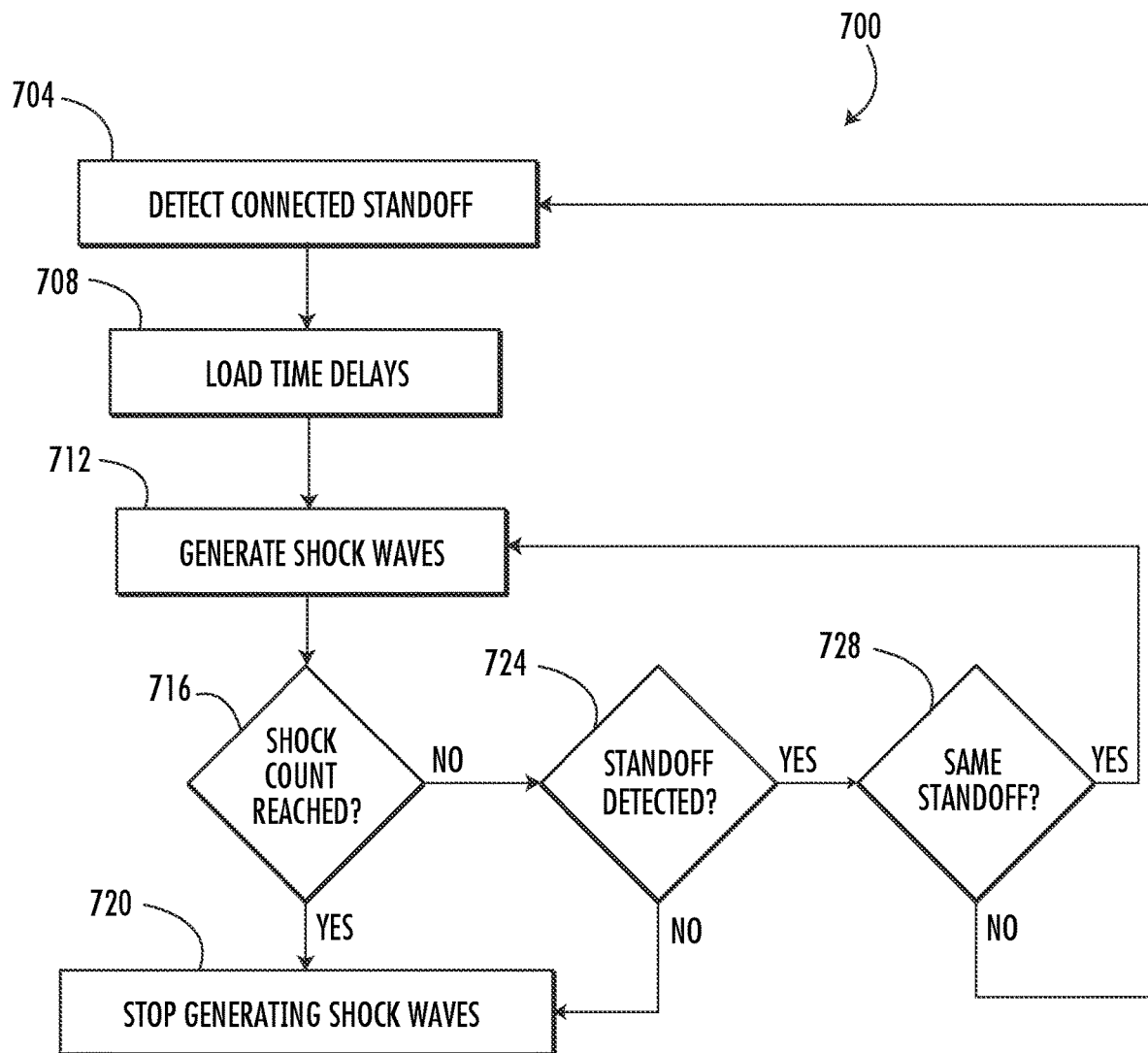
FIG. 21 is a flowchart showing a method of operating the f-ESWT device.

As shown in the flowchart of FIG. 21, a method 700 is described for generating the focused shock wave 354 using the f-ESWT device 104 according to the above-described time delays 396. In block 704, the method 700 includes automatically detecting a connected standoff structure 108 using the f-ESWT device 104. For example, the f-ESWT device 104 is configured to detect automatically that the standoff structure 108 having the 10 mm focal depth 356 is connected to the handheld housing 150 by detecting an electric signal or value from the electronic identifier element 320 using the standoff detection module 212.

Figure 12:
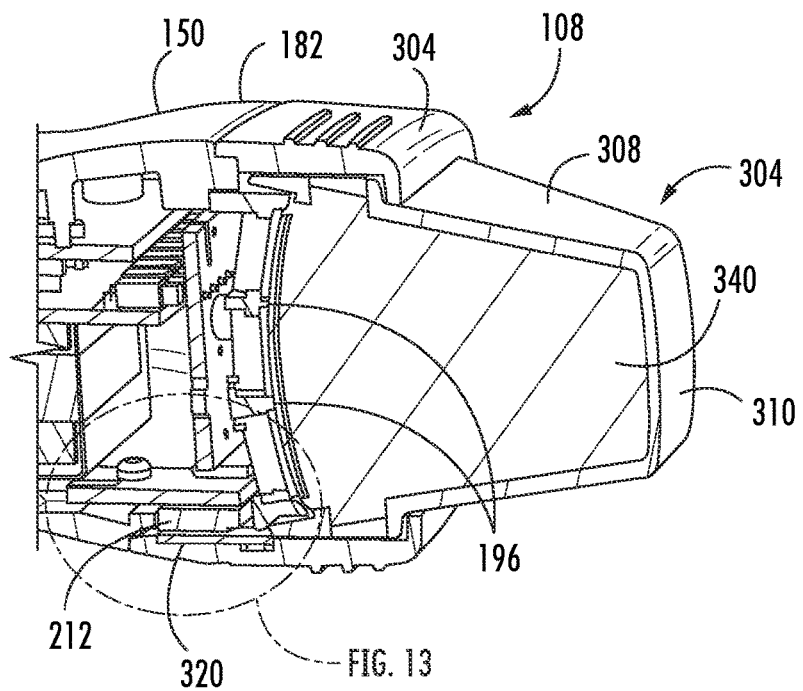
FIG. 12 illustrates a cross-sectional view showing one of the standoff structures magnetically connected to the f-ESWT device.
Figure 13:
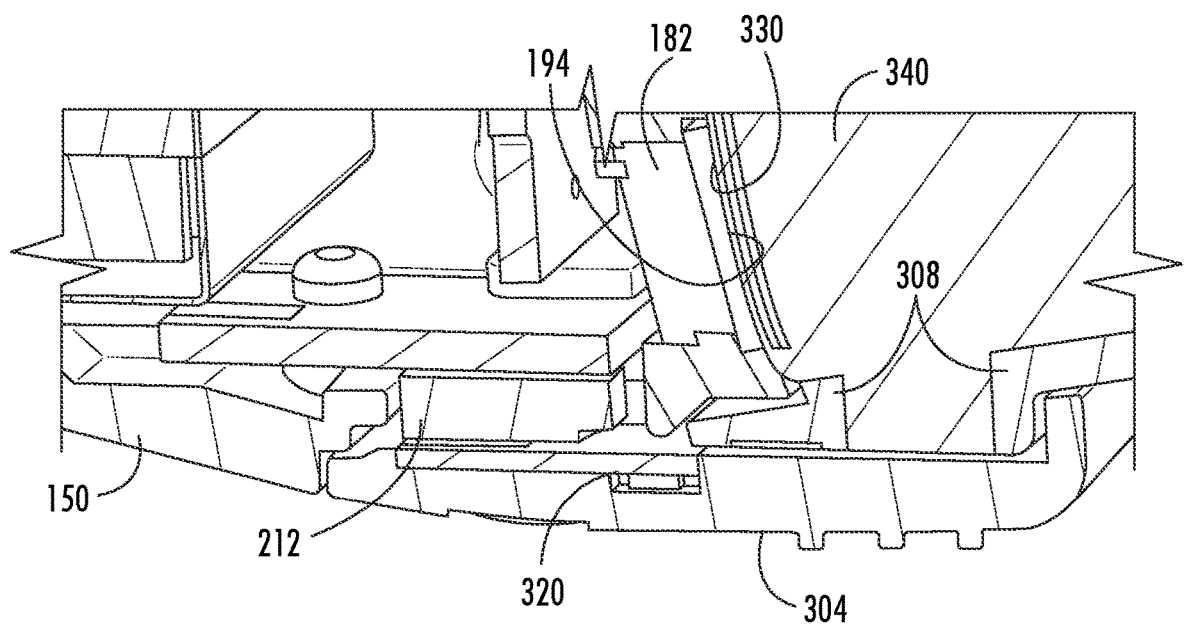
FIG. 13 is an enlarged view of a portion of FIG. 12 showing an electrical connection between the standoff structure and a housing of the f-ESWT device.

As shown in FIGS. 12 and 13, when the standoff structure 108 is magnetically connected to the housing 150 electrical terminals of the identifier element 320 are electrically connected to electrical terminals of the standoff detection module 212. In FIGS. 12 and 13, the electronic identifier element 320 is positioned to be electrically detected by the standoff detection module 212.

The standoff detection module 212 electronically communicates with the electronic identifier element 320 to receive and/or to generate a value. In one embodiment, the standoff detection module 212 includes an analog-to-digital converter configured to detect the electrical resistance of the identifier element 320 and to generate the value. The microcontroller 228 compares the value to a plurality of known values corresponding to the plurality of standoff structures 108 that are suitable for use with the handheld housing 150. The plurality of known values may be stored in an electronic memory as a table. A match (or values within a tolerance band) uniquely identifies the focal depth 356 of the connected standoff structure 108 to the f-ESWT device 104. In another embodiment, the value from the electronic identifier element 320 uniquely identifies the connected standoff structure 108 among all other standoff structures 108, even other standoff structures 108 having the same focal depth 356. For example, each standoff structure 108 may include a unique serial number or alpha-numeric code that is applied only to that specific standoff structure 108 and no other standoff structure 108. In this way, the standoff structure 108 may have a set of time delays 396 and gain constant are unique to that standoff structure 108 and used with only that specific standoff structure 108. In a further embodiment, the value from the electronic identifier element 320 corresponds directly to the focal depth 356 and/or the corresponding time delays 396 required by the specific standoff structure 108. That is, data corresponding to the time delays 396 and the focal depth 356 may be stored in the identifier element 320 and read by the standoff detection module 212.

Also, at block 704, in some embodiments, the f-ESWT device 104 is configured to update the GUI shown on the touchscreen 142 to display the detected focal depth 356 of the connected standoff structure 108. Displaying the detected focal depth 356 on the touchscreen 142 enables the clinician to compare the detected focal depth 356 to a focal depth 356 printed on the collar 304 of the standoff structure 108 to confirm that the f-ESWT device 104 has correctly identified and detected the connected standoff structure 108.

At block 704, the connected standoff structure 108 is positioned optimally to receive individual shock waves 264 from the transducer assembly 174. In particular, the interface 330 of the standoff structure 108 is positioned completely against the interface 194 of the transducer assembly 174 for an efficient transmission of the individual shock waves 264.

Next, at block 708 the microcontroller 228 loads the set of time delays 396 associated with the connected and detected standoff structure 108 to prepare for generating the focused shock waves 354. That is, in this example, the plurality of time delays 396 associated with the 10 mm standoff structure 108 is loaded. In another example, the plurality of time delays 396 associated with the specific and uniquely identified standoff structure 108 is loaded.

Next at block 712 of FIG. 21, the method 700 includes automatically driving the piezoelectric elements 182 based on the loaded time delays 396 that are associated with the connected standoff structure 108. When piezoelectric elements 182 are driven according to the loaded time delays 396, the individual shock waves 264 generated by the piezoelectric elements 182 arrive at the focal point 348 substantially simultaneously to form the focused shock wave 354. The individual shock waves 264 constructively combine at the focal point 348 due to being fired/driven at different times based on the loaded time delays 396.

During the generation of the focused shock waves 354, the magnetic connection between the housing 150 and the standoff structure 108 is strong enough to keep the standoff structure 108 securely mounted in place. The magnetically connected standoff structure 108 does not move relative to the housing 150 during the generation of the shock waves 354. That is, the pressure and energy from the focused shock wave 354 does not cause the housing 150 to recoil in a manner that separates the standoff structure 108 from the housing 150.

At block 716, the method 700 determines if the shock count has reached. That is, the method 700 determines if the clinician has caused the f-ESWT device 104 to generate all of the shock waves 354 in the current shock set. When the shock count is reached, meaning that all of the predetermined number of shock waves 354 have been generated, then the f-ESWT device 104 stops generating the focused shock waves 354, as indicated at block 720.

At block 716, when the shock count has not been reached, meaning that there are focused shock waves 354 remaining in the current shock set, then the f-ESWT device 104 performs several checks at blocks 724 and 728.

At block 724 of the method 700, the f-ESWT device 104 performs a safety check to determine if the standoff structure 108 is connected to the housing 150. In one embodiment, the f-ESWT device 104 generates the focused shock waves 354 only when the standoff structure 108 is connected to the housing 150 and is detected by the standoff detection module 212. If the clinician presses the operating button 146 to initiate shock waves 354 and the standoff structure 108 is not detected by the standoff detection module 212 or the standoff structure 108 is not connected to the housing 150, then the focused shock waves 354 are not generated, and an error message is shown on the touchscreen 142. If the standoff structure 108 is removed from the f-ESWT device 104 while the focused shock waves 354 are being generated, the f-ESWT device 104 stops generating the focused shock waves 354, and an error message is shown on the touchscreen 142. The f-ESWT device 104 detects removal of the standoff structure 108 when the identifier element 320 is not detected by the standoff detection module 212. In one embodiment, the microcontroller 228 detects the value of the identifier element 320 as detected by the standoff detection module 212 at least one time per second when the f-ESWT device 104 is powered "ON." The f-ESWT device 104 does not generate the focused shock waves 354 without one of the standoff structures 108 properly connected to the housing 150.

Next, at block 728 the method 700 includes determining if the same standoff structure is connected to the housing 150 as was initially detected at block 704. This check is done to ensure that the f-ESWT device 104 is applying the optimal time delays 396 and the optimal gain constant to the connected standoff structure 108 to optimally generate the focused shock waves 354. The f-ESWT device 104 uses the standoff detection module 212 and the corresponding electronic value received from the electronic identifier element 320 of the connected standoff structure 108 to make this determination.

At block 728, when the same standoff structure 108 is connected and detected, then the method 700 moves to block 712 and the shock waves 354 may continue to be generated.

When, however, at block 728, the same standoff structure 108 is not detected (i.e., a different standoff structure 108 is connected and detected), then the method 700 moves back to block 708 to load the plurality of time delays 396 and gain constant associated with the connected standoff structure 108. In this example, the different standoff structure 108 has an associated set of time delays 396 and gain constant that are different than the set of time delays 396 and gain constant that were initially loaded by the microcontroller 228. For example, the clinician may have started the shock wave treatment with the standoff structure 108 having the 10 mm focal depth 356, and then changed to the standoff structure 108 having the 20 mm focal depth 356 after generating some of the focused shock waves 356 of the shock set. The clinician may finish generating the focused shock waves 356 of the shock set with the standoff structure 108 having the 20 mm focal depth after the proper time delays 396 and gain constant are determined and applied by the microcontroller 228. The f-ESWT device 104 is configured to automatically load and utilize the optimal set of time delays 396 and gain constant for the connected standoff structure 108.

It is noted that in some embodiments, a detected change in the connected standoff structure 108 during a shock set, may cause the shock count to reset and/or may generate a warning message and/or an informational message on the display.

Pre-Charge and Transducer Unloading

It is technically challenging to reach therapeutic shock wave 354 energy levels with a small area transducer array (i.e., the piezoelectric transducer assembly 174), especially at magnitudes of drive voltage pulses 514 (FIG. 22) suitable for a battery-operated, hand-held device, such as the f-ESWT device 104. To maximize the energy output of the focused shock wave 354, in one embodiment, a soft piezoelectric material is used to form the piezoelectric elements 182. The term "soft" piezoelectric material includes single crystal piezoelectric materials. The selected soft piezoelectric material has the highest dielectric constant (capacitance) available and high coupling coefficients (efficiency). Exemplary single crystal piezoelectric materials suitable for forming the piezoelectric elements 182 include lead magnesium niobate-lead titanate (PMN-PT) crystals and lead indium niobate-lead magnesium niobate-lead titanate (PIN-PMN-PT) crystals, each of which has a very high energy density and is a high performing material. As explained below, a downside of using a soft piezoelectric material for the piezoelectric elements 182 is a comparatively low coercive field limit 518 (FIG. 22); however, the f-ESWT device 104 overcomes this issue and effectively uses soft piezoelectric material(s) and/or a single crystal piezoelectric material(s) to reliably generate the focused shock waves 354.

With reference to FIG. 22, the coercive field limit 518 of the soft piezoelectric elements 182 refers to a maximum coercive field that can be applied to the piezoelectric elements 182 without irreversibly damaging the piezoelectric elements 182. Specifically, when driven by the drive voltage pulse 514, the piezoelectric elements 182 are exposed to a very strong electrostatic field (i.e., a coercive field) that could cause the piezoelectric elements 182 to change polarity at least partially. The at least partial change in polarity is referred to as "de-poling." De-poling causes the piezoelectric element 182 to generate a weaker individual shock wave 264 because the piezoelectric element 182 responds less uniformly to the drive voltage pulse 514. The coercive field limit is the voltage at which de-poling of the piezoelectric element 182 begins to occur.

For comparison, piezoelectric lithotripters and other non-portable ESWT devices are AC-powered and use a "hard" piezo-ceramic material, such as PZT8. These non-portable "hard" piezoelectric systems use very high drive voltages (i.e., many kilovolts) to compensate for the lower dielectric and coupling coefficients of the hard piezo-ceramic material. Moreover, these non-portable AC-powered devices are unconcerned about de-poling of the hard piezoceramic material and any coercive field limits, because the hard piezo-ceramic material can withstand the very high drive voltage and more without any de-poling effects. These high drive voltages, however, are not practical and cannot be used in a hand-held battery-operated device, because there is simply no way practical way to supply the high level of electrical energy in a handheld, small, and portable form factor.

It is counterintuitive to use a soft piezoelectric material and/or a single crystal piezoelectric material, such as the material of the piezoelectric elements 182, in a shock wave generation application. Soft piezoelectric materials (including soft piezoceramic materials and single crystal piezoelectric materials) were developed for low voltage applications like diagnostic ultrasound, in which there is only a periodic signal without any sharp voltage pulse. In a battery-powered handheld device, such as the f-ESWT device 104, hard piezoceramic materials are unusable, thereby making soft piezoceramic materials a viable option for shock wave generation, when appropriate electrical signals are applied.

In the handheld battery-powered f-ESWT device 104, in one embodiment, CTS 3265HD was selected as the material of the piezoelectric elements 182. The piezoelectric elements 182 produced from this material have very high capacitance, which results in high energy transfer from the drive channel electronic units 220. Additionally, the coupling coefficients associated with CTS 3265HD piezoelectric material are very high, which also translates into high output for a given input. These types of soft piezoelectric materials, however, have a lower coercive field as compared to the hard piezoelectric materials used in non-portable devices and, therefore, have a lower maximum drive voltage pulse before the piezoelectric material will de-pole.

The coercive field of CTS 3265HD is 5.6 kV/cm; accordingly, a 1.1 mm thick piezoelectric element 182 made from CTS 3265HD will have a maximum voltage limit of about 616 V before de-poling occurs. A voltage of about 616 V is from 606 V to 626 V. Suitable coercive field limits of other soft piezoelectric materials and/or single crystal piezoelectric materials suitable for forming the piezoelectric elements 182 range from 2.5 kV/cm to 15 kV/cm. Piezoelectric materials having a coercive field limit greater than 15 kV/cm are typically hard piezoelectric materials. Once the piezoelectric material begins to de-pole, its capacitance drops and the energy level diminishes of the corresponding shock wave 264. De-poling of the piezoelectric elements 182 is to be avoided in order to prolong the operational lifespan of the transducer assembly 174.

Figure 23:
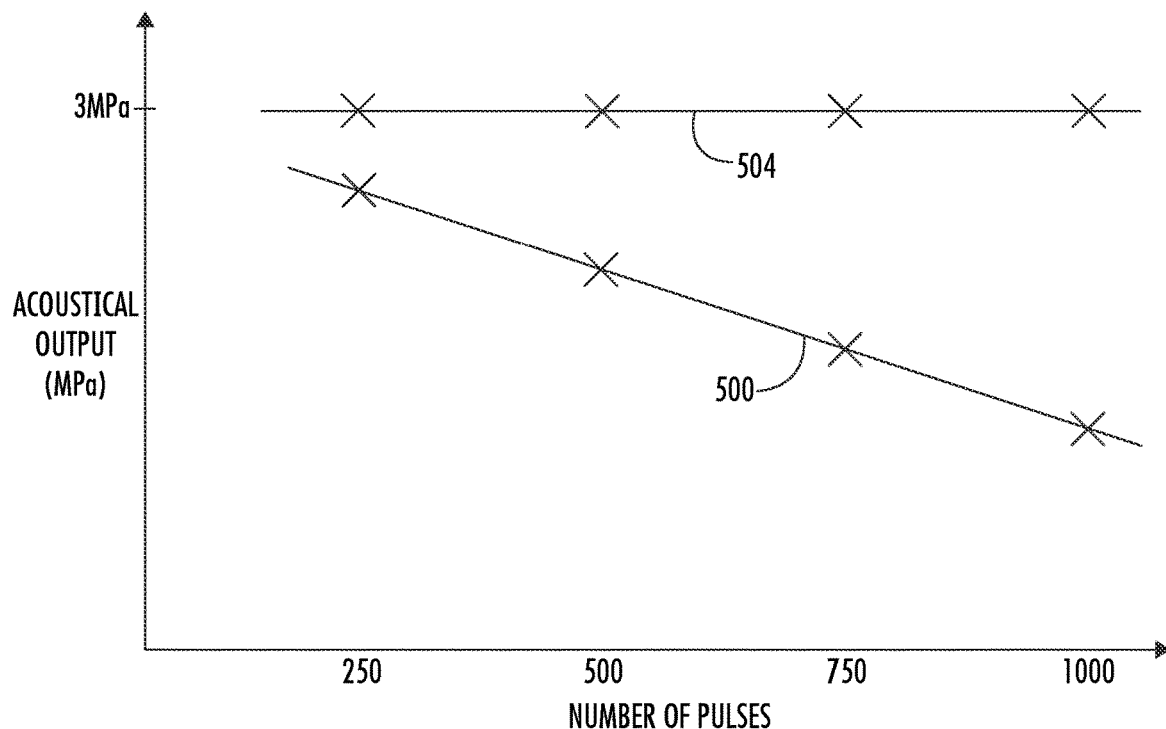
FIG. 23 is a graph of acoustical output pressure versus a number of drive voltage pulses applied to the piezoelectric elements of the f-ESWT device shown with and without a pre-charge voltage applied to the piezoelectric elements.
Figure 24:
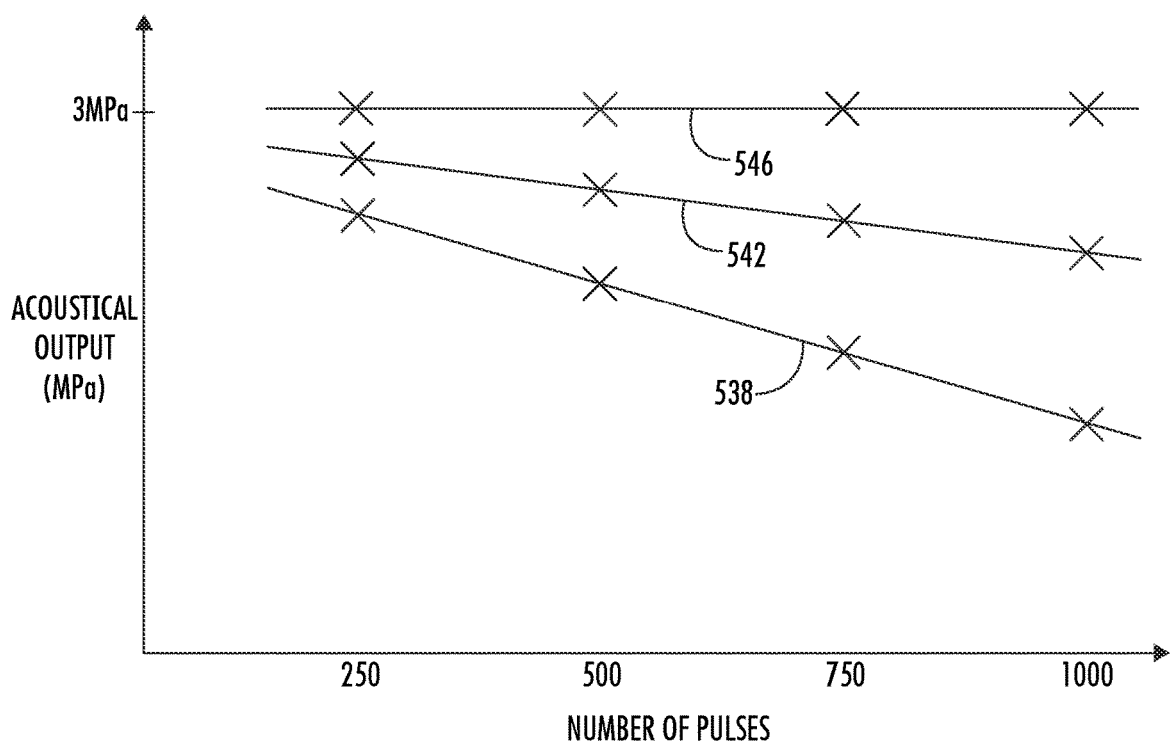
FIG. 24 is a graph of acoustical output pressure versus the number of drive voltage pulses applied to the piezoelectric elements of the f-ESWT device shown for three different pulse widths and according to a transducer unloading approach.

With reference to FIGS. 22-24, the f-ESWT device 104 uses two techniques to enable the piezoelectric elements 182 to be formed from soft piezoelectric material and/or single crystal piezoelectric material and to be repeatedly supplied with drive voltage pulses 514 at or near the coercive field limit 518 for generating the shock waves 264 without de-poling the piezoelectric elements 182. The first technique is called pre-charge. As shown in FIG. 22, in one embodiment, an electrical drive signal 508 supplied to each piezoelectric element 182 starts at zero volts and then drops to a negative pre-charge voltage 510. The magnitude of the negative pre-charge voltage 510 is equal to about 30% of the amplitude of the maximum positive drive voltage pulse 514. In one embodiment, the drive signal 508 starts at about a negative 200 V pre-charge voltage 510 that remains on the piezoelectric elements 182 for a predetermined time period of approximately 1 ms or longer. The predetermined time period of the pre-charge voltage 510 ranges from 0.5 ms to 100 ms or more, in one embodiment. An exemplary predetermined time period is from 8 ms to 12 ms, and a specific predetermined time period is 10 ms. A pre-charge voltage of about 200 V is from 190 V to 210 V. The pre-charge voltage 510 contracts the soft piezoelectric element 182 in a thickness direction (i.e., along the normal axis 274), thereby increasing the overall strain available during the power cycle (i.e., when the drive voltage pulse 514 is applied). Stated differently, the pre-charge voltage 510 "compresses" the piezoelectric elements 182 prior to the piezoelectric elements 182 receiving the drive voltage pulse 514 and generating the individual shock waves 264. The predetermined time period of 10 ms is much longer than typically applied to a piezoelectric element. It has been found that spending much more time than typical at the negative pre-charge voltage 510 prior to supplying the piezoelectric element 182 with the drive voltage pulse 514 helps reduce de-poling and/or halt de-poling in response to the drive voltage pulse 514.

The pre-charge voltage 510 is a "conditioning" voltage that is applied to the piezoelectric elements 182 to prevent de-poling of the elements 182 in response to the drive voltage pulse 514 applied thereto, which generates the focused shock wave 354. The pre-charge voltage 510 allows the drive voltage pulse 514 applied to the piezoelectric elements 182 to be near or perhaps even higher than the coercive field limit 518 of the piezoceramic material without de-poling.

After the pre-charge voltage 510 is applied for the predetermined time period, the drive signal abruptly changes to a +600 V (exemplary magnitude value) drive voltage pulse 514 to cause the pre-charged piezoelectric element 182 to produce the shock wave 264. The drive voltage pulse 514 is about 600 V meaning that the DC drive voltage pulse is from 590 V to 610 V. The drive voltage pulse 514 is less than but is very close to the coercive field limit 518 of the piezoelectric elements 182, which is about 616 V. Accordingly, in one embodiment, the drive voltage pulse 514 is within plus or minus twenty percent of the coercive field limit 518 of the piezoelectric elements 182. The pre-charge approach in which (i) a high magnitude negative pre-charge voltage 510 is applied for (ii) a comparatively long predetermined time period, conditions the piezoelectric element 182 to be repeatedly driven at, near, or slightly above the coercive field limit 518 without de-poling and without irreversibly damaging the piezoelectric elements 182.

The pre-charge approach is referred to as "semi-bipolar operation" of the piezoelectric elements 182. The "two poles" of the "bipolar" operation correspond to (i) a voltage of a first polarity (i.e., negative) applied to the piezoelectric element 182 as the pre-charge voltage 510, and (ii) a drive voltage pulse of a second opposite polarity (i.e., positive) applied the piezoelectric element 182 to generate the shock wave 264. Notably, as described herein, the exemplary driver circuit 218 shown in FIG. 14 accomplishes the semi-bipolar operation of the piezoelectric elements 182 using only one switching element 444 per piezoelectric element 182 and only one power supply circuit 222. The term "semi" in the term "semi-bipolar operation" refers to the difference in magnitude between the two voltages applied to the piezoelectric elements 182. In particular, the pre-charge voltage 510 typically has a lower magnitude than the drive voltage pulse 514 and, therefore, the piezoelectric elements 182 are not operated in "full bi-polar operation." In full bi-polar operation the pre-charge voltage 510 and the drive voltage pulse 514 would have opposite polarity voltages of substantially the same magnitude.

FIG. 23 qualitatively shows the conditioning effect of the pre-charge voltage 510 on de-poling and the corresponding pressure output of the focused shock wave 354 generated by the piezoelectric elements 182. As shown in FIG. 23, the resultant pressure of the focused shock wave 354 is measured after 250, 500, 750, and 1000 pulses for two setups 500, 504. In the first setup 500, the drive signal 508 does not include the pre-charge voltage 510 and the piezoelectric elements 182 are driven with a 600 V drive voltage pulse 514. As shown, in the first setup 500, the resultant pressure of the focused shock wave 354 declines from near 2.8 MPa after 250 pulses to only 1.3 MPa after 1000 pulses. This decline in pressure of the focused shock wave 354 is the result of de-poling of the piezoelectric elements 182, which causes the piezoelectric elements 182 to generate the shock waves 264 less effectively after each drive voltage pulse 514.

In the second setup 504, which is used by the f-ESWT device 104, the piezoelectric elements 182 are pre-charged with about a −200 V pre-charge voltage 510 prior to being driven with the +600 V drive voltage pulse 514. As shown by the horizontal line connecting the measured pressures, no loss in pressure of the focused shock wave 354 occurs in the second setup 504, even after 1000 pulses of the drive voltage pulse 514, indicating that no de-poling of the piezoelectric elements 182 has occurred. The f-ESWT device 104 uses the pre-charge voltage 510 in a novel manner for avoiding de-poling of the soft piezoelectric elements 182 when the piezoelectric elements 182 are driven with a drive voltage pulse 514 near the coercive field limit 518.

Moreover, in the second setup 504, the piezoelectric elements 182 generate the focused shock wave 354 with a higher pressure (i.e., 3 MPa) than can be achieved in the first setup 500, even prior to the observed de-poling in the first setup 500. Thus, the f-ESWT device 104 uses the pre-charge voltage 510 to boost the pressure output of the piezoelectric elements 182 as compared to piezoelectric elements 182 that are not supplied with a pre-charge voltage 510 prior to receiving the drive voltage pulse 514.

With reference again to FIG. 22, the second technique to enable the piezoelectric elements 182 to be supplied with the drive voltage pulse 514 at or near the coercive field limit 518 without de-poling is referred to as transducer unloading. For a given piezoelectric element 182 thickness, there is an optimal duration of the drive voltage pulse 514 that achieves maximum acoustical output of the resultant shock wave 264. It has been found that a drive voltage pulse 514 duration longer than needed does not increase the acoustical output and results in early de-poling of the piezoelectric elements 182. Accordingly, the f-ESWT device 104 includes circuitry that achieves the optimal duration of the drive voltage pulse 514 by unloading the voltage/charge on the piezoelectric elements 182 more quickly than compared to a natural decay of the voltage/charge. The transducer unloading approach reduces the amount of time that the drive voltage pulse 514 is applied to the piezoelectric elements 182. Stated differently, transducer unloading reduces a pulse width 522 of the drive voltage pulse 514 and drives the voltage applied to the piezoelectric elements 182 down to near zero volts more quickly than the voltage would otherwise fall to near zero volts through RC-type discharge, natural leakage paths, and parasitic-type discharge (i.e., natural decay).

The effects of transducer unloading are compared to natural decay graphically in FIG. 22. After the drive voltage pulse 514, the dotted line decay 526 corresponds to the natural decay of the circuit, and the solid line decay 530 corresponds to the transducer unloading approach. As shown, the transducer unloading approach returns the voltage across the piezoelectric elements 182 to near zero volts much more quickly than the natural decay approach. To further illustrate, the pulse width 522 is compared to the pulse width 534. The pulse width 522 associated with the transducer unloading approach is about 200 ns, whereas the pulse width 534 associated with the natural decay approach is approximately 100 ms (FIG. 22 is not shown to scale). Notably, the natural decay approach extends into the predetermined time period of the pre-charge voltage 510 and interferes in proper pre-charging of the piezoelectric elements 182. Transducer unloading greatly reduces the time that the piezoelectric elements 182 are exposed to the high voltages in the drive signal 508.

FIG. 24 qualitatively shows the effect of the transducer unloading approach of the drive voltage signal 508 on de-poling of the piezoelectric elements 182. As shown in FIG. 24, the resultant pressure of the focused shock wave 354 is measured after 250, 500, 750, and 1000 pulses for three setups 538, 542 and 546. In the first setup 538, no transducer unloading or pre-charge voltage 510 is used and the pulse width 534 is about 1.2 μs. De-poling occurs and the resultant pressure of the focused shock wave 354 declines from near 2.3 MPa after 250 pulses to only 1.0 MPa after 1000 pulses. In the second setup 542, transducer unloading is used and the pulse width 522 is about 0.6 μs. No pre-charge voltage 510 is used in the second setup 542. De-poling occurs and the resultant pressure of the focused shock wave 354 declines from near 2.6 MPa after 250 pulses to only 2.0 MPa after 1000 pulses. In the third setup 546, transducer unloading is used as well as the pre-charge voltage 510 (i.e., about −200 V), and the pulse width 522 is about 0.3 μs. As shown in the third setup 546, no de-poling occurs and the resultant pressure of the focused shock wave 354 is consistently at 3.0 MPa even after 1000 pulses.

The transducer unloading approach tends to avoid de-poling in response to high drive voltage pulses 514 (i.e., drive voltage pulses 514 close the coercive field limit 518) as used by the f-ESWT device 104, and optimizes the pulse width 522 to reliably obtain the focused shock wave 354 having a very high pressure.

Method of Utilizing Pre-Charge and Transducer Unloading

Figure 25:
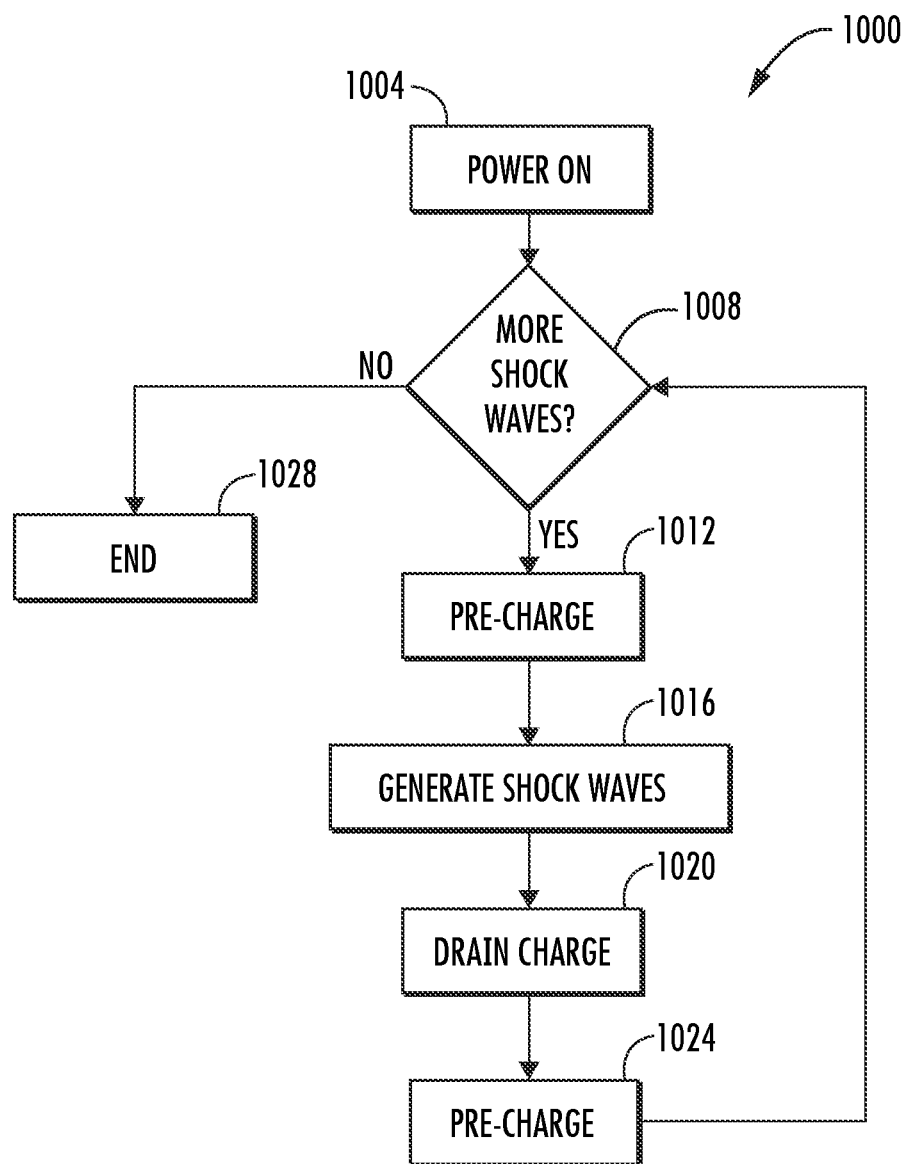
FIG. 25 is a flowchart showing a method of generating the shock waves according to a pre-charge voltage approach and the transducer unloading approach.

With reference to the flowchart of FIG. 25 and the circuit diagram of FIG. 14, an exemplary method 1000 is disclosed for pre-charging and firing the piezoelectric elements 182 to generate the shock waves 264 with high mechanical energy without de-poling the piezoelectric elements 182. At block 1004, the f-ESWT device 104 is powered on, and at block 1008 the microcontroller 228 determines if the focused shock waves 354 should be generated. When it is determined that the focused shock waves 354 should be generated, at block 1012, the microcontroller 228 causes the driver circuits 218 and the power supply circuit 222 to apply the pre-charge voltage 510 to the piezoelectric elements 182 to prepare the piezoelectric elements 182 to receive the drive voltage pulse 514 without de-poling.

To apply the pre-charge voltage 510, the switching element 444 is maintained in an open configuration that prevents current from passing to ground through the switching element 444. In this configuration, the voltage V4 eventually rises to equal the voltage V1, and both the voltage V1 and the voltage V2 are applied to the piezoelectric element 182 as the DC pre-charge voltage 510. That is, the difference between the voltages V1 and V2 is the pre-charge voltage 510. The voltage V4 rises to the voltage V1 within a period of approximately one to five milliseconds. The voltage V4 is greater in magnitude than the voltage V2 (which is also applied to the piezoelectric element 182), and, results in an electrical field being applied to the piezoelectric element 182 having a polarity as shown in FIG. 14. In this configuration, with the switching element 444 in the open state, both the voltages V2 and V1 are applied to the piezoelectric element 182 to pre-charge the piezoelectric element 182 with a DC pre-charge voltage 510 having a first polarity. In particular, the polarity symbols on the piezoelectric elements 182, as shown in FIG. 14, are consistent with an electric field that will pre-charge (i.e., repolarize) the piezoelectric elements 182. The voltage V4 (equal to the voltage V1) as applied to the piezoelectric element 182 pre-charges the piezoelectric element 182. In an exemplary embodiment, the predetermined voltage across the piezoelectric element 182 during the pre-charge phase is about 250 VDC (i.e., V1 minus V2). In other embodiments, the predetermined voltage across the piezoelectric element 182 during the pre-charge phase is from 200 VDC to 300 VDC. Moreover, the pre-charged piezoelectric elements 182, in one embodiment, are maintained in the pre-charge phase (i.e., with the pre-charge voltage 510 applied) for more than 1 ms.

Next, at block 1016 of the flowchart of FIG. 25, the FPGA 216 as controlled by the microcontroller 228, delivers a plurality of individual fire signals to the driver circuits 218 using the time delays 396, as described above. When the switching element 444 is supplied with the fire signal, the switching element 444 very quickly closes and provides a circuit path to ground therethrough. That is, the drain voltage of the switching element 444 quickly falls to system ground when the switching element 444 closes. Moreover, with the switching element 444 closed, the voltage V4 (which is equal to V1) drops to zero or near zero and only the voltage V2 remains applied to the piezoelectric element 182. Accordingly, the polarity of the electric field applied to the pre-charged piezoelectric elements 182 is very abruptly reversed to the de-polarizing direction. When the electric field applied to the pre-charged piezoelectric elements 182 reverses, the pre-charged piezoelectric elements 182 generate the individual shock waves 264. The switching element 444 receives the fire signal for only a very short predetermined time period, ranging from 200 to 500 ns. In a specific embodiment, the fire signal is supplied to the switching element 444 to fire the pre-charged piezoelectric element 182 for a predetermined time period of 350 ns.

Based on the above, the circuit of FIG. 14 accomplishes the semi-bipolar transducer drive using a single N-channel MOSFET transistor 444 per piezoelectric element 182 and with a single common high voltage power supply 222 shared by all of the piezoelectric elements 182. With the switching element 444 open, the piezoelectric element 182 is supplied with a polarizing electric field of a first polarity (i.e., the pre-charge voltage 510), and when the switching element 444 closes the transducer 182 is driven with a stronger de-polarizing electric field of an opposite second polarity (i.e., the drive voltage pulse 514). The driver circuits 218 switch between the bipolar drives simply by controlling the state of the switching element 444 between the open (cut-off) and closed (saturated) states using the microcontroller 228 and the FPGA 216. The semi-bipolar operation (also referred to herein as semi-bipolar drive), as provided by the driver circuits 218, uses no passive delay elements and therefore consumes less printed circuit board space, thereby contributing, in part, to the compact and portable configuration of the f-ESWT device 104.

It is noted that the diode 416 shields the voltage V2 and the voltages across the piezoelectric elements 182 from the collapse of the voltage V4/V1 caused by the closing of the switches 444. The diode 416 also provides inter-channel isolation given that each channel fires at a different time as determined by the time delays 396 and the FPGA 216.

Next, at block 1020 of the method 1000, the discharge circuit 466 is used to provide transducer unloading to the piezoelectric elements 182. The discharge circuit 466 provides transducer unloading according to an approach referred to herein as the resistor/diode per-channel method. The discharge circuit 466 includes the series-connected resistor 448 and diode 452. The discharge circuit 466 provides a dissipating path that enables the voltage bias of the piezoelectric elements 182 to return to zero volts or to near zero volts after generation of the individual shock waves 264. In operation, closing of the switching element 444 simultaneously applies the drive voltage pulse 514 to the piezoelectric element 182 and the discharge circuit 466. Accordingly, with the switching element 444 in the closed configuration, the piezoelectric element 182 generates the shock wave 264 in response to the drive voltage pulse 514. Then, when the switching element 444 opens after generation of the shock wave 264, the charge stored in the piezoelectric element 182 from the drive voltage pulse 514 is drained by the discharge circuit 466 to unload the piezoelectric element 182. Unloading the piezoelectric elements 182 reduces the amount of time that the piezoelectric elements 182 are subject to a coercive field near the coercive field limit 518, and further tends to reduce de-poling of the piezoelectric elements 182. In the circuit of FIG. 14, unloading of the piezoelectric elements 182 commences when the switching elements 444 open after the generation of the individual shock waves 264. The unloading does not require a connection to circuit ground through the switching elements 444.

Next, at block 1024, with the fire signal no longer supplied to the switching element 444, the switching element 444 is again in the open configuration that results in the pre-charge voltage 510 being supplied to the piezoelectric elements 182. The pre-charge voltage 510 prepares the piezoelectric elements 182 to receive a further drive voltage pulse 514 if the microcontroller 228 determines that additional focused shock waves 354 should be generated.

At block 1008 of the method 1000 if additional focused shock waves 354 should be generated, then the microcontroller 1008 proceeds according to the blocks 1012, 1016, 1020, and 1024. If, however, no further shock waves should be generated, then the method 1000 ends at block 1028.

In some embodiments, in operating the f-ESWT device 104 the clinician selects the energy level of the focused shock wave 354. The energy level is also referred to as an acoustic power output of the f-ESWT device 104. The f-ESWT device 104 controls the energy level of the focused shock wave 354 by adjusting the magnitude of the voltage V2 using the voltage regulator subsystem 428. In particular, the energy level of the focused shock wave 354 is reduced by reducing the magnitude of the voltage V2. The energy level of the focused shock wave 354 is increased by increasing the magnitude of the voltage V2 as limited by knee voltage VZ2. Such an approach tailors the output energy level of the f-ESWT device 104 to correspond to a predetermined energy level as set forth by a medical protocol, for example.

Moreover, f-ESWT device 104 includes circuitry and processes for varying the acoustic power output and peak amplitude of drive voltage pulse 514 while keeping constant the pre-charge voltage 510. That is, in one embodiment, the voltage regulator subsystem 428 is configured to change the voltage V1 and the voltage V2 in a corresponding manner that causes the difference between the voltage V1 and the voltage V2 (i.e., the pre-charge voltage 510) to remain constant. For example, in one configuration, the voltage V1 is 800 V and the voltage V2 is 600 V at a first acoustic output power, and in a second configuration the voltage V1 is 700 V and the voltage V2 is 500 V at a second acoustic output power. In each configuration the pre-charge voltage is held constant at −200 V, even during the down-regulation of the lower voltage rail (i.e., the voltage V2) from 600 V to 500 V in order to reduce the acoustic output power of the focused shock wave 354.

Circuit Embodiment with Ganged Retreat Transducer Unloading

Figure 26:
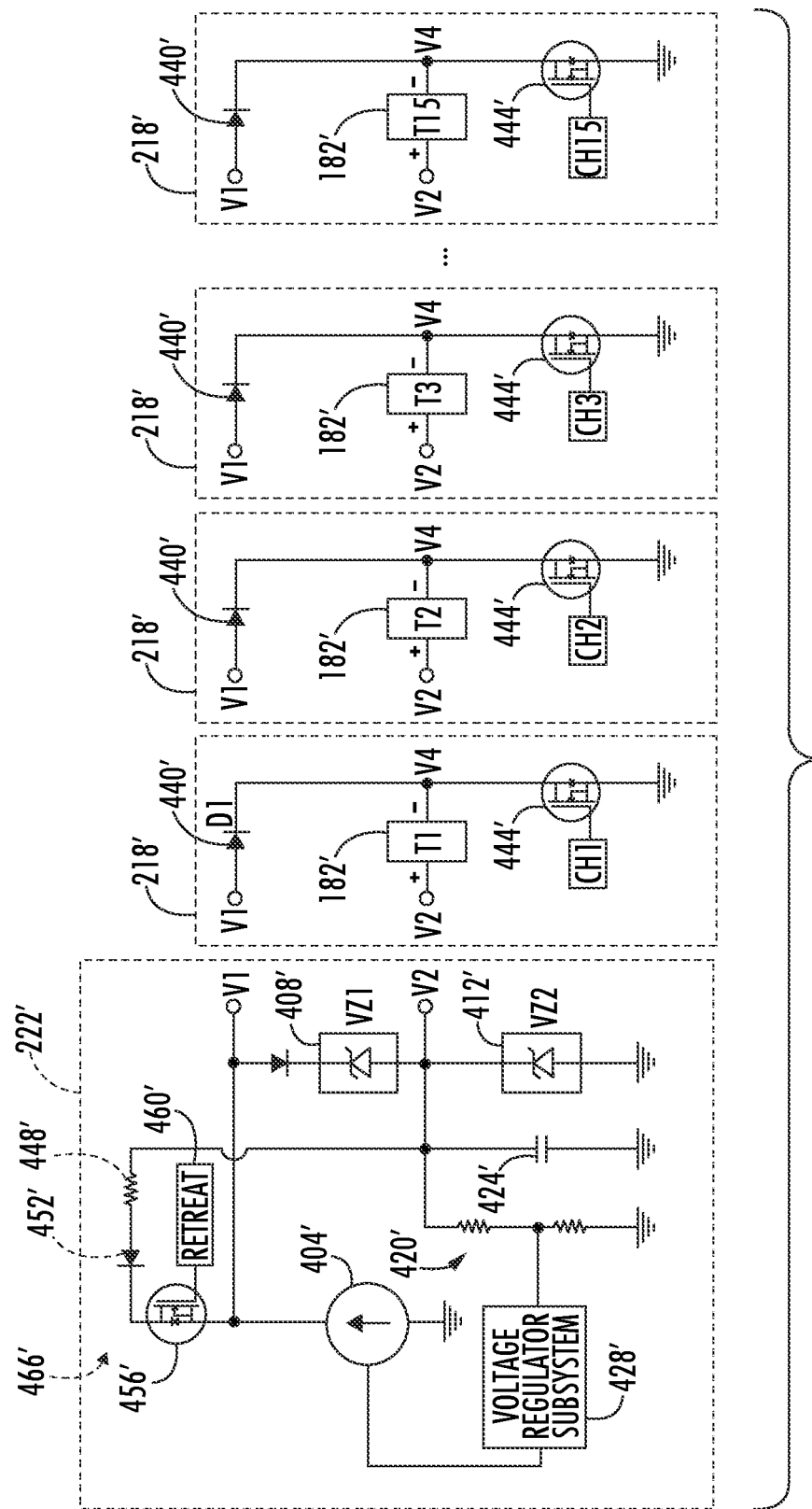
FIG. 26 is a schematic of another embodiment of a power supply circuit and a plurality of driver circuits, a ganged retreat from a coercive limit circuit is shown.

FIG. 26 illustrates another embodiment of the power supply circuit 222' and the driver circuits 218'. The drive circuits 218' include a diode 440', a switching element 444', and a corresponding piezoelectric element 182'.

In FIG. 26, instead of the discharge circuit 466 including the resistor 448 and the diode 452 draining charge from the piezoelectric elements 182, the power supply circuit 222' includes a discharge circuit 466' including the resistor 448', the diode 452', and the switch 456'. The discharge circuit 466' provides transducer unloading according to an approach referred to herein as the ganged retreat from the coercive limit method.

The power supply circuit 222' also includes a voltage regulator subsystem 428' for controlling the current output of the current source 404'. The switch 456' is provided as an N-channel MOSFET in an exemplary embodiment. In this embodiment, driver circuits 218' do not include the resistor 448 and the diode 452 and are otherwise unchanged. Accordingly, the discharge circuit 466' is even more compact and power efficient than the discharge circuit 466.

In FIG. 26, a source pin of the switch 456' is connected to the current source 404'. The cathode of the diode 452' is connected to a drain pin of the switch 456'. The diode 452' is biased to block current flow from the current source 404'. The resistor 448' is connected to the anode of the diode 452' and to the voltage divider 420', the capacitor 424', and to both of the voltage clamps 408', 412'. The switch 456' includes a control terminal 460' that is driven from the FPGA 216. In a specific embodiment, the control terminal 460' is a level-shifted replica of an output of the FPGA 216 to receive a retreat signal.

The circuit of FIG. 26 having the discharge circuit 466' provides an active drain of the charge on the piezoelectric elements 182 after the piezoelectric elements 182 generate the shock waves 264. This is because, both the switch 456' and the FPGA 216 are active devices. Whereas, in the previously-described resistor/diode per-channel method shown in FIG. 14, the discharge circuit 466 includes passive elements that passively drain the charge on the piezoelectric elements 182 after the piezoelectric elements 182 generate the shock waves 264.

With reference again to the method 1000 of FIG. 25, when the pre-charge voltage 510 is applied (i.e., block 1012), the microcontroller 228 uses the FPGA 216 to maintain the switch 456' of the discharge circuit 466' in an open state. Also, at block 1016, the switch 456' is configured in the open state during the generation of the individual shock waves 264. At block 1020, however, after the last piezoelectric element 182 has received the time-delayed fire signal based on the timing signals 396, the FPGA 216 briefly supplies the switch 456' with the retreat signal at the control terminal 460', which causes the switch 456' to close (i.e., to enter a closed state). Closing the switch 456' after the firing of each of the piezoelectric elements 182 quickly accomplishes two tasks. First, the current source 404' is un-collapsed by forcibly raising the output voltage of the current source 404' to the voltage V2. Second, the charge on each of the piezoelectric elements 182 is drained (in a ganged configuration, i.e., all at once) and the piezoelectric element 182 voltages are dropped to zero or near zero, thereby retreating the piezoelectric elements 182 from the coercive field imposed by the drive voltage pulse 514.

In an exemplary embodiment, the time interval that switch 456' is closed is less than a millisecond, which is enough time to unload charge from all the piezoelectric elements 182' in the transducer assembly 174. This occurs because all "n" replicated instances of the driver circuits 218' share voltage rails V1 and V2 and the current source 404'. The diode 452' negates the blocking action of an internal body diode of the switch 456' when the voltage across the switch 456' reverses. The magnitude of the resistance of the resistor 448' controls the rate of discharge of the piezoelectric elements 182 to a reasonable level.

After the stored charge on the piezoelectric elements 182' is drained, the switch 456' is opened and the current source 404' restores the piezoelectric elements 182 to the pre-charge phase of block 1012.

Direct to Patient Device

The f-ESWT device 104 of FIG. 1 is configured to be used by health professionals. The clinician has control over several parameters of the treatment such as the energy level, the number of the focused shock waves 354 produced, and the focal depth 356 by selecting a corresponding standoff structure 108.

Figure 27A:
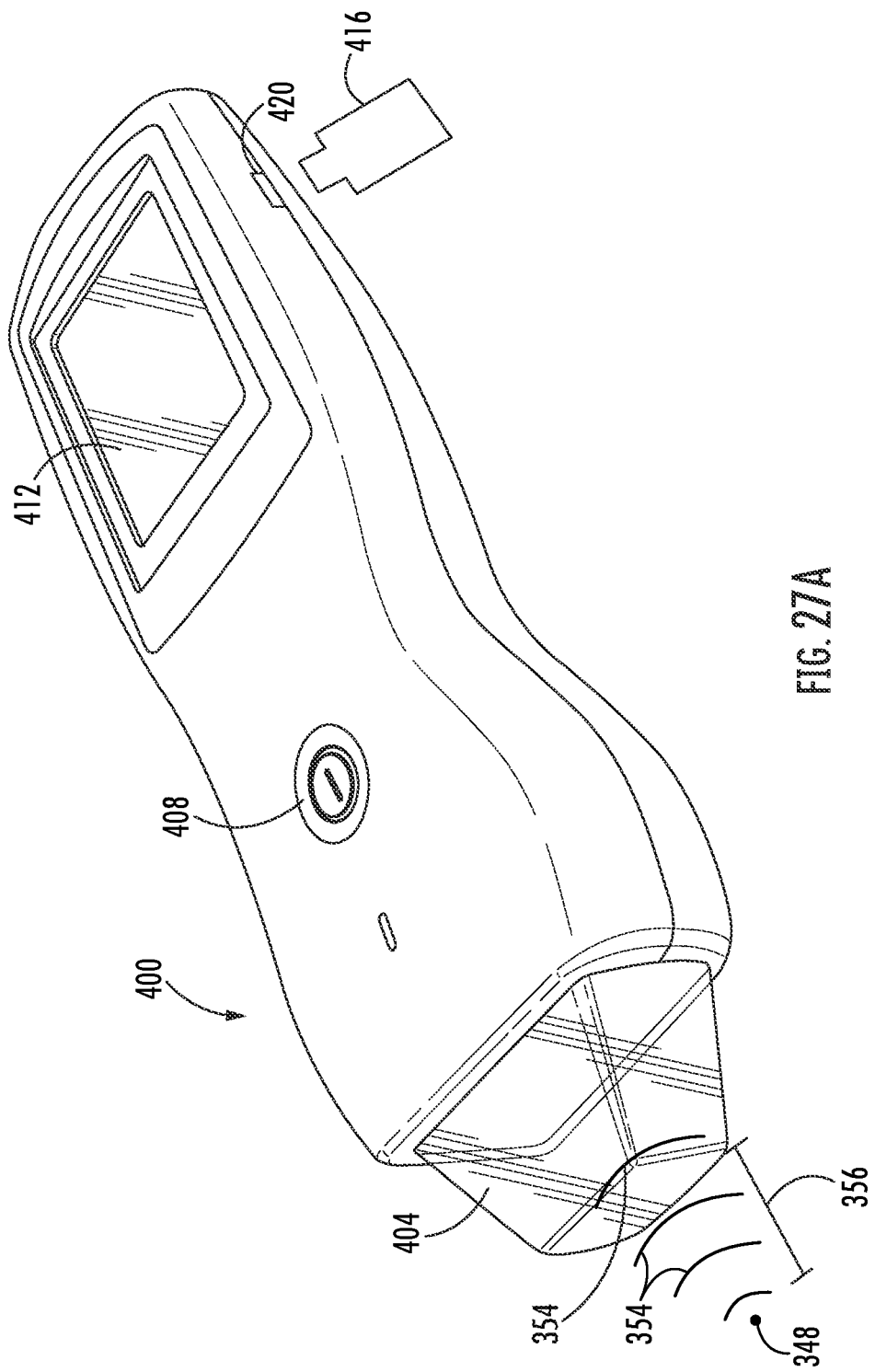
FIG. 27A illustrates another embodiment of the f-ESWT device that is configured for home usage by a patient.
Figure 27B:
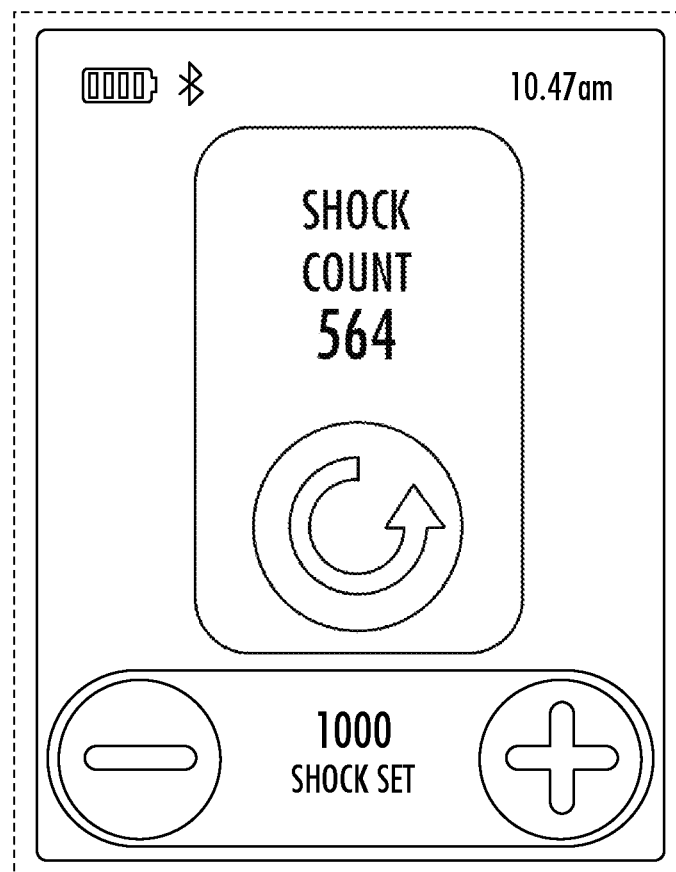
FIG. 27B illustrates a graphical user interface of the f-ESWT device of FIG. 27A.

FIGS. 27A and 27B illustrate a different f-ESWT device 400 that is simplified for "at-home" use by a patient with a doctor's prescription. The f-ESWT device 400 has a non-removable standoff structure 404, such that the focal depth 356 of the generated focused shock wave 354 is fixed. Moreover, the energy level of the focused shock wave 354 is not configurable by the patient as shown by the GUI of FIG. 27B. The patient can only change the number of focused shock waves 354 produced, as limited and/or prescribed by the physician. The f-ESWT device 400 includes an operating button 408 similar to the operating button 146 and a touchscreen 412 similar to the touchscreen 142, but more limited in functionality. The focused shock waves 354 are generated by the constructive combination of the individual shock waves 264.

The f-ESWT device 400 enables the physician or clinician (not the patient) to control (i) the number of focused shock waves 354 delivered over a predetermined time period, and (ii) the energy level of the focused shock waves 354 by programming a small dongle 416 configured to be installed into a programming port 420 (USBC, for example) of the f-ESWT device 400. The dongle 416 may be included with or integrated into the prescription received by the patient. In some embodiments, the f-ESWT device 400 provides additional physician control and/or data logging. For example, the f-ESWT device 400, in some embodiments, is configured for a wireless connection to a tablet, personal computer, and/or smartphone to enable communications capabilities with the physician's office.

While the disclosure has been illustrated and described in detail in the drawings and foregoing description, the same should be considered as illustrative and not restrictive in character. It is understood that only the preferred embodiments have been presented and that all changes, modifications and further applications that come within the spirit of the disclosure are desired to be protected.

What is claimed is:

1. A focused extracorporeal shock wave therapy (f-ESWT) device, comprising:
a handheld housing;
a battery located in the handheld housing;
a transducer assembly located in the handheld housing and operably connected to the battery; and
a microcontroller located in the handheld housing and operably connected to the battery and the transducer assembly, the microcontroller is configured to cause the transducer assembly to generate a focused shock wave using electrical energy from the battery.

2. The f-ESWT device as claimed in claim 1, wherein the transducer assembly comprises:
a plurality of piezoelectric elements configured to generate individual shock waves that combine to form the focused shock wave.

3. The f-ESWT device as claimed in claim 1, wherein the handheld housing is disconnected from electrical energy sources external to the handheld housing when the transducer assembly generates the focused shock wave.

4. The f-ESWT device as claimed in claim 1, wherein:
a rise time of the focused shock wave is from zero pressure to a positive pressure peak, and
the rise time less than thirty nanoseconds.

5. The f-ESWT device as claimed in claim 1, wherein the f-ESWT device weighs less than thirteen ounces.

6. The f-ESWT device as claimed in claim 1, wherein the f-ESWT device is configured for one-hand operation.

7. The f-ESWT device as claimed in claim 1, wherein:
the focused shock wave is not ultrasound, and
the focused shock wave is not a radial pressure wave.

8. The f-ESWT device as claimed in claim 1, wherein the focused shock wave has a broadband frequency response with a center frequency of 1.5 MHz.

9. The f-ESWT device as claimed in claim 1, wherein:
the focused shock wave has a positive pressure peak followed by a negative tensile wave component,
the positive pressure peak defines a positive magnitude,
the negative tensile wave component defines a negative magnitude, and
the negative magnitude is no more than 10% of the positive magnitude.

10. The f-ESWT device as claimed in claim 1, further comprising:
a standoff structure removably connected to the handheld housing and including a waveguide structure configured to receive and to transmit individual shock waves generated by the transducer assembly that combine to form the focused shock wave.

11. The f-ESWT device as claimed in claim 10, wherein the standoff structure is a first standoff structure having a first waveguide and defining a first focal depth, the f-ESWT device further comprising:
a second standoff structure removably connected to the handheld housing and including a second waveguide structure configured to receive and to transmit the individual shock waves generated by the transducer assembly that combine to form the focused shock wave, the second standoff structure defining a second focal depth that is different from the first focal depth; and
a standoff detection module located in the handheld housing and configured to detect which of the first standoff structure and the second standoff structure is connected to the handheld housing.

12. The f-ESWT device as claimed in claim 1, wherein the microcontroller is configured to cause the transducer assembly to generate a plurality of the focused shock waves at a predetermined repetition frequency.

13. The f-ESWT device as claimed in claim 12, further comprising:
a touchscreen mounted on the handheld housing and operably connected to the microcontroller; and
an operating button mounted on the handheld housing and operably connected to the microcontroller, the operating button configurable in a first state and a second state,
wherein the touchscreen is configured to receive at least one first user input corresponding to an energy flux density of the focused shock wave and at least one second user input corresponding to a number of the focused shock waves to be generated by the transducer assembly,
wherein the touchscreen is configured to display (i) data corresponding to the predetermined repetition frequency, (ii) data corresponding to the energy flux density of the focused shock wave, and (iii) data corresponding to the number of the focused shock waves generated by the transducer assembly,
wherein the microcontroller is configured to cause the transducer assembly to generate the focused shock waves when the operating button is in the first state, and
wherein the microcontroller is configured to cause the transducer assembly to stop generating the focused shock waves when the operating button is in the second state.

14. The f-ESWT device as claimed in claim 1, wherein:
the transducer assembly comprises:
a support frame located in the handheld housing and defining a plurality of receptacles; and
a plurality of piezoelectric elements, each piezoelectric element supported by the support frame and located in a corresponding receptacle of the plurality of receptacles,
each piezoelectric electric element is configured to generate an individual shock wave, and
the support frame supports the piezoelectric elements in an orientation configured to cause the individual shock waves to combine to form the focused shock wave.

15. The f-ESWT device as claimed in claim 14, wherein:
a front surface of each of the piezoelectric elements defines a normal axis,
the support frame supports each of the piezoelectric elements, such that the normal axes meet a focal point of the focused shock wave.

16. The f-ESWT device as claimed in claim 14, wherein:
the transducer assembly further comprises:
a first impedance matching layer applied to the plurality of piezoelectric elements; and
a second impedance matching layer applied to the first impedance matching layer,
at least one through-hole is formed in the first impedance matching layer and the second impedance matching layer, such that air passes through the first impedance matching layer and the second impedance matching layer via the at least one through-hole, and at least one of the first impedance matching layer and the second impedance matching layer includes cerium oxide powder.

17. The f-ESWT device as claimed in claim 14, wherein the transducer assembly further comprises:

a plurality of backing layer elements, each backing layer element supported by the support frame and located in a corresponding receptacle of the plurality of receptacles.

18. A focused extracorporeal shock wave therapy (f-ESWT) kit, comprising:

a handheld f-ESWT device including (i) a handheld housing, (ii) a rechargeable battery located in the handheld housing, (iii) a transducer assembly located in the handheld housing and operably connected to the rechargeable battery, and (iv) a microcontroller located in the handheld housing and operably connected to the battery and the transducer assembly, the microcontroller is configured to cause the transducer assembly to generate, using electrical energy from the rechargeable battery, a plurality of individual shock waves that combine to form a focused shock wave; and a plurality of standoff structures, each standoff structure configured for removable connection to the handheld housing of the f-ESWT device, and each standoff structure configured to transmit the plurality of individual shock waves when removably connected to the handheld housing of the f-ESWT device.

19. The f-ESWT kit of claim 18, wherein:

the individual shock waves of the plurality of individual shock waves constructively converge at a focal point of the focused shock wave, a first standoff structure of the plurality of standoff structures defines a first focal depth corresponding to a distance between the focal point and a corresponding treatment surface of the first standoff structure, a second standoff structure of the plurality of standoff structures defines a second focal depth corresponding to another distance between the focal point and a corresponding treatment surface of the second standoff structure, and the first focal depth is different from the second focal depth.

20. The f-ESWT kit of claim 19, further comprising:

a battery charger configured for connection to a supply of AC power; and a case configured to hold the handheld f-ESWT device, the plurality of standoff structures, and the battery charger, wherein the rechargeable battery is configured for removal from the handheld housing and configured for electrical connection to the battery charger, wherein the battery charger is configured to recharge the rechargeable battery, and wherein the handheld f-ESWT device is disconnected from the supply of AC power and the battery charger during generation of the focused shock wave.

* * * * *